(12) United States Patent
Chen et al.

(10) Patent No.: US 8,524,756 B2
(45) Date of Patent: Sep. 3, 2013

(54) COMPOUNDS FOR INFLAMMATION AND IMMUNE-RELATED USES

(71) Applicant: Synta Pharmaceuticals Corp., Lexington, MA (US)

(72) Inventors: Shoujun Chen, Bedford, MA (US); Jun Jiang, Norwood, MA (US); Hao Li, Brookline, MA (US); David A. James, Cambridge, MA (US); Dinesh Chimmanamada, Waltham, MA (US); Christopher Borella, Cambridge, MA (US); Lijun Sun, Harvard, MA (US); Yu Xie, Natick, MA (US); Mats Holmqvist, Malden, MA (US); Jerome Mahiou, Lexington, MA (US); Zhiqiang Xia, Acton, MA (US)

(73) Assignee: Synta Pharmaceuticals Corp., Lexington, MA (US)

( * ) Notice: Subject to any disclaimer, the term of this patent is extended or adjusted under 35 U.S.C. 154(b) by 0 days.

(21) Appl. No.: 13/652,878

(22) Filed: Oct. 16, 2012

(65) Prior Publication Data
US 2013/0142831 A1 Jun. 6, 2013

Related U.S. Application Data

(60) Division of application No. 12/718,366, filed on Mar. 5, 2010, now Pat. No. 8,314,134, which is a continuation of application No. 11/233,224, filed on Sep. 21, 2005, now Pat. No. 7,709,518.

(60) Provisional application No. 60/611,913, filed on Sep. 21, 2004.

(51) Int. Cl.
*A01N 43/52* (2006.01)
*A61K 31/415* (2006.01)

(52) U.S. Cl.
USPC ....................................................... 514/393

(58) Field of Classification Search
USPC .......................................................... 514/393
See application file for complete search history.

(56) References Cited

U.S. PATENT DOCUMENTS

| | | | |
|---|---|---|---|
| 3,536,809 A | 10/1970 | Applezweig | |
| 3,598,123 A | 8/1971 | Zaffaroni | |
| 3,845,770 A | 11/1974 | Theeuwes et al. | |
| 3,916,899 A | 11/1975 | Theeuwes et al. | |
| 4,008,719 A | 2/1977 | Theeuwes et al. | |
| 4,898,872 A | 2/1990 | Campbell et al. | |
| 5,025,000 A * | 6/1991 | Karanewsky ............. | 514/80 |
| 5,059,595 A | 10/1991 | Le Grazie | |
| 5,073,543 A | 12/1991 | Marshall et al. | |
| 5,120,548 A | 6/1992 | McClelland et al. | |
| 5,322,847 A | 6/1994 | Marfat et al. | |
| 5,354,556 A | 10/1994 | Sparks et al. | |
| 5,563,151 A | 10/1996 | Bowles et al. | |
| 5,591,767 A | 1/1997 | Mohr et al. | |
| 5,639,476 A | 6/1997 | Oshlack et al. | |
| 5,674,533 A | 10/1997 | Santus et al. | |
| 5,733,566 A | 3/1998 | Lewis | |
| 6,020,357 A | 2/2000 | Pinto et al. | |
| 6,274,171 B1 | 8/2001 | Sherman et al. | |
| 6,339,099 B1 | 1/2002 | Lam et al. | |
| 6,569,880 B2 | 5/2003 | Jensen et al. | |
| 6,897,208 B2 | 5/2005 | Edwards et al. | |
| 7,074,801 B1 | 7/2006 | Yoshida et al. | |
| 7,709,518 B2 | 5/2010 | Chen et al. | |
| 8,314,134 B2 | 11/2012 | Chen et al. | |
| 2002/0099089 A1 | 7/2002 | Hauel et al. | |
| 2003/0004203 A1 | 1/2003 | Sircar et al. | |
| 2004/0019059 A1 | 1/2004 | Freyne et al. | |
| 2005/0096298 A1 | 5/2005 | Metcalf et al. | |
| 2006/0223837 A1 | 10/2006 | Codd et al. | |
| 2007/0249661 A1 | 10/2007 | Chen et al. | |

FOREIGN PATENT DOCUMENTS

| | | |
|---|---|---|
| DE | 4330959 A1 | 3/1995 |
| EP | 1 382 603 A1 | 1/2004 |
| WO | WO 91/17162 A1 | 11/1991 |
| WO | WO 95/07263 A1 | 3/1995 |
| WO | WO 98/57951 A1 | 12/1998 |
| WO | WO 00/01676 A1 | 1/2000 |
| WO | WO 00/21959 A1 | 4/2000 |
| WO | WO 01/19788 A2 | 3/2001 |
| WO | WO 03/004458 A1 | 1/2003 |
| WO | WO 03/035065 A1 | 5/2003 |
| WO | WO 03/080610 A1 | 10/2003 |
| WO | WO 2004/011427 A2 | 2/2004 |
| WO | WO 2004/056784 A1 | 7/2004 |
| WO | WO 2005/091752 A2 | 10/2005 |
| WO | WO 2006/045756 A1 | 5/2006 |

OTHER PUBLICATIONS

Extended European Search Report for EP 05814906.3 mailed Jul. 9, 2008.
International Search Report for PCT/US2005/033980 mailed May 30, 2007.
International Preliminary Report on Patentability for PCT/US2005/033980 mailed Jul. 19, 2007.
Office Communication mailed Nov. 21, 2008 for U.S. Appl. No. 11/233,224.
Office Communication mailed Jun. 4, 2009 for U.S. Appl. No. 11/233,224.
Notice of Allowance mailed Dec. 7, 2009 for U.S. Appl. No. 11/233,224.

(Continued)

*Primary Examiner* — Niloofar Rahmani
(74) *Attorney, Agent, or Firm* — Wolf, Greenfield & Sacks, P.C.

(57) ABSTRACT

The invention relates to compounds of formula (I):

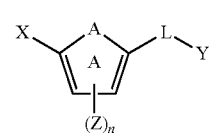

or a pharmaceutically acceptable salt, solvate, clathrate, or prodrug thereof wherein X, Y, A, Z, L and n are defined herein. These compounds are useful as immunosuppressive agents and for treating and preventing inflammatory conditions and immune disorders.

25 Claims, No Drawings

(56) References Cited

OTHER PUBLICATIONS

Office Communication mailed Dec. 14, 2011 for U.S. Appl. No. 12/718,366.

Notice of Allowance mailed Jul. 16, 2012 for U.S. Appl. No. 12/718,366.

Launay et al., TRPM4 is a Ca2+-activated nonselective cation channel mediating cell membrane depolarization. Cell. May 3, 2002;109(3):397-407.

Lee et al., Inhibitory effect of a tyrosine-fructose Maillard reaction product, 2,4-bis(p-hydroxyphenyl)-2-butenal on amyloid-β generation and inflammatory reactions via inhibition of NF-κB and STAT3 activation in cultured astrocytes and microglial BV-2 cells. J Neuroinflammation. 2011;8:132. 15 pages.

Lewis, Calcium oscillations in T-cells: mechanisms and consequences for gene expression. Biochem Soc Trans. Oct. 2003;31(Pt 5):925-9.

Qiao et al., 5-Amidinobenzo[b]thiophenes as dual inhibitors of factors IXa and Xa. Bioorg Med Chem Lett. Jan. 3, 2005;15(1):29-35.

Ribeiro et al., Analgesic effect of thalidomide on inflammatory pain. Eur J Pharmacol. Mar. 10, 2000;391(1-2):97-103.

* cited by examiner

COMPOUNDS FOR INFLAMMATION AND IMMUNE-RELATED USES

CROSS-REFERENCE TO RELATED APPLICATIONS

This application is a divisional of U.S. patent application Ser. No. 12/718,366, filed Mar. 5, 2010, which is a continuation of U.S. patent application Ser. No. 11/233,224, filed Sep. 21, 2005, which claims priority under 35 U.S.C. §119(e) to U.S. Provisional Patent Application Ser. No. 60/611,913, filed Sep. 21, 2004, the contents of which applications are incorporated herein by reference in their entirety.

FIELD OF THE INVENTION

This invention relates to biologically active chemical compounds that may be used for immunosuppression or to treat or prevent inflammatory conditions and immune disorders.

BACKGROUND OF THE INVENTION inflammation is a mechanism that protects mammals from invading pathogens. However, while transient inflammation is necessary to protect a mammal from infection, uncontrolled inflammation causes tissue damage and is the underlying cause of many illnesses. Inflammation is typically initiated by binding of an antigen to T-cell antigen receptor. Antigen binding by a T-cell initiates calcium influx into the cell via calcium ion channels, such as $Ca^{2+}$-release-activated $Ca^{2+}$ channels (CRAC). Calcium ion influx in turn initiates a signaling cascade that leads to activation of these cells and an inflammatory response characterized by cytokine production.

TRPM4 is a $Ca^{2+}$-activated non-selective (CAN) cation channel that mediates depolarization of cellular membranes. Activation of TRPM4 depolarizes the cellular membrane which decreases the driving force for calcium ion influx into the cell. Conversely, it has been shown that, inhibition of TRPM4 channels in T-lymphocytes increases calcium ion influx into the cell and induces large increases in cytokine production and, in particular, increase the production of interleukin 2 (IL-2).

Kv1.3 is a voltage-dependent potassium ion channel which is selectively distributed in T lymphocytes. Activation of Kv1.3 channels hyperpolarizes the cell membrane and facilitates calcium ion influx into the cell. Inhibition of Kv1.3 is believed to inhibit T-cell activation. It has recently been shown that myelin-reactive T-cells in patients with multiple sclerosis (MS) exhibit upregulated Kv1.3 expression after activation with myelin antigens. Therefore, inhibitors of Kv1.3 channels could be therapeutically useful in treating MS and other T-cell mediated autoimmune diseases.

IL-2 is a cytokine that is secreted by T cells in response to calcium ion influx into the cell. IL-2 modulates immunological effects on many cells of the immune system. For example, it is a potent T cell mitogen that is required for the T cell proliferation, promoting their progression from G1 to S phase of the cell cycle; it stimulates the growth of NK cells; and it acts as a growth factor to B cells and stimulates antibody synthesis.

IL-2, although useful in the immune response, can cause a variety of problems. IL-2 damages the blood-brain barrier and the endothelium of brain vessels. These effects may be the underlying causes of neuropsychiatric side effects observed under IL-2 therapy, e.g. fatigue, disorientation and depression. It also alters the electrophysiological behaviour of neurons.

Due to its effects on both T and B cells, IL-2 is a major central regulator of immune responses. It plays a role in inflammatory reactions, tumour surveillance, and hematopoiesis. It also affects the production of other cytokines, inducing IL-1, TNF-α and TNF-β secretion, as well as stimulating the synthesis of IFN-γ in peripheral leukocytes.

T cells that are unable to produce IL-2 become inactive (anergic). This renders them potentially inert to any antigenic stimulation they might receive in the future. As a result, agents which inhibit IL-2 production can be used for immunosuppression or to treat or prevent inflammation and immune disorders. This approach has been clinically validated with immunosuppressive drugs such as cyclosporin, FK506, and RS61443. Despite this proof of concept, agents that inhibit IL-2 production remain far from ideal. Among other problems, efficacy limitations and unwanted side effects (including dose-dependant nephrotoxicity and hypertension) hinder their use.

Over-production of proinflammatory cytokines other than IL-2 has also been implicated in many autoimmune diseases. For example, Interleukin 5 (IL-5), a cytokine that increases the production of eosinophils, is increased in patients with asthma. Overproduction of IL-5 is associated with accumulation of eosinophils in the asthmatic bronchial mucosa, a hall mark of allergic inflammation. Thus, patients with asthma and other inflammatory disorders involving the accumulation of eosinophils would benefit from the development of new drugs that inhibit the production of IL-5.

Interleukin 4 (IL-4) and interleukin 13 (IL-13) have been identified as mediators of the hypercontractility of smooth muscle found in inflammatory bowel disease and asthma. Thus, patients with asthma and inflammatory bowel disease would benefit from the development of new drugs that inhibit IL-4 and IL-13 production.

Granulocyte macrophage-colony stimulating factor (GM-CSF) is a regulator of maturation of granulocyte and macrophage lineage population and has been implicated as a key factor in inflammatory and autoimmune diseases. Anti-GM-CSF antibody blockade has been shown to ameliorate autoimmune disease. Thus, development of new drugs that inhibit the production of GM-CSF would be beneficial to patients with an inflammatory or autoimmune disease.

There is therefore a continuing need for new drugs which overcome one or more of the shortcomings of drugs currently used for immunosuppression or in the treatment or prevention of inflammatory disorders and autoimmune disorders.

Desirable properties of new drugs include efficacy against diseases or disorders that are currently untreatable or poorly treatable, a new mechanism of action, oral bioavailability and/or reduced side effects.

SUMMARY OF THE INVENTION

This invention meets the above-mentioned needs by providing compounds that inhibit the production of IL-2, IL-4, IL-5, IL-13, GM-CSF, TNF-α, and IFNγ. These compounds are particularly useful for immunosuppression and/or to treat or prevent inflammatory conditions and immune disorders.

In one embodiment, the invention relates to compounds represented by formula (I):

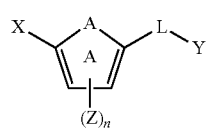

(I)

or a pharmaceutically acceptable salt, solvate, clathrate, or prodrug thereof, wherein:

X is an optionally substituted benzoimidazolyl, an optionally substituted 5,6,7,8-tetrahydroindolizinyl, an optionally substituted imidazo[4,5-a]pyridyl, an optionally substituted imidazo[1,2-a]pyridyl, an optionally substituted imidazo[4,5-b]pyridyl, or an optionally substituted imidazo[4,5-c]pyridyl;

Y is an unsubstituted alkyl, an optionally substituted alkenyl, an optionally substituted cycloalkyl, an optionally substituted cycloalkenyl, an optionally substituted aryl, an optionally substituted heteroaryl, or an optionally substituted heteroaralkyl;

A is —O—, —S(O)$_p$—, —NH—, —NZ—, —CH=CH—, —CZ=CH—, —CH=CZ—, —CZ=CZ—, —N=CH—, —N=CZ—, —CH=N—, —CZ=N—, or an N-oxide of —N=CH—, —N=CZ—, —CH=N—, or —CZ=N—;

Z, for each occurrence, is independently selected from the group consisting of an optionally substituted alkyl, an optionally substituted alkenyl, an optionally substituted alkynyl, an optionally substituted cycloalkyl, an optionally substituted cycloalkenyl, an optionally substituted heterocyclyl, an optionally substituted aryl, an optionally substituted heteroaryl, an optionally substituted aralkyl, an optionally substituted heteraralkyl, a haloalkyl, —C(O)NR$_1$R$_2$, —NR$_4$C(O)R$_5$, halo, —OR$_4$, cyano, nitro, haloalkoxy, —C(O)R$_4$, —NR$_1$R$_2$, —C(O)OR$_4$, —OC(O)R$_4$, —NR$_4$C(O)NR$_1$R$_2$, —OC(O)NR$_1$R$_2$, —NR$_4$C(O)OR$_5$, —S(O)$_p$R$_4$, or —S(O)$_h$NR$_1$R$_2$;

L is a linker selected from the group consisting of an optionally substituted lower alkyl, and optionally substituted lower alkenyl, —NRCR$_4$R$_5$—, —C(O)—, —OC(O)—, —C(O)O—, —NR—C(O)—, —C(O)—NR—, —NR—C(O)—NR—, —C(S)—, —NR—S(O)$_h$—, —S(O)$_h$—NR—, —NR—C(=NR)—, —NR—C(=NR)—NR—, —NR—C(=N—CN)—NR—, —NR—C(=N—NO$_2$)—NR—, —NR—C(S)—, —C(S)—NR—, or —NR—C(S)—NR—;

R, for each occurrence, is independently selected from —H, an alkyl, acetyl, alkoxycarbonyl, or aralkoxycarbonyl;

R$_1$ and R$_2$, for each occurrence are, independently, H, an optionally substituted alkyl, an optionally substituted alkenyl, an optionally substituted alkynyl, an optionally substituted cycloalkyl, an optionally substituted cycloalkenyl, an optionally substituted heterocyclyl, an optionally substituted aryl, an optionally substituted heteroaryl, an optionally substituted aralkyl, or an optionally substituted heteraralkyl; or R$_1$ and R$_2$ taken together with the nitrogen to which they are attached is optionally substituted heterocyclyl or optionally substituted heteroaryl;

R$_4$ and R$_5$ for each occurrence are, independently, H, an optionally substituted alkyl, an optionally substituted alkenyl, an optionally substituted alkynyl, an optionally substituted cycloalkyl, an optionally substituted cycloalkenyl, an optionally substituted heterocyclyl, an optionally substituted aryl, an optionally substituted heteroaryl, an optionally substituted aralkyl, or an optionally substituted heteraralkyl;

h is 1 or 2;

n is 0 or an integer from 1 to 4; and p, for each occurrence, is, independently, 0, 1, or 2.

In another embodiment, the invention relates to compounds represented by formula (II):

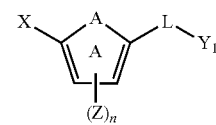

(I)

or a pharmaceutically acceptable salt, solvate, clathrate, or prodrug thereof wherein:

Y$_1$ is an alkyl, a heterocyclyl, or an aralkyl, wherein the alkyl, heterocyclyl or aralkyl is optionally substituted with one or more substituent selected from the group consisting of an alkyl, an alkynyl, an cycloalkyl, an cycloalkenyl, an heterocyclyl, an aryl, an heteraralkyl, a haloalkyl, —C(O)NH$_2$, —NR$_4$C(O)R$_5$, halo, —OR$_4$, cyano, nitro, haloalkoxy, —C(O)R$_4$, —NR$_1$R$_2$, —SR$_4$, —C(O)OH, —OC(O)R$_4$, —NR$_4$C(O)NR$_1$R$_2$, —OC(O)NR$_1$R$_2$, —NR$_4$C(O)OR$_5$, —S(O)$_p$R$_4$, or —S(O)$_h$NR$_1$R$_2$; and X, R$_1$, R$_2$, R$_4$, R$_5$, A, L, Z, h, n and p are defined as for formula (I).

In another embodiment, the invention relates to compounds represented by formula (III):

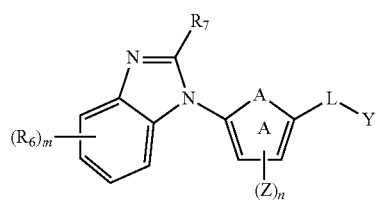

(III)

or a pharmaceutically acceptable salt, solvate, clathrate, or prodrug thereof wherein:

R$_6$, for each occurrence, and R$_7$ are, independently, selected from the group consisting of an optionally substituted alkyl, an optionally substituted alkenyl, an optionally substituted alkynyl, an optionally substituted cycloalkyl, an optionally substituted cycloalkenyl, an optionally substituted heterocyclyl, an optionally substituted aryl, an optionally substituted heteroaryl, an optionally substituted aralkyl, an optionally substituted heteraralkyl, a haloalkyl, —C(O)NR$_1$R$_2$, —NR$_4$C(O)R$_5$, halo, —OR$_4$, cyano, nitro, haloalkoxy, —C(O)R$_4$, —NR$_1$R$_2$, —C(O)OR$_4$, —OC(O)R$_4$, —NR$_4$C(O)NR$_1$R$_2$, —OC(O)NR$_1$R$_2$, —NR$_4$C(O)OR$_5$, —S(O)R$_4$, or —S(O)$_h$NR$_1$R$_2$;

m is 0 or an integer from 1 to 4; and

Y, R$_1$, R$_2$, R$_4$, R$_5$, A, L, Z, h, n and p are defined as for formula (I).

In another embodiment, the invention relates to compounds represented by formula (IV):

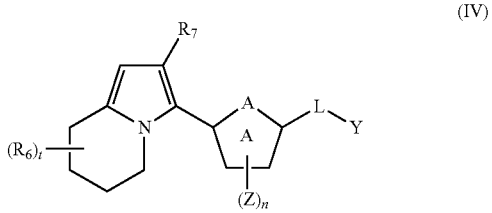

or a pharmaceutically acceptable salt, solvate, clathrate, or prodrug thereof wherein t is 0 or an integer from 1 to 8; Y, A, Z, and n are defined as in formula (I); and $R_6$ and $R_7$ are defined as in formula (III).

In another embodiment, the invention relates to compounds represented by formula (V):

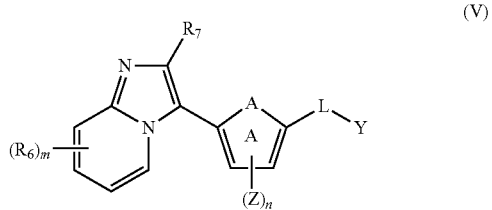

or a pharmaceutically acceptable salt, solvate, clathrate, or prodrug thereof wherein Y, L, A, Z, and n are defined as in formula (I); and $R_6$, $R_7$ and m are defined as in formula (III).

In another embodiment, the invention relates to compounds represented by formula (VI):

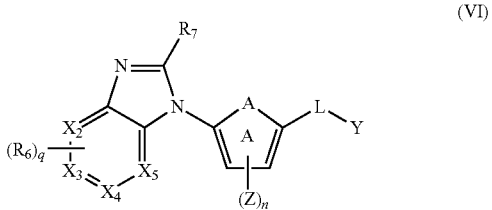

or a pharmaceutically acceptable salt, solvate, clathrate, or prodrug thereof wherein:
one of $X_2$, $X_3$, $X_4$, or $X_5$ is N and the others are, independently, CH or $CR_6$,
q is 0 or an integer from 1 to 3;
Y, L, A, Z, and n are defined as in formula (I); and
$R_6$ and $R_7$ are defined as in formula (III).

A compound of the invention or a pharmaceutically acceptable salt, solvate, clathrate, or prodrug thereof is particularly useful inhibiting immune cell (e.g., T-cells, B-cells and/or mast cells) activation (e.g., activation in response to an antigen). In particular, a compound of the invention or a pharmaceutically acceptable salt, solvate, clathrate, or prodrug thereof can inhibit immune cell proliferation and inhibit the production of certain cytokines that regulate immune cell activation. For example, a compound of the invention or a pharmaceutically acceptable salt, solvate, clathrate, or prodrug thereof can inhibit the production of IL-2, IL-4, IL-5, IL-13, GM-CSF, TNF-α, INF-γ and combinations thereof. Moreover, a compound of the invention or a pharmaceutically acceptable salt, solvate, clathrate, or prodrug thereof can modulate the activity of one or more ion channel involved in activation of immune cells, such as CRAC, TRPM4, and Kv1.3 ion channels.

A compound of the invention or a pharmaceutically acceptable salt, solvate, clathrate, or prodrug thereof is particularly useful for immunosuppression or for treating or preventing inflammatory conditions, immune disorders or allergic disorders.

The invention also encompasses pharmaceutical compositions comprising an effective amount of a compound of the invention or a pharmaceutically acceptable salt, solvate, clathrate, or prodrug thereof; and a pharmaceutically acceptable carrier or vehicle. These compositions may further comprise additional agents. These compositions are useful for treating or preventing inflammatory conditions, immune disorders and allergic disorders.

The invention further encompasses methods for treating or preventing inflammatory conditions, immune disorders and allergic disorders, comprising administering to a subject in need thereof a compound of the invention or a pharmaceutically acceptable salt, solvate, clathrate, or prodrug thereof, or a pharmaceutical composition comprising a compound of the invention or a pharmaceutically acceptable salt, solvate, clathrate, or prodrug thereof. These methods may also comprise administering to the subject an additional agent separately or in a combination composition with the compound of the invention or a pharmaceutically acceptable salt, solvate, clathrate, or prodrug thereof.

The invention further encompasses methods for suppressing the immune system of a subject, comprising administering to a subject in need thereof a compound of the invention or a pharmaceutically acceptable salt, solvate, clathrate, or prodrug thereof, or a pharmaceutical composition comprising a compound of the invention or a pharmaceutically acceptable salt, solvate, clathrate, or prodrug thereof. These methods may also comprise administering to the subject an additional agent separately or in a combination-composition with the compound of the invention or a pharmaceutically acceptable salt, solvate, clathrate, or prodrug thereof.

The invention further encompasses methods for inhibiting immune cell activation, including inhibiting proliferation of immune cells (e.g., T cells, B cells and/or mast cells), in vivo or in vitro using an effective amount of a compound of the invention or a pharmaceutically acceptable salt, solvate, clathrate, or prodrug thereof or a pharmaceutical composition comprising an effective amount of a compound of the invention or a pharmaceutically acceptable salt, solvate, clathrate, or prodrug thereof.

The invention further encompasses methods for inhibiting cytokine production, (e.g., IL-2, IL-4, IL-5, IL-13, GM-CSF, TNF-α, and/or INF-γ production) in vivo or in vitro using an effective amount of a compound of the invention or a pharmaceutically acceptable salt, solvate, clathrate, or prodrug thereof or a pharmaceutical composition comprising an effective amount of a compound of the invention or a pharmaceutically acceptable salt, solvate, clathrate, or prodrug thereof.

The invention further encompasses methods for modulating ion channel activity, and in particular, modulating the activity of ion channels involved in immune cell activation (e.g., CRAC, TRPM4, and/or Kv1.3), in vivo or in vitro using an effective amount of a compound of the invention or a pharmaceutically acceptable salt, solvate, clathrate, or prodrug thereof or a pharmaceutical composition comprising an effective amount of a compound of the invention or a pharmaceutically acceptable salt, solvate, clathrate, or prodrug thereof.

All of the methods of this invention may be practice with a compound of the invention alone, or in combination with other agents, such as other immunosuppressive, anti-inflammatory or immune disorder agents.

DETAILED DESCRIPTION OF THE INVENTION

Definitions

Unless otherwise specified, the below terms used herein are defined as follows:

As used herein, the term an "aromatic ring" or "aryl" means a monocyclic or polycyclic-aromatic ring or ring radical composed of carbon and hydrogen atoms. Examples of suitable aryl groups include, but are not limited to, phenyl, tolyl, anthacenyl, fluorenyl, indenyl, azulenyl, and naphthyl, as well as benzo-fused carbocyclic moieties such as 5,6,7,8-tetrahydronaphthyl. An aryl group can be unsubstituted or substituted with one or more substituents (including without limitation alkyl (preferably, lower alkyl), haloalkyl (preferably trifluoromethyl), hydroxy, alkoxy (preferably, lower alkoxy), alkylsulfanyl (preferably, a lower alkylsulfanyl), cyano, halo, amino, and nitro. In certain embodiments, the aryl group is a monocyclic ring, wherein the ring comprises 6 carbon atoms.

As used herein, the term "alkyl" means a saturated straight chain or branched non-cyclic hydrocarbon typically having from 1 to 10 carbon atoms. Representative saturated straight chain alkyls include methyl, ethyl, n-propyl, n-butyl, n-pentyl, n-hexyl, n-heptyl, n-octyl, n-nonyl and n-decyl; while saturated branched alkyls include isopropyl, sec-butyl, isobutyl, tert-butyl, isopentyl, 2-methylbutyl, 3-methylbutyl, 2-methylpentyl, 3-methylpentyl, 4-methylpentyl, 2-methylhexyl, 3-methylhexyl, 4-methylhexyl; 5-methylhexyl, 2,3-dimethylbutyl, 2,3-dimethylpentyl, 2,4-dimethylpentyl, 2,3-dimethylhexyl, 2,4-dimethylhexyl, 2,5-dimethylhexyl, 2,2-dimethylpentyl, 2,2-dimethylhexyl, 3,3-dimethylpentyl, 3,3-dimethylhexyl, 4,4-dimethylhexyl, 2-ethylpentyl, 3-ethylpentyl, 2-ethylhexyl, 3-ethylhexyl, 4-ethylhexyl, 2-methyl-2-ethylpentyl, 2-methyl-3-ethylpentyl, 2-methyl-4-ethylpentyl, 2-methyl-2-ethylhexyl, 2-methyl-3-ethylhexyl, 2-methyl-4-ethylhexyl, 2,2-diethylpentyl, 3,3-diethylhexyl, 2,2-diethylhexyl, 3,3-diethylhexyl and the like. Alkyl groups included in compounds of this invention may be optionally substituted with one or more substituents, such as amino, alkylamino, alkoxy, alkylsulfanyl, arylsulfanyl, halo, acyl, nitro, hydroxyl, cyano, aryl, aralkyl, aryloxy, arylthio, arylamino, carbocyclyl, carbocyclyloxy, carbocyclylthio, carbocyclylamino, heterocyclyl, heterocyclyloxy, heterocyclylamino, heterocyclylthio, and the like. In addition, any carbon in the alkyl segment may be substituted with oxygen (=O), sulfur (=S), or nitrogen (=NR$^{23}$, wherein R$^{23}$ is —H, an alkyl, acetyl, or aralkyl). Lower alkyls are typically preferred for the compounds of this invention.

The term alkylene refers to an alkyl or cycloalkyl group that has at least two points of attachment to at least two moieties (e.g., {—CH$_2$—}, —{CH$_2$CH$_2$—},

etc., wherein the brackets indicate the points of attachment). Alkylene groups may be substituted or unsubstituted.

The term "aralkyl" or "arylalkyl," as used herein, refers to an aryl group that is attached to another moiety via an alkylene linker. Aralkyl groups can be substituted or unsubstituted.

The term "alkoxy," as used herein, refers to an alkyl group which is linked to another moiety though an oxygen atom. Alkoxy groups can be substituted or unsubstituted.

As used herein, the term "alkenyl" means an alkyl radical typically having from 2 to 10 carbon atoms and having at least one carbon-carbon double bond. Representative straight chain and branched alkenyls include vinyl, allyl, 1-butenyl, 2-butenyl, isobutylenyl, 1-pentenyl, 2-pentenyl, 3-methyl-1-butenyl, methyl-2-butenyl, 2,3-dimethyl-2-butenyl, 1-hexenyl, 2-hexenyl, 3-hexenyl, 1-heptenyl, 2-heptenyl, 3-heptenyl, 1-octenyl, 2-octenyl, 3-octenyl, 1-nonenyl, 2-nonenyl, 3-nonenyl, 1-decenyl, 2-decenyl, 3-decenyl and the like. Alkenyl groups can be substituted or unsubstituted.

As used herein, the term "alkynyl" means an alkyl radical typically having from 2 to 10 carbon atoms and having at lease one carbon-carbon triple bond. Representative straight chain and branched alkynyls include acetylenyl, propynyl, 1-butynyl, 2-butynyl, 1-pentynyl, 2-pentynyl, 3-methyl-1-butynyl, 4-pentynyl, -1-hexynyl, 2-hexynyl, 5-hexynyl, 1-heptynyl, 2-heptynyl, 6-heptynyl, 1-octynyl, 2-octynyl, 7-octynyl, 1-nonynyl, 2-nonynyl, 8-nonynyl, 1-decynyl, 2-decynyl, 9-decynyl and the like. Alkynyl groups can be substituted or unsubstituted.

As used herein, the term "cycloalkyl" means a saturated cyclic alkyl radical typically having from 3 to 10 carbon atoms. Representative cycloalkyls include cyclopropyl, cyclobutyl, cyclopentyl, cyclohexyl, cycloheptyl, cyclooctyl, cyclononyl, and cyclodecyl. Cycloalkyl groups can be substituted or unsubstituted.

As used herein, the term "bicycloalkyl" means a bi-cyclic alkyl system typically having from 8 to 14 carbon atoms and at least one saturated cyclic alkyl ring. Representative bicyclocycloalkyls include decahydronaphthyl, adamantyl, bicycle[4.3.3]dodecyl, and the like. Bicycloalkyl groups can be substituted or unsubstituted.

As used herein, the term "cycloalkenyl" means a cyclic non-aromatic alkenyl radical having at least one carbon-carbon double bond in the cyclic system and typically having from 5 to 10 carbon atoms. Representative cycloalkenyls include cyclopentenyl, cyclopentadienyl, cyclohexenyl, cyclohexadienyl, cycloheptenyl, cycloheptadienyl, cycloheptatrienyl, cyclooctenyl, cyclooctadienyl, cyclooctatrienyl, cyclooctatetraenyl, cyclononenyl, cyclononadienyl, cyclodecenyl, cyclodecadienyl and the like. Cycloalkenyl groups can be substituted or unsubstituted.

As used herein, the term "carbocycle" or "carbocyclyl" refers collectively to cycloalkyls, cycloalkenyls, and bicycloalkyls. A carbocycle can be substituted or unsubstituted.

As used herein, the term "heterocycle" or "heterocyclyl" means a monocyclic (typically having 3- to 10-members) or a polycyclic (typically having 8- to 14-members) heterocyclic ring which is either a saturated ring or a unsaturated non-aromatic ring. A 3- to 10-membered heterocycle can contain up to 5 heteroatoms; and a 8- to 14-membered heterocycle can contain up to 6 heteroatoms. Typically, a heterocycle has at least on carbon atom ring member. Each heteroatom is independently selected from nitrogen, which can be oxidized (e.g., N(O)) quaternized; oxygen; and sulfur, including sulfoxide and sulfone. The heterocycle may be attached via any heteroatom or carbon atom. Representative heterocycles include morpholinyl, thiomorpholinyl, pyrrolidinonyl, pyrrolidinyl, piperidinyl, piperazinyl, hydantoinyl, valerolactamyl, oxiranyl, oxetanyl, tetrahydrofuranyl, tetrahydropyranyl, tetrahydropyrindinyl, tetrahydropyrimidinyl, tetrahydrothiophenyl, tetrahydrothiopyranyl, and the like. A heteroatom may be substituted with a protecting group known to those of ordinary skill in the art, for example, the hydrogen on a nitrogen may be substituted with a tert-butoxycarbonyl group. Furthermore, the heterocyclyl may be optionally substituted with one or more substituents (including without limitation a halogen atom, an alkyl radical, or aryl radical). Only stable isomers of such substituted heterocyclic groups are contemplated in this definition. Heterocyclyl groups can be substituted or unsubstituted.

As used herein, the term "heteroaromatic" or "heteroaryl" means a monocyclic (typically having 5- to 10-members) or polycyclic (typically having 8- to 14-members) heteroaromatic ring (or radical thereof) comprising carbon atom ring members and one or more heteroatom ring members, such as, for example, oxygen, sulfur (including S(O) and S(O)$_2$) or nitrogen (including N(O) or quaternized nitrogen). In one embodiment, the heteroaromatic ring is selected from 5-8 membered heteroaryl rings. In another embodiment, the heteroaromatic ring is a 5 or 6 membered ring. In another embodiment, the heteroaromatic ring has from 1 to about 4 heteroatoms selected from oxygen, sulfur and nitrogen. Representative heteroaryls include pyridyl, furanyl, thiophenyl, pyrrolyl, oxazolyl, imidazolyl, indolizinyl, thiazolyl, isoxazolyl, pyrazolyl, isothiazolyl, pyridazinyl, pyrimidinyl, pyrazinyl, triazinyl, triazolyl, pyridinyl, thiadiazolyl, pyrazinyl, quinolyl, isoquinolinyl, indazolyl, benzoxazolyl, benzo[1,3]dioxolyl, benzofuryl, benzothiazolyl, imidazopyridinyl, isothiazolyl, tetrazolyl, benzimidazolyl, benzoxazolyl, benzothiazolyl, benzothiadiazolyl, benzoxadiazolyl, indolyl, tetrahydroindolyl, azaindolyl, imidazopyridyl, quinazolinyl, purinyl, [1,2,3]thiadiazolyl, 5,6,7,8-tetrahydroindolizinyl, imidazo[4,5-a]pyridyl, imidazo[1,2-a]pyridyl, imidazo[4,5-b]pyridyl, imidazo[4,5-c]pyridyl, pyrrolo[2,3]pyrimidyl, pyrazolo[3,4]pyrimidyl or benzo(b)thienyl and the like. These heteroaryl groups may be optionally substituted with one or more substituents including (but not limited to amino, alkylamino, alkoxy, alkylthio, oxo, halo, acyl, nitro, hydroxyl, cyano, aryl, alkylaryl, aryloxy, arylthio, arylamino, carbocyclyl, carbocyclyloxy, carbocyclylthio, carbocyclylamino, heterocyclyl, heterocyclyloxy, heterocyclylamino, heterocyclylthio, and the like. Particular heteroaryl substituents include halo, lower cyano, haloalkyl, lower alkoxy, lower alkyl, hydroxyl, amino, lower alkylsulfanyl, —C(O)O-(lower alkyl), —C(O)NH$_2$, —OC(O)-(lower alkyl), and —C(O)-(lower alkyl).

The term "heteroaralkyl" or "heteroarylalkyl," as used herein, refers to a heteroaryl group that is attached to another moiety via an alkylene linker. Heteroaralkyl groups can be substituted or unsubstituted.

As used herein, the term "halogen" or "halo" means —F, —Cl, —Br or —I.

As used herein, the term "haloalkyl" means an alkyl group in which one or more —H is replaced with a halo group. Examples of haloalkyl groups include —CF$_3$, —CHF$_2$, —CCl$_3$, —CH$_2$CH$_2$Br, —CH$_2$CH(CH$_2$CH$_2$Br)CH$_3$, —CHICH$_3$, and the like.

As used herein, the term "haloalkoxy" or "haloalkyloxy" means an alkoxy group in which one or more —H is replaced with a halo group. Examples of haloalkoxy groups include —OCF$_3$ and —OCHF$_2$.

As used herein, the term "alkoxycarbonyl" means a group having the formula —C(O)O-(alkyl). An example of an alkoxycarbonyl is t-butoxycarbonyl.

As used herein, the term "aralkoxycarbonyl" means a group having the formula —C(O)O-(aralkyl). An example of an aralkoxycarbonyl is benzyloxycarbonyl.

As used herein, the terms "subject", "patient" and "animal", are used interchangeably and include, but are not limited to, a cow, monkey, horse, sheep, pig, chicken, turkey, quail, cat, dog, mouse, rat, rabbit, guinea pig and human. The preferred subject, patient or animal is a human.

As used herein, the term "lower" refers to a group having up to four atoms. For example, a "lower alkyl" refers to an alkyl radical having from 1 to 4 carbon atoms, a "lower alkenyl" or "lower alkynyl" refers to an alkenyl or alkynyl radical having from 2 to 4 carbon atoms, and a lower alkoxy refers to an alkoxy having from 1 to 4 carbon atoms. Lower substituents are typically preferred.

Where a particular substituent occurs multiple times in a given structure or moiety, the identity of the substituent is independent in each case and may be the same as or different from other occurrences of that substituent in the structure or moiety. Furthermore, individual substituents in the specific embodiments and exemplary compounds of this invention are preferred in combination with other such substituents in the compounds of this invention, even if such individual substituents are not expressly noted as being preferred or not expressly shown in combination with other substituents.

The compounds of the invention are defined herein by their chemical structures and/or chemical names. Were a compound is referred to by both a chemical structure and a chemical name, and the chemical structure and chemical name conflict, the chemical structure is determinative of the compound's identity.

Suitable substituents for an alkyl, alkylene, alkenyl, alkynyl, cycloalkyl, cycloalkenyl, heterocyclyl, aryl, aralkyl, heteroaryl, and heteroaralkyl groups include any substituent which will form a stable compound of the invention. Examples of substituents for an alkyl, alkylene, alkenyl, alkynyl, cycloalkyl, cycloalkenyl, heterocyclyl, aryl, aralkyl, heteroaryl, and heteroarylalkyl include an alkyl, an alkenyl, an alkynyl, an cycloalkyl, an cycloalkenyl, an heterocyclyl, an aryl, an heteroaryl, an aralkyl, an heteraralkyl, a haloalkyl, —C(O)NR$_1$R$_2$, —NR$_4$C(O)R$_5$, halo, —OR$_4$, cyano, nitro, haloalkoxy, —C(O)R$_4$, —NR$_1$R$_2$, —C(O)OR$_4$, —OC(O)R$_4$, —NR$_4$C(O)NR$_1$R$_2$, —OC(O)NR$_1$R$_2$, —NR$_4$C(O)OR$_5$, —S(O)$_p$R$_4$, or —S(O)$_h$NR$_1$R$_2$, wherein R$_1$, R$_2$, R$_4$, R$_5$, h and p are as defined above.

In addition, alkyl, cycloalkyl, alkylene, a heterocyclyl, and any saturated portion of a alkenyl, cycloalkenyl, alkynyl, aralkyl, and heteroaralkyl groups, may also be substituted with =O, =S, =N—R$_4$.

When a heterocyclyl, heteroaryl, or heteroaralkyl group contains a nitrogen atom, it may be substituted or unsubstituted. When a nitrogen atom in the aromatic ring of a heteroaryl group has a substituent the nitrogen may be a quaternary nitrogen.

Choices and combinations of substituents and variables envisioned by this invention are only those that result in the formation of stable compounds. The term "stable", as used herein, refers to compounds which possess stability sufficient to allow manufacture and which maintains the integrity of the compound for a sufficient period of time to be useful for the purposes detailed herein (e.g., therapeutic or prophylactic administration to a subject). Typically, such compounds are stable at a temperature of 40° C. or less, in the absence of excessive moisture, for at least one week. Such choices and combinations will be apparent to those of ordinary skill in the art and may be determined without undue experimentation.

Unless indicated otherwise, the compounds of the invention containing reactive functional groups (such as (without limitation) carboxy, hydroxy, and amino moieties) also include protected derivatives thereof. "Protected derivatives" are those compounds in which a reactive site or sites are blocked with one or more protecting groups. Suitable protecting groups for carboxy moieties include benzyl, tert-butyl, and the like. Suitable protecting groups for amino and amido groups include acetyl, tert-butoxycarbonyl, benzyloxycarbonyl, and the like. Suitable protecting groups for hydroxy include benzyl, methoxymethyl and the like. Other suitable protecting groups are well known to those of ordinary skill in the art and include those found in T. W. Greene, Protecting Groups in Organic Synthesis, John Wiley & Sons, Inc. 1981, the entire teachings of which are incorporated herein by reference.

As used herein, the term "compound(s) of this invention" and similar terms refers to a compound of any one of formulas (I) through (XVII), Table 1 or a pharmaceutically acceptable salt, solvate, clathrate, or prodrug thereof and also include protected derivatives thereof.

As used herein and unless otherwise indicated, the term "prodrug" means a derivative of a compound that can hydrolyze, oxidize, or otherwise react under biological conditions (in vitro or in vivo) to provide a compound of this invention. Prodrugs may only become active upon such reaction under biological conditions, but they may have activity in their unreacted forms. Examples of prodrugs contemplated in this invention include, but are not limited to, analogs or derivatives of compounds of any one of formulas (I) through (XVII), or Table 1 that comprise biohydrolyzable moieties such as biohydrolyzable amides, biohydrolyzable esters, biohydrolyzable carbamates, biohydrolyzable carbonates, biohydrolyzable ureides, and biohydrolyzable phosphate analogues. Other examples of prodrugs include derivatives of compounds of any one of formulas (I) through (XVII), or Table 1 that comprise —NO, —NO$_2$, —ONO, or —ONO$_2$ moieties.

Prodrugs can typically be prepared using well-known methods, such as those described by 1 BURGER'S MEDICINAL CHEMISTRY AND DRUG DISCOVERY (1995) 172-178, 949-982 (Manfred E. Wolff ed., 5$^{th}$ ed), the entire teachings of which are incorporated herein by reference.

As used herein and unless otherwise indicated, the terms "biohydrolyzable amide", "biohydrolyzable ester", "biohydrolyzable carbamate", "biohydrolyzable carbonate", "biohydrolyzable ureide" and "biohydrolyzable phosphate analogue" mean an amide, ester, carbamate, carbonate, ureide, or phosphate analogue, respectively, that either: 1) does not destroy the biological activity of the compound and confers upon that compound advantageous properties in vivo, such as uptake, duration of action, or onset of action; or 2) is itself biologically inactive but is converted in vivo to a biologically active compound. Examples of biohydrolyzable amides include, but are not limited to, lower alkyl amides, α-amino acid amides, alkoxyacyl amides, and alkylaminoalkylcarbonyl amides. Examples of biohydrolyzable esters include, but are not limited to, lower alkyl esters, alkoxyacyloxy esters, alkyl acylamino alkyl esters, and choline esters. Examples of biohydrolyzable carbamates include, but are not limited to, lower alkylamines, substituted ethylenediamines, aminoacids, hydroxyalkylamines, heterocyclic and heteroaromatic amines, and polyether amines.

As used herein, the term "pharmaceutically acceptable salt," is a salt formed from an acid and a basic group of one of the compounds of any one of formulas (I) through (XVII) or Table 1. Illustrative salts include, but are not limited, to sulfate, citrate, acetate, oxalate, chloride, bromide, iodide, nitrate, bisulfate, phosphate, acid phosphate, isonicotinate, lactate, salicylate, acid citrate, tartrate, oleate, tannate, pantothenate, bitartrate, ascorbate, succinate, maleate, gentisinate, fumarate, gluconate, glucaronate, saccharate, formate, benzoate, glutamate, methanesulfonate, ethanesulfonate; benzenesulfonate, p-toluenesulfonate; and pamoate 1,1'-methylene-bis-(2-hydroxy-3-naphthoate)) salts. The term "pharmaceutically acceptable salt" also refers to a salt prepared from a compound of any one of formulas (I) through (XVII) or Table 1 having an acidic functional group, such as a carboxylic acid functional group, and a pharmaceutically, acceptable inorganic or organic base. Suitable bases include, but are not limited to, hydroxides of alkali metals such as sodium, potassium, and lithium; hydroxides of alkaline earth metal such as calcium and magnesium; hydroxides of other metals, such as aluminum and zinc; ammonia, and organic amines, such as unsubstituted or hydroxy-substituted mono-, di-, or trialkylamines; dicyclohexylamine; tributyl amine; pyridine; N-methyl-N-ethylamine; diethylamine; triethylamine; mono-, bis-, or tris-(2-hydroxy-lower alkyl amines), such as mono-, bis-, or tris-(2-hydroxyethyl)amine, 2-hydroxy-tert-butylamine, or tris-(hydroxymethyl)methylamine, N,N,-di-lower alkyl-N-(hydroxy lower alkyl)-amines, such as N,N-dimethyl-N-(2-hydroxyethyl)amine, or tri-(2-hydroxyethyl)amine; N-methyl-D-glucamine; and amino acids such as arginine, lysine, and the like.

As used herein, the term "pharmaceutically acceptable solvate," is a solvate formed from the association of one or more solvent molecules to one or more molecules of a compound of any one of formulas (I) through (XVII) or Table 1. The term solvate includes hydrates (e.g., hemi-hydrate, mono-hydrate, dihydrate, trihydrate, tetrahydrate, and the like).

As used herein, the term "clathrate" means a compound of the present invention or a salt thereof in the form of a crystal lattice that contains spaces (e.g., channels) that have a guest molecule (e.g., a solvent or water) trapped within.

As used herein, the term "asthma" means a pulmonary disease, disorder or condition characterized by reversible airway obstruction, airway inflammation, and increased airway responsiveness to a variety of stimuli.

"Immunosuppression" refers to impairment of any component of the immune system resulting in decreased immune function. This impairment may be measured by any conventional means including whole blood assays of lymphocyte function, detection of lymphocyte proliferation and assessment of the expression of T cell surface antigens. The antisheep red blood cell (SRBC) primary (IgM) antibody response assay (usually referred to as the plaque assay) is one specific method. This and other methods are described in Luster, M. I., Portier, C., Pait, D. G., White, K. L., Jr., Gennings, C., Munson, A. E., and Rosenthal, G. J. (1992). "Risk Assessment in Immunotoxicology I: Sensitivity and Predictability of Immune Tests." Fundam. Appl. Toxicol., 18, 200-210. Measuring the immune response to a T-cell dependent immunogen is another particularly useful assay (Dean, J. H., House, R. V., and Luster, M. I. (2001). "Immunotoxicology: Effects of, and Responses to, Drugs and Chemicals." In Principles and Methods of Toxicology: Fourth Edition (A. W. Hayes, Ed.), pp. 1415-1450, Taylor & Francis, Philadelphia, Pa.). Subjects in need of immunosuppression include subjects who are about to undergo or have undergone organ transplantation, including kidney, heart, lung, liver, intestines, bone marrow, skin grafts and transplantation of islets of Langerhans, or subjects that have immune, inflammatory or allergic disorders.

The compounds of this invention can be used to treat subjects with immune disorders. As used herein, the term "immune disorder" and like terms means a disease, disorder or condition caused by the immune system of an animal, including autoimmune disorders. Immune disorders include those diseases, disorders or conditions that have an immune component and those that rare substantially or entirely immune system-mediated. Autoimmune disorders are those wherein the animal's own immune system mistakenly attacks itself, thereby targeting the cells, tissues, and/or organs of the animal's own body. For example, the autoimmune reaction is directed against the brain in multiple sclerosis and the gut in Crohn's disease in other autoimmune disorders such as systemic lupus erythematosus (lupus), affected tissues and organs may vary among individuals with the same disease. One person with lupus may have affected skin and joints whereas another may have affected skin, kidney, and lungs. Ultimately, damage to certain tissues by the immune system may be permanent, as with destruction of insulin-producing cells of the pancreas in Type 1 diabetes mellitus. Specific autoimmune disorders that may be ameliorated using the compounds and methods of this invention include without limitation, autoimmune disorders of the nervous system (e.g., multiple sclerosis, myasthenia gravis, autoimmune neuropathies such as Guillain-Barré, and autoimmune uveitis), autoimmune disorders of the blood (e.g., autoimmune hemolytic anemia, pernicious anemia, and autoimmune thrombocytopenia), autoimmune disorders of the blood vessels (e.g., temporal arteritis, anti-phospholipid syndrome, vasculitides such as Wegener's granulomatosis, and Behcet's disease), autoimmune disorders of the skin (e.g., psoriasis, dermatitis herpetiformis, pemphigus vulgaris, and vitiligo), autoimmune disorders of the gastrointestinal system (e.g., Crohn's disease, ulcerative colitis, primary biliary cirrhosis, and autoimmune hepatitis), autoimmune disorders of the endocrine glands (e.g., Type 1 or immune-mediated diabetes mellitus, Grave's disease. Hashimoto's thyroiditis, autoimmune oophoritis and orchitis, and autoimmune disorder of the adrenal gland); and autoimmune disorders of multiple organs (including connective tissue and musculoskeletal system diseases) (e.g., rheumatoid arthritis, systemic lupus erythematosus, scleroderma, polymyositis, dermatomyositis, spondyloarthropathies such as ankylosing spondylitis, and Sjogren's syndrome). In addition, other immune system mediated diseases, such as graft-versus-host disease and allergic disorders, are also included, in the definition of immune, disorders herein. Because a number of immune disorders are caused by inflammation, there is some overlap between disorders that are considered immune disorders and inflammatory disorders. For the purpose of this invention, in the case of such an overlapping disorder, it may be considered either an immune disorder or an inflammatory disorder. "Treatment of an immune disorder" herein refers to administering a compound or a composition of the invention to a subject, who has an immune disorder, a symptom of such a disease or a predisposition towards such a disease, with the purpose to cure, relieve, alter, affect, or prevent the autoimmune disorder, the symptom of it, or the predisposition towards it.

As used herein, the term "allergic disorder" means a disease, condition or disorder associated with an allergic response against normally innocuous substances. These substances may be found in the environment (such as indoor air pollutants and aeroallergens) or they may be non-environmental (such as those causing dermatological or food allergies). Allergens can enter the body through a number of routes, including by inhalation, ingestion, contact with the skin or injection (including by insect sting). Many allergic disorders are linked to atopy, a predisposition to generate the allergic antibody IgE. Because IgE is able to sensitize mast cells anywhere in the body, atopic individuals often express disease in more than one organ. For the purpose of this invention, allergic disorders include any hypersensitivity that occurs upon re-exposure to the sensitizing allergen, which in turn causes the release of inflammatory mediators. Allergic disorders include without limitation, allergic rhinitis (e.g., hay fever), sinusitis, rhinosinusitis, chronic or recurrent otitis media, drug reactions, insect sting reactions, latex reactions, conjunctivitis, urticaria, anaphylaxis and anaphylactoid reactions, atopic dermatitis, asthma and food allergies.

The compounds of this invention can be used to prevent or to treat subjects with inflammatory disorders. As used herein, an "inflammatory disorder" means a disease, disorder or condition characterized by inflammation of body tissue or having an inflammatory component. These include local inflammatory responses and systemic inflammation. Examples, of such inflammatory disorders include: transplant rejection; chronic inflammatory disorders of the joints, including arthritis, rheumatoid arthritis, osteoarthritis and bone diseases associated with increased bone resorption; inflammatory bowel diseases such as ileitis, ulcerative colitis, Barrett's syndrome, and Crohn's disease; inflammatory lung disorders such as asthma, adult respiratory distress syndrome, and chronic obstructive airway disease; inflammatory disorders of the eye including corneal dystrophy, trachoma, onchocerciasis, uveitis, sympathetic ophthalmitis and endophthalmitis; chronic inflammatory disorders of the gums, including gingivitis and periodontitis; tuberculosis; leprosy; inflammatory diseases of the kidney including uremic complications, glomerulonephritis and nephrosis; inflammatory disorders of the skin including sclerodermatitis, psoriasis and eczema; inflammatory diseases of the central nervous system, including chronic demyelinating diseases of the nervous system, multiple sclerosis, AIDS-related neurodegeneration and Alzheimer's disease, infectious meningitis, encephalomyelitis, Parkinson's disease, Huntington's disease, amyotrophic lateral sclerosis and viral or autoimmune encephalitis; autoimmune disorders, immune-complex vasculitis, systemic lupus and erythematodes; systemic lupus erythematosus (SLE); and inflammatory diseases of the heart such as cardiomyopathy, ischemic heart disease hypercholesterolemia, atherosclerosis); as well as various other diseases with significant inflammatory components, including preeclampsia; chronic liver failure, brain and spinal cord trauma, cancer). There may also be a systemic inflammation of the body, exemplified by gram-positive or gram negative shock, hemorrhagic or anaphylactic shock, or shock induced by cancer chemotherapy in response to pro-inflammatory cytokines, e.g., shock associated with pro-inflammatory cytokines. Such shock can be induced, e.g., by a chemotherapeutic agent used in cancer chemotherapy. "Treatment of an inflammatory disorder" herein refers to administering a compound or a composition of the invention to a subject, who has an inflammatory disorder, a symptom of such a disorder or a predisposition towards such a disorder, with the purpose to cure, relieve, alter, affect, or prevent the inflammatory disorder, the symptom of it, or the predisposition towards it.

An "effective amount" is the quantity of compound in which a beneficial outcome is achieved when the compound is administered to a subject or alternatively, the quantity of compound that possess a desired activity in-vivo or in-vitro. In the case of inflammatory disorders, allergic disorders and autoimmune disorders, a beneficial clinical outcome includes reduction in the extent or severity of the symptoms associated with the disease or disorder and/or an increase in the longevity and/or quality of life of the subject compared with the absence of the treatment. The precise amount of compound administered to a subject will depend on the type and severity of the disease or condition and on the characteristics of the subject, such as general health, age, sex, body weight and tolerance to drugs. It will also depend on the degree, severity and type of inflammatory disorder or autoimmune disorder, allergic disorders, or the degree of immunosuppression sought. The skilled artisan will be able to determine appropriate dosages depending on these and other factors.

The compounds of the invention may contain one or more chiral centers and/or double bonds and, therefore, exist as stereoisomers, such as double-bond isomers (i.e., geometric isomers), enantiomers, or diastereomers. According to this invention, the chemical structures depicted herein, including the compounds of this invention, encompass all of the corresponding compounds' geometric isomers, enantiomers and stereoisomers, that is, both the stereomerically pure form (e.g., geometrically pure, enantiomerically pure, or diastereomerically pure) and enantiomeric, diastereomeric, and geometric isomeric mixtures. In some cases, one enantiomer, diastereomer, or geometric isomer will possess superior activity or an improved toxicity or kinetic profile compared to others. In those cases, such enantiomers, diastereomers, and geometric isomers of a compound of this invention is preferred.

The term "inhibit production of IL-2" and like terms means inhibiting IL-2 synthesis (e.g. by inhibiting transcription (mRNA expression), or translation (protein expression)) and/or inhibiting IL-2 secretion in a cell that has the ability to produce and/or secrete IL-2 (e.g., T lymphocyte). Likewise, the term "inhibiting production of IL-2, IL-4, IL-5, IL-13, GM-CSF, TNF-α or INF-γ means inhibiting the synthesis (e.g. by inhibiting transcription, or translation) and/or inhibiting the secretion in a cell that has the ability to produce and/or secrete these cytokines.

As used herein, a composition that "substantially" comprises a compound means that the composition contains more than about 80% by weight, more preferably more than about 90% by weight, even more preferably more than about 95% by weight, and most preferably more than about 97% by weight of the compound.

As used herein, a composition that is "substantially free" of a compound means that the composition contains less than about 20%® by weight, more preferably less than about 10% by weight, even more preferably less than about 5% by weight, and most preferably less than about 3% by weight of the compound.

As used herein, a reaction that is "substantially complete" means that the reaction contains more than about 80% by weight of the desired product, more preferably more than about 90% by weight of the desired product, even more preferably more than about 95% by weight of the desired product, and most preferably more than about 97% by weight of the desired product.

As used herein, a racemic mixture means about 50% of one enantiomer and about 50% of is corresponding enantiomer relative to all chiral centers in the molecule. The invention encompasses all enantiomerically-pure, enantiomerically-enriched, diastereomerically pure, diastereomerically enriched, and racemic mixtures of the compounds of any one of formulas (I) through (XVII) or Table 1.

Enantiomeric and diastereomeric mixtures can be resolved into their component enantiomers or stereoisomers by well known methods, such as chiral-phase gas chromatography, chiral-phase high performance liquid chromatography, crystallizing the compound as a chiral salt complex, or crystallizing the compound in a chiral solvent. Enantiomers and diastereomers can also be obtained from diastereomerically- or enantiomerically-pure intermediates, reagents, and catalysts by well known asymmetric synthetic methods.

When administered to a patient, e.g., to a non-human animal for veterinary use or for improvement of livestock, or to a human for clinical use, the compounds of the invention are typically administered in isolated form or as the isolated form in a pharmaceutical composition. As used herein, "isolated" means that the compounds of the invention are separated from other components of either (a) a natural source, such as a plant or cell, preferably bacterial culture, or (b) a synthetic organic chemical reaction mixture. Preferably, via conventional techniques, the compounds of the invention are purified. As used herein, "purified" means that when isolated, the isolate contains at least 95%, preferably at least 98%, of a single compound of the invention by weight of the isolate.

Only those choices and combinations of substituents that result in a stable structure are contemplated. Such choices and, combinations will be apparent to those of ordinary skill in the art and may be determined without undue experimentation.

The invention can be understood more fully by reference to the following detailed description and illustrative examples, which are intended to exemplify non-limiting embodiments of the invention.

Specific Embodiments

The invention relates to compounds and pharmaceutical compositions that are particularly useful for immunosuppression or to treat or prevent inflammatory conditions and immune disorders.

One embodiment of the invention relates to compounds of formula (I):

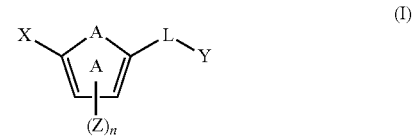

or a pharmaceutically acceptable salt, solvate, clathrate, or prodrug thereof, wherein:

X is an optionally substituted benzoimidazolyl, an optionally substituted 5,6,7,8-tetrahydroindolizinyl, an optionally substituted imidazo[4,5-a]pyridyl, an optionally substituted imidazo[1,2-a]pyridyl, an optionally substituted imidazo[4,5-b]pyridyl, or an optionally substituted imidazo[4,5-c]pyridyl;

Y is an unsubstituted alkyl, an optionally substituted alkenyl, an optionally, substituted cycloalkyl, an optionally substituted cycloalkenyl, an optionally substituted aryl, an optionally substituted heteroaryl, or an optionally substituted heteroaralkyl;

A is —O—, —S(O)$_p$—, —NH—, —NZ—, —CH=CH—, —CZ=CH—, —CH=CZ—, —CZ=CZ—, —N=CH—, —N=CZ—, —CH=N—, —CZ=N—, or an N-oxide of —N=CH—, —N=CZ—, —CH=N—, or —CZ=N—;

Z, for each occurrence, is independently selected from the group consisting of an optionally substituted alkyl, an optionally substituted alkenyl, an optionally substituted alkynyl, an optionally substituted cycloalkyl, an optionally substituted cycloalkenyl, an optionally substituted heterocyclyl, an optionally substituted aryl, an optionally substituted heteroaryl, an optionally substituted aralkyl, an optionally substituted heteraralkyl, a haloalkyl, —C(O)NR$_1$R$_2$, —NR$_4$C(O)R$_5$, halo, —OR$_4$, cyano, nitro, haloalkoxy, —C(O)R$_4$, —NR$_1$R$_2$, —C(O)OR$_4$, —OC(O)R$_4$, —NR$_4$C(O)NR$_1$R$_2$, —OC(O)NR$_1$R$_2$, —NR$_4$C(O)OR$_5$, —S(O)$_p$R$_4$, or —S(O)$_h$NR$_1$R$_2$;

L is a linker selected from the group consisting of an optionally substituted lower alkyl, and optionally substituted lower alkenyl, —NRCR$_4$R$_5$—, —C(O)—, —OC(O)—, —C(O)O—, —NR—C(O)—, —C(O)—NR—, —NR—C(O)—NR—, —C(S)—, —NR—S(O)$_h$—, —S(O)$_h$—NR—, —NR—C(=NR)—, —NR—C(=NR)—NR—, —NR—C(=N—CN)—NR—, —NR—C(=N—NO$_2$)—NR—, —NR—C(S)—, —C(S)—NR—, or —NR—C(S)—NR—;

R, for each occurrence, is independently selected from —H, an alkyl, acetyl, alkoxycarbonyl, or aralkoxycarbonyl;

R$_1$ and R$_2$, for each occurrence are, independently, H, an optionally substituted alkyl; an optionally substituted alkenyl, an optionally substituted alkynyl, an optionally substituted cycloalkyl, an optionally substituted cycloalkenyl, an optionally substituted heterocyclyl, an optionally substituted aryl, an optionally substituted heteroaryl, an optionally substituted aralkyl, or an optionally substituted heteraralkyl; or R$_1$ and R$_2$ taken together with the nitrogen to which they are attached is optionally substituted heterocyclyl or optionally substituted heteroaryl;

R$_4$ and R$_5$ for each occurrence are, independently, H, an optionally substituted alkyl, an optionally substituted alkenyl, an optionally substituted alkynyl, an optionally substituted cycloalkyl, an optionally substituted cycloalkenyl, an optionally substituted heterocyclyl, an optionally substituted aryl, an optionally substituted heteroaryl, an optionally substituted aralkyl, or an optionally substituted heteraralkyl;

h is 1 or 2;

n is 0 or an integer from 1 to 4; and p, for each occurrence, is, independently, 0, 1, or 2.

In another embodiment, the invention relates to compounds represented by formula (II):

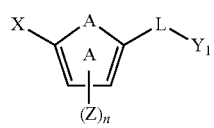

(II)

or a pharmaceutically acceptable salt, solvate, clathrate, or prodrug thereof wherein:

Y$_1$ is an alkyl, a heterocyclyl, or an aralkyl, wherein the alkyl, heterocyclyl or aralkyl is optionally substituted with one or more substituent selected from the group consisting of an alkyl, an alkynyl, an cycloalkyl, an cycloalkenyl, an heterocyclyl, an aryl, an heteraralkyl, a haloalkyl, —C(O)NH$_2$, —NR$_4$C(O)R$_5$, halo, —OR$_4$, cyano, nitro, haloalkoxy, —C(O)R$_4$, —NR$_1$R$_2$, —SR, —C(O)OH, —OC(O)R$_4$, —NR$_4$C(O)NR$_1$R$_2$, —OC(O)NR$_1$R$_2$, —NR$_4$C(O)OR$_5$, —S(O)R$_4$, or —S(O)$_h$NR$_1$R$_2$; and X, R$_1$, R$_2$, R$_4$, R$_5$, A, L, Z, h, n and p are defined as for formula (I).

In another embodiment, the invention relates to compounds represented by formula (III):

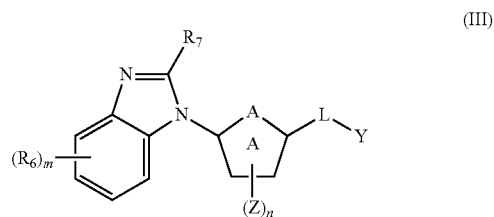

(III)

or a pharmaceutically acceptable salt, solvate, clathrate, or prodrug thereof wherein:

R$_6$, for each occurrence, and R$_7$ are, independently, selected from the group consisting of an optionally substituted alkyl, an optionally substituted alkenyl, an optionally substituted alkynyl, an optionally substituted cycloalkyl, an optionally substituted cycloalkenyl, an optionally substituted heterocyclyl, an optionally substituted aryl, an optionally substituted heteroaryl, an optionally substituted aralkyl, an optionally substituted heteraralkyl, a haloalkyl, —C(O)NR$_1$R$_2$, —NR$_4$C(O)R$_5$, halo, —OR$_4$, cyano, nitro, haloalkoxy, —C(O)R$_4$, —NR$_1$R$_2$, —C(O)OR$_4$, —OC(O)R$_4$, —NR$_4$C(O)NR$_1$R$_2$, —OC(O)NR$_1$R$_2$, —NR$_4$C(O)OR$_5$, —S(O)$_p$R$_4$, or —S(O)$_h$NR$_1$R$_2$;

m is 0 or an integer from 1 to 4; and

Y, R$_1$, R$_2$, R$_4$, R$_5$, A, L, Z, h, n and p are defined as for formula (I).

In another embodiment, the invention relates to compounds represented by formula (XII)

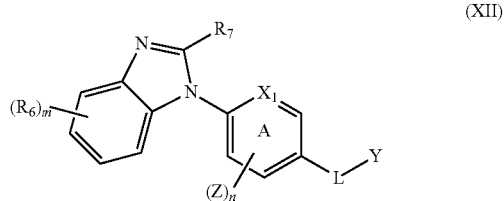

(XII)

or a pharmaceutically acceptable salt, solvate, clathrate, or prodrug thereof wherein X$_1$ is N, CH or CZ; Y, L, Z, and n are defined as for formula (I); and R$_6$, R$_7$ and m are defined as in formula (III).

In another embodiment, the invention relates to compounds represented by formula (VII):

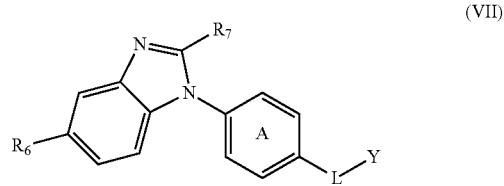

(VII)

or a pharmaceutically acceptable salt, solvate, clathrate, or prodrug thereof wherein Y and L are defined as for formula (I); and R$_6$ and R$_7$ are defined as for formula (III).

In another embodiment, the invention relates to compounds represented by formula (VIII):

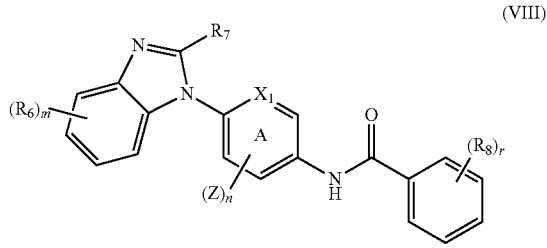

(VIII)

or a pharmaceutically acceptable salt, solvate, clathrate, or prodrug thereof wherein:
$R_8$, for each occurrence, is, independently, selected from the group consisting of an optionally substituted alkyl, an optionally substituted alkenyl, an optionally substituted alkynyl, an optionally substituted cycloalkyl, an optionally substituted cycloalkenyl, an optionally substituted heterocyclyl, an optionally substituted aryl, an optionally substituted heteroaryl, an optionally substituted aralkyl, an optionally substituted heteraralkyl, a haloalkyl, —C(O)NR$_1$R$_2$, —NR$_4$C(O)R$_5$, halo, —OR$_1$, cyano, nitro, haloalkoxy, —C(O)R$_4$, —NR$_1$R$_2$, —C(O)OR$_4$, —OC(O)R$_4$, —NR$_4$C(O)NR$_1$R$_2$, —OC(O)NR$_1$R$_2$, —NR$_4$C(O)OR$_5$, —S(O)$_p$R$_4$, or —S(O)$_h$NR$_1$R$_2$; and
r is 0 or an integer from 1 to 5;
Z, R$_1$, R$_2$, R$_4$, R$_5$, h, n, and p are defined as for formula (I); R$_6$, R$_7$ and m are defined as for formula (III); and X$_1$ is defined as in formula (XII).

In another embodiment, the invention relates to compounds represented by formula (IX):

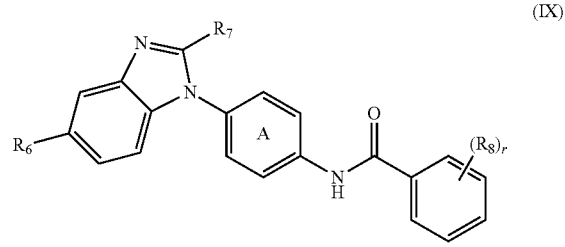

(IX)

or a pharmaceutically acceptable salt, solvate, clathrate, or prodrug thereof wherein R$_6$, and R$_7$ are defined as for formula (III); and R$_8$ and r are defined as in formula (VIII).

In another embodiment, the invention relates to compounds represented by formula (XVI):

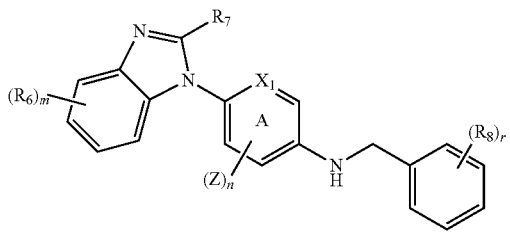

(XVI)

or a pharmaceutically acceptable salt, solvate, clathrate, or prodrug thereof wherein Z and n are defined as for formula (I); R$_6$, R$_7$ and m are defined as for formula (III); X$_1$ is defined as in formula (XII); and R$_8$ and r are defined as in formula (VIII).

In another embodiment, the invention relates to compounds represented by formula (XVII):

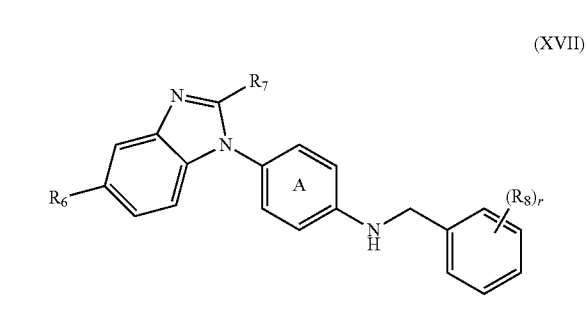

(XVII)

or a pharmaceutically acceptable salt, solvate, clathrate, or prodrug thereof wherein R$_6$, R$_7$ and m are defined as for formula (III); and R$_8$ and r are defined as in formula (VIII).

In another embodiment, the invention relates to compounds represented by formula (IV):

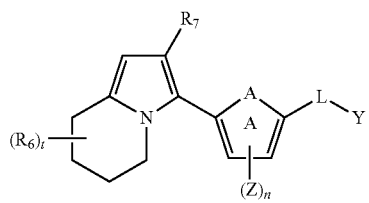

or a pharmaceutically acceptable salt, solvate, clathrate, or prodrug thereof wherein t is 0 or an integer from 1 to 8; A, Z, and n are defined as for formula (I); and R$_6$ and R$_7$ are defined as for formula (III).

In another embodiment, the invention relates to compounds represented by formula (XIII):

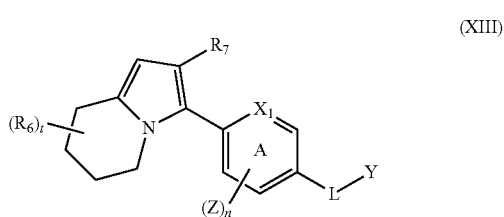

(XIII)

or a pharmaceutically acceptable salt, solvate, clathrate, or prodrug thereof wherein Y, L, Z, and n are defined as for formula (I); R$_6$ and R$_7$ are defined as in formula (III); X$_1$ is defined as in formula (XII); and t is defined as in formula (IV).

In another embodiment, the invention relates to compounds represented by formula (X):

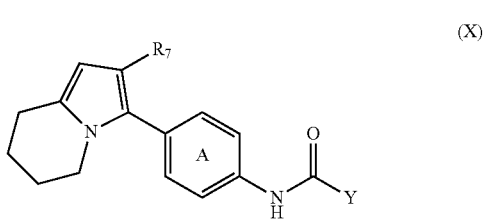

(X)

or a pharmaceutically acceptable salt, solvate, clathrate, or prodrug thereof wherein Y is defined as for formula (I); and R₇ is defined as for formula (III).

In another embodiment, the invention relates to compounds represented by formula (V):

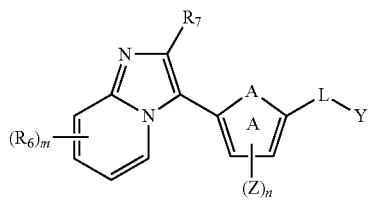

(V)

or a pharmaceutically acceptable salt, solvate, clathrate, or prodrug thereof wherein Y, L, A, Z, and n are defined as in formula (I); and R₆, R₇ and m are defined as in formula (III).

In another embodiment, the invention relates to compounds represented by formula (XIV):

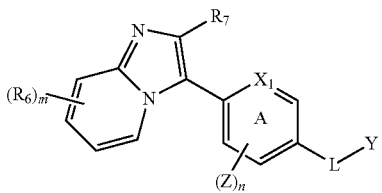

(XIV)

or a pharmaceutically acceptable salt, solvate, clathrate, or prodrug thereof wherein Y, L, Z, and n are defined as in formula (I); R₆, R₇, and m are defined as for formula (III); and X₁ is defined as in formula (XII).

In one embodiment, the invention relates to compounds represented by formula (XI):

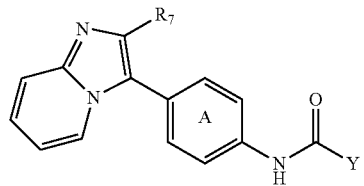

(XI)

or a pharmaceutically acceptable salt, solvate, clathrate, or prodrug thereof wherein Y is defined as in formula (I); and R₇ is defined as in formula (III).

In another embodiment, the invention relates to compounds represented by formula (VI):

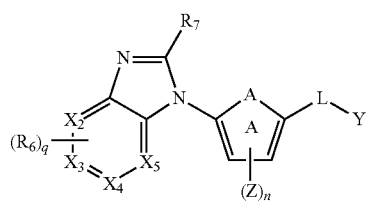

(VI)

or a pharmaceutically acceptable salt, solvate, clathrate, or prodrug thereof wherein:
one of X₂, X₃, X₄, or X₅ is N and the others are, independently, CH or CR₆;
q is 0 or an integer from 1 to 3;
Y, L, A, Z, and n are defined as in formula (I); and R₆ and R₇ are defined as in formula (III).

In another embodiment, the invention relates to compounds represented by formula (XV):

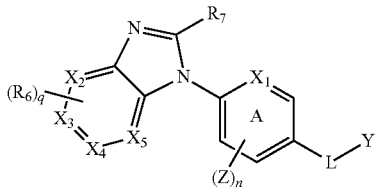

(XV)

or a pharmaceutically acceptable salt, solvate, clathrate, or prodrug thereof wherein Y, L, Z, and n are defined as for formula (I); R₆ and R₇ are defined as for formula (III); X₁ is defined as for formula (XII); and X₂, X₃, X₄, X₅ and q are defined as for formula (VI).

In another embodiment, the invention relates to compounds selected from the group consisting of:
2,3,6-Trifluoro-N-[4-(2-trifluoromethyl-5-methoxy-benzoimidazol-1-yl)-phenyl]-benzamide;
2,3,5-Trifluoro-N-[4-(2-trifluoromethyl-5-methoxy-benzoimidazol-1-yl)-phenyl]-benzamide;
2,3,4-Trifluoro-N-[4-(2-trifluoromethyl-5-methoxy-benzoimidazol-1-yl)-phenyl]-benzamide;
2,3-Difluoro-N-[4-(2-trifluoromethyl-5-methoxy-benzoimidazol-1-yl)-phenyl]-benzamide;
3-Methyl-N-[4-(2-trifluoromethyl-5-methoxy-benzoimidazol-1-yl)-phenyl]-isonicotinamide;
3-Fluoro-N-[4-(2-trifluoromethyl-5-methoxy-benzoimidazol-1-yl)-phenyl]-isonicotinamide;
2,4-Dichloro-5-fluoro-N-[4-(2-trifluoromethyl-5-methoxy-benzoimidazol-1-yl)-phenyl]-benzamide,
2,3-Difluoro-N-[4-(2-trifluoromethyl-5,6,7,8-tetrahydroindolizin-3-yl)-phenyl]-benzamide;
2,4-Difluoro-N-[4-(2-trifluoromethyl-benzoimidazol-1-yl)-phenyl]-benzamide;
3-Nitro-N-[4-(2-trifluoromethyl-5-methoxy-benzoimidazol-1-yl)-phenyl]-benzamide;
2,3-Difluoro-N-[4-(2-methylsulfanyl-benzoimidazol-1-yl)-phenyl]-benzamide;
2,3-Difluoro-N-[4-(2-trifluoromethyl-benzoimidazol-1-yl)-phenyl]-thiobenzamide;
2,3-Dichloro-N-[4-(2-trifluoromethyl-benzoimidazol-1-yl)-phenyl]-benzamide;
2,3-Difluoro-N-[4-(2-trifluoromethyl-6-methoxy-benzoimidazol-1-yl)-phenyl]-benzamide;
2-Fluoro-2-chloro-N-[4-(2-trifluoromethyl-benzoimidazol-1-yl)-phenyl]-benzamide;
2,3,6-Trifluoro-5-amino-N-[4-(2-trifluoromethyl-benzoimidazol-1-yl)-phenyl]-benzamide;
2,3-Difluoro-N-[3-methyl-4-(2-trifluoromethyl-benzoimidazol-1-yl)-phenyl]-benzamide;
2-Methyl-N-[4-(2-trifluoromethyl-5,6,7,8-tetrahydroindolizin-3-yl)-phenyl]-benzamide;
2,3-Difluoro-N-[4-(2-trifluoromethyl-5,6,7,8-tetrahydroindolizin-3-yl)-phenyl]-benzamide;

2,3-Difluoro-N-[4-(2-trifluoromethyl-6-cyano-benzoimidazol-1-yl)-phenyl]-benzamide;
2,3-Difluoro-N-[4-(2-trifluoromethyl-4-amino-benzoimidazol-1-yl)-phenyl]-benzamide;
N-(3-{N-[4-(2-trifluoromethyl-benzoimidazol-1-yl)-phenyl]-carbamoyl}-2,4,5-trifluoro-phenyl)-carbamic acid t-butyl ester;
2,3-Difluoro-N-[4-(2-chloro-benzoimidazol-1-yl)-phenyl]-benzamide;
4-Methyl-[1,2,3]thiadiazole-5-carboxylic acid {N-[4-(2-chloro-5,6,7,8-tetrahydroindolizin-3-yl)-phenyl]}amide;
2,3-Difluoro-N-[2-chloro-4-(2-trifluoromethyl-benzoimidazol-1-yl)-phenyl]-benzamide;
2,5-Difluoro-N-[4-(2-trifluoromethyl-benzoimidazol-1-yl)-phenyl]-benzamide;
3-Fluoro-N-[4-(2-trifluoromethyl-benzoimidazol-1-yl)-phenyl]-isonicotinamide;
2,3-Difluoro-N-[4-(2-bromo-benzoimidazol-1-yl)-phenyl]-benzamide;
4-Methyl-[1,2,3]thiadiazole-5-carboxylic acid {N-[4-(2-trifluoromethyl-benzoimidazol-1-yl)-phenyl]}amide;
2,3-Difluoro-N-[3-trifluoromethyl-4-(2-trifluoromethyl-benzoimidazol-1-yl)-phenyl]-benzamide;
N-(4-{N-[4-(2-trifluoromethyl-benzoimidazol-1-yl)-phenyl]-carbamoyl}-2,3-difluoro-phenyl)-carbamic acid t-butyl ester;
2,3-Difluoro-N-[4-(2-trifluoromethyl-5,6-dimethoxy-benzoimidazol-1-yl)-phenyl]-benzamide;
2,3-Difluoro-N-[4-(2-iodo-benzoimidazol-1-yl)-phenyl]-benzamide;
N'-[2-(2-trifluoromethyl-benzoimidazol-1-yl)-pyrid-5-yl]-N-(2,5-difluoro-phenyl)-thiourea;
2,3-Difluoro-N-[4-(2-trifluoromethyl-5-tert-butyl-benzoimidazol-1-yl)-phenyl]-benzamide;
2,3-Difluoro-N-[2-(2-trifluoromethyl-benzoimidazol-1-yl)-pyrid-3-yl]-benzamide;
2,3-Difluoro-N-[3-cyano-4-(2-trifluoromethyl-benzoimidazol-1-yl)-phenyl]-benzamide;
2,5-Difluoro-N-[3-chloro-4-(2-trifluoromethyl-benzoimidazol-1-yl)-phenyl]-benzamide;
2,3-Difluoro-N-[4-(2-trifluoromethyl-5-amino-benzoimidazol-1-yl)-phenyl]-benzamide;
2,3-Difluoro-N-[4-(2-methanesulfinyl-benzoimidazol-1-yl)-phenyl]-benzamide;
2,5-Difluoro-N-[2-(2-trifluoromethyl-benzoimidazol-1-yl)-pyrid-5-yl]-benzamide;
2,3-Difluoro-N-[4-(2-trifluoromethyl-5,6-dimethyl-benzoimidazol-1-yl)-phenyl]-benzamide;
2,3-Difluoro-4-amino-N-[4-(2-trifluoromethyl-benzoimidazol-1-yl)-phenyl]-benzamide;
2,3-Difluoro-N-[4-(2-trifluoromethyl-imidazo[4,5-b]pyrid-3-yl)-phenyl]-benzamide;
N-[4-(2-trifluoromethyl-benzoimidazol-1-yl)-phenyl]-nicotinamide;
N-(2,3-difluorophenyl)-4-(2-trifluoromethyl-benzoimidazol-1-yl)-benzamide;
1-(2,3-difluoro-phenyl)-3-[4-(2-trifluoromethyl-benzoimidazol-1-yl)-phenyl]-acrylonitrile;
1-(2,5-difluoro-phenyl)-3-[4-(2-trifluoromethyl-benzoimidazol-1-yl)-phenyl]-acrylonitrile;
2,3-Difluoro-N-[4-(2-isopropyl-benzoimidazol-1-yl)-phenyl]-benzamide;
N'-[4-(2-trifluoromethyl-benzoimidazol-1-yl)-phenyl]-N-(2,5-difluorophenyl)-urea;
1-Oxo-3-fluoro-N-[4-(2-trifluoromethyl-benzoimidazol-1-yl)-phenyl]-isonicotinamide;
2,3-Difluoro-N-[4-(trifluoromethyl-benzoimidazol-1-yl)-phenyl]-benzenesulfonamide;
2,3-Difluoro-N-[3-acetylamino-4-(trifluoromethyl-benzoimidazol-1-yl)-phenyl]-benzamide;
2,3-Difluoro-N-[4-(benzoimidazol-1-yl)-phenyl]-benzamide;
2,3-Difluoro-N-[2-methyl-4-(2-trifluoromethyl-benzoimidazol-1-yl)-phenyl]-benzamide;
2,5-Difluoro-N-[4-(2-trifluoromethyl-imidazo[4,5-b]pyrid-3-yl)-phenyl]-benzamide;
2,3-Difluoro-N-{4-[2-trifluoromethyl-5-(1,3-dioxo-isoindol-2-yl)-benzoimidazol-1-yl]-phenyl}-benzamide;
4-Methyl-[1,2,3]thiadiazole-5-carboxylic acid {N-[4-(2-trifluoromethyl-imidazo[4,5-b]pyrid-3-yl)-phenyl]}amide;
2,3-Difluoro-N-[4-(2-methyl-benzoimidazol-yl)-phenyl]-benzamide;
2,3-Difluoro-N-[4-(2-trifluoromethyl-5,6-dihydroxy-benzoimidazol-1-yl)-phenyl]-benzamide;
2,3-Difluoro-N-[4-(2-trifluoromethyl-imidazo[4,5-c]pyrid-1-yl)-phenyl]-benzamide;
4-Methyl-[1,2,3]thiadiazole-5-carboxylic acid {N-[2-(2-trifluoromethyl-benzoimidazol-1-yl)-pyrid-5-yl]}amide;
2,4,6-Trichloro-N-[4-(2-trifluoromethyl-5-methoxy-benzoimidazol-1-yl)-phenyl]-benzamide;
2,3-Difluoro-N-{4-[2,5-di-(trifluoromethyl)-benzoimidazol-1-yl]-phenyl}-benzamide;
2,3-Difluoro-N-[4-(2-trifluoromethyl-5-methanesulfonyl-benzoimidazol-1-yl)-phenyl]-benzamide;
4-Butyl-N-[4-(2-trifluoromethyl-5-methoxy-benzoimidazol-1-yl)-phenyl]-benzamide;
2,5-Difluoro-N-{4-[2-trifluoromethyl-5-(5-tert-butyl-oxazol-2-yl)-benzoimidazol-1-yl]-phenyl}-benzamide;
2,3-Difluoro-N-{4-[2-trifluoromethyl-5-(5-tert-butyl-oxazol-2-yl)-benzoimidazol-1-yl]-phenyl}-benzamide;
Furan-2-carboxylic acid (N-{4-[2-trifluoromethyl-5-(5-tert-butyl-oxazol-2-yl)-benzoimidazol-1-yl]-phenyl})amide;
2,3-Difluoro-N-[4-(2-trifluoromethyl-imidazo[1,2-a]pyrid-3-yl)-phenyl]-benzamide;
2,3,4,5-Tetrafluoro-N-[4-(2-trifluoromethyl-5-methoxy-benzoimidazol-1-yl)-phenyl]-benzamide;
4-Phenyl-N-[4-(2-trifluoromethyl-5-methoxy-benzoimidazol-1-0)-phenyl]-benzamide;
4-Iodo-N-[4-(2-trifluoromethyl-5-methoxy-benzoimidazol-1-yl)-phenyl]-benzamide;
Naphthalene-2-carboxylic acid {N-[4-(2-trifluoromethyl-5-methoxy-benzoimidazol-1-yl)-phenyl]}amide;
Benzo[1,3]dioxole-5-carboxylic acid {N-[4-(2-trifluoromethyl-5-methoxy-benzoimidazol-1-yl)-phenyl]}amide;
4-Methyl-N-[4-(2-trifluoromethyl-5-methoxy-benzoimidazol-1-yl)-phenyl]-benzamide;
4-Cyano-N-[4-(2-trifluoromethyl-5-methoxy-benzoimidazol-1-yl)-phenyl]-benzamide;
4-Nitro-N-[4-(2-trifluoromethyl-5-methoxy-benzoimidazol-1-yl)-phenyl]-benzamide;
4-Ethyl-N-[4-(2-trifluoromethyl-5-methoxy-benzoimidazol-1-yl)-phenyl]-benzamide;
4-Trifluoromethyl-N-[4-(2-trifluoromethyl-5-methoxy-benzoimidazol-1-yl)-phenyl]-benzamide;
3,5-Dinitro-N-[4-(2-trifluoromethyl-5-methoxy-benzoimidazol-1-yl)-phenyl]-benzamide;
N-[4-(2-trifluoromethyl-5-methoxy-benzoimidazol-1-yl)-phenyl]-butyramide;
Naphthalene-1-carboxylic acid {N-[4-(2-trifluoromethyl-5-methoxy-benzoimidazol-1-yl)-phenyl]}amide;
3-Methyl-N-[4-(2-trifluoromethyl-5-methoxy-benzoimidazol-1-yl)-phenyl]-but-2-enoic acid amide;

4-Propyl-N-[4-(2-trifluoromethyl-5-methoxy-benzoimidazol-1-yl)-phenyl]-benzamide;
Thiophene-2-carboxylic acid {N-[4-(2-trifluoromethyl-5-methoxy-benzoimidazol-1-yl)-phenyl]}amide;
2-Ethyl-N-[4-(2-trifluoromethyl-5-methoxy-benzoimidazol-1-yl)-phenyl]-hexanoic acid amide;
N-[4-(2-trifluoromethyl-5-methoxy-benzoimidazol-1-yl)-phenyl]-heptanoic acid amide;
3-Methoxy-N-[4-(2-trifluoromethyl-5-methoxy-benzoimidazol-1-yl)-phenyl]-benzamide;
2-Phenyl-N-[4-(2-trifluoromethyl-5-methoxy-benzoimidazol-1-yl)-phenyl]-cyclopropanecarboxylic acid amide;
3-Trifluoromethyl-N-[4-(2-trifluoromethyl-5-methoxy-benzoimidazol-1-yl)-phenyl]-benzamide;
2-(4-Methoxy-phenyl)-N-[4-(2-trifluoromethyl-5-methoxy-benzoimidazol-1-yl)-phenyl]-acetamide;
2,3-Difluoro-N-[4-(2-trifluoromethyl-6-acetylamino-benzoimidazol-1-yl)-phenyl]-benzamide;
2-(Thien-2-yl)-N-[4-(2-trifluoromethyl-5-methoxy-benzoimidazol-1-yl)-phenyl]-acetamide;
2-phenyl-N-[4-(2-trifluoromethyl-5-methoxy-benzoimidazol-1-yl)-phenyl]-acetamide;
2-Trifluoromethyl-1-[4-(2,3-difluoro-benzoylamino)-phenyl]-1H-benzoimidazole-5-carboxylic acid methyl ester,
2,3,4,5,6-Pentafluoro-N-[4-(2-trifluoromethyl-5-methoxy-benzoimidazol-1-yl)-phenyl]-benzamide;
2,4-Difluoro-N-[4-(2-trifluoromethyl-5-methoxy-benzoimidazol-1-yl)-phenyl]-benzamide;
2,3-Difluoro-N-[4-(2-trifluoromethyl-5-hydroxy-benzoimidazol-1-yl)-phenyl]-benzamide;
2,5-Difluoro-N-[4-(2-trifluoromethyl-5-methoxy-benzoimidazol-1-yl)-phenyl]-benzamide;
3-Cyano-N-[4-(2-trifluoromethyl-5-methoxy-benzoimidazol-1-yl)-phenyl]-benzamide;
2,6-Dichloro-N-[4-(2-trifluoromethyl-5-methoxy-benzoimidazol-1-yl)-phenyl]-benzamide;
3,5-Dichloro-N-[4-(2-trifluoromethyl-5-methoxy-benzoimidazol-1-yl)-phenyl]-benzamide;
2-Bromo-N-[4-(2-trifluoromethyl-5-methoxy-benzoimidazol-1-yl)-phenyl]-benzamide;
N-[4-(2-trifluoromethyl-5-methoxy-benzoimidazol-1-yl)-phenyl]-cyclopentanecarboxylic acid amide;
N-[4-(2-trifluoromethyl-5-methoxy-benzoimidazol-1-yl)-phenyl]-cyclohexanecarboxylic acid amide;
2-Nitro-N-[4-(2-trifluoromethyl-5-methoxy-benzoimidazol-1-yl)-phenyl]-benzamide;
4-Chloro-N-[4-(2-trifluoromethyl-5-methoxy-benzoimidazol-1-yl)-phenyl]-benzamide;
3-Chloro-N-[4-(2-trifluoromethyl-5-methoxy-benzoimidazol-1-yl)-phenyl]-benzamide;
3,4-Difluoro-N-[4-(2-trifluoromethyl-5-methoxy-benzoimidazol-1-yl)-phenyl]-benzamide;
N-[4-(2-trifluoromethyl-5-methoxy-benzoimidazol-1-yl)-phenyl]-benzamide;
2,3-Difluoro-N-[4-(2-trifluoromethyl-5-isopropoxy-benzoimidazol-1-yl)-phenyl]-benzamide;
2,3-Difluoro-N-[4-(2-trifluoromethyl-5-carbamoyl-benzoimidazol-1-yl)-phenyl]-benzamide;
N-[4-(2-trifluoromethyl-5-methoxy-benzoimidazol-1-yl)-phenyl]-isonicotinamide;
2-Iodo-N-[4-(2-trifluoromethyl-5-methoxy-benzoimidazol-1-yl)-phenyl]-benzamide;
3-Methyl-N-[4-(2-trifluoromethyl-5-methoxy-benzoimidazol-1-yl)-phenyl]-butyramide;
3,5-Dichloro-N-[4-(2-trifluoromethyl-5-methoxy-benzoimidazol-1-yl)-phenyl]-benzamide;
3-Bromo-N-[4-(2-trifluoromethyl-5-methoxy-benzoimidazol-1-yl)-phenyl]-benzamide;
4-Bromo-N-[4-(2-trifluoromethyl-5-methoxy-benzoimidazol-1-yl)-phenyl]-benzamide;
Furan-2-carboxylic acid {N-[4-(2-trifluoromethyl-5-methoxy-benzoimidazol-1-yl)-phenyl]}-amide;
1-(2,2,2-Trifluoroacetyl)-N-[4-(2-trifluoromethyl-5-methoxy-benzoimidazol-1-yl)-phenyl]-pyrrolidine-2-carboxylic acid amide;
N-[4-(2-trifluoromethyl-5-methoxy-benzoimidazol-1-yl)-phenyl]-acrylamide;
2-Benzyloxy-N-[4-(2-trifluoromethyl-5-methoxy-benzoimidazol-1-yl)-phenyl]-acetamide;
2-Phenylsulfanyl-N-[4-(2-trifluoromethyl-5-methoxy-benzoimidazol-1-yl)-phenyl]-acetamide;
N-[4-(2-trifluoromethyl-5-methoxy-benzoimidazol-1-yl)-phenyl]-succinamic acid ethyl ester;
2-Chloro-N-[4-(2-trifluoromethyl-5-methoxy-benzoimidazol-1-yl)-phenyl]-benzamide;
2,5-Di-(trifluoromethyl)-N-[4-(2-trifluoromethyl-5-methoxy-benzoimidazol-1-yl)-phenyl]-benzamide;
2-Methoxy-N-[4-(2-trifluoromethyl-5-methoxy-benzoimidazol-1-yl)-phenyl]-benzamide;
3,5-Di-(trifluoromethyl)-N-[4-(2-trifluoromethyl-5-methoxy-benzoimidazol-1-yl)-phenyl]-benzamide;
2,5-Dimethoxy-N-[4-(2-trifluoromethyl-5-methoxy-benzoimidazol-1-yl)-phenyl]-benzamide;
2-(3,4-dimethoxy-phenyl)-N-[4-(2-trifluoromethyl-5-methoxy-benzoimidazol-1-yl)-phenyl]-acetamide;
2,3-Difluoro-N-[4-(2-trifluoromethyl-5-acetoxy-benzoimidazol-1-yl)-phenyl]-benzamide;
2,3-Difluoro-N-[4-(2-trifluoromethyl-5-acetyl-benzoimidazol-1-yl)-phenyl]-benzamide;
2,6-Difluoro-N-[4-(2-trifluoromethyl-5-methoxy-benzoimidazol-1-yl)-phenyl]-benzylamine;
N-[4-(5-Chloro-2-trifluoromethyl-benzoimidazol-1-yl)-phenyl]-N-(2,3-difluoro-benzoyl)-2,3-difluoro-benzamide;
N-[4-(6-Chloro-2-trifluoromethyl-benzoimidazol-1-yl)-phenyl]-N-(2,3-difluoro-benzoyl)-2,3-difluoro-benzamide;
2-Methyl-N-[4-(7-methoxy-5,6,7,8-tetrahydroindolizin-3-yl)-phenyl]-benzamide;
3-Methyl-N-[4-(7-methoxy-5,6,7,8-tetrahydroindolizin-3-yl)-phenyl]-isonicotinamide;
2-Methyl-3-fluoro-N-[4-(7-methoxy-5,6,7,8-tetrahydroindolizin-3-yl)-phenyl]-benzamide;
3-Cyano-N-[4-(7-methoxy-5,6,7,8-tetrahydroindolizin-3-yl)-phenyl]-benzamide;
2-Nitro-N-[4-(7-methoxy-5,6,7,8-tetrahydroindolizin-3-yl)-phenyl]-benzamide;
2,6-Difluoro-3-iodo-N-[4-(7-methoxy-5,6,7,8-tetrahydroindolizin-3-yl)-phenyl]-benzamide;
2-Chloro-N-[4-(7-methoxy-5,6,7,8-tetrahydroindolizin-3-yl)-phenyl]-benzamide;
N-[4-(7-methoxy-5,6,7,8-tetrahydroindolizin-3-yl)-phenyl]-cyclohexanecarboxylic acid amide;
2-Methyl-N-[4-(7-methoxy-imidazo[1,2-a]pyrid-3-yl)-phenyl]-benzamide;
3-Fluoro-N-[4-(7-methoxy-imidazo[1,2-a]pyrid-3-yl)-phenyl]-isonicotinamide;
2-Methyl-3-fluoro-N-[4-(7-methoxy-imidazo[1,2-a]pyrid-3-yl)-phenyl]-benzamide;
3-Cyano-N-[4-(7-methoxy-imidazo[1,2-a]pyrid-3-yl)-phenyl]-benzamide;
3-Nitro-N-[4-(7-methoxy-imidazo[1,2-a]pyrid-3-yl)-phenyl]-benzamide;

2,6-Difluoro-3-iodo-N-[4-(7-methoxy-imidazo[1,2-a]pyrid-3-yl)-phenyl]-benzamide;
2-Chloro-N-[4-(7-methoxy-imidazo[1,2-a]pyrid-3-yl)-phenyl]-benzamide;
N-[4-(7-methoxy-imidazo[1,2-a]pyrid-3-yl)-phenyl]-cyclohexanecarboxylic acid amide;
2-Methyl-N-[4-(5-methoxy-benzoimidazol-1-yl)-phenyl]-benzamide;
2-Fluoro-N-[4-(5-methoxy-benzoimidazol-1-yl)-phenyl]-isonicotinamide;
2-Methyl-3-fluoro-N-[4-(5-methoxy-benzoimidazol-1-yl)-phenyl]-benzamide;
3-Cyano-N-[4-(5-methoxy-benzoimidazol-1-yl)-phenyl]-benzamide;
2-Nitro-N-[4-(5-methoxy-benzoimidazol-1-yl)-phenyl]-benzamide;
2,6-Difluoro-3-iodo-N-[4-(5-methoxy-benzoimidazol-1-yl)-phenyl]-benzamide;
2-Chloro-N-[4-(5-methoxy-benzoimidazol-1-yl)-phenyl]-benzamide;
N-[4-(5-methoxy-benzoimidazol-1-yl)-phenyl]-cyclohexanecarboxylic acid amide;
(2,6-Difluoro-benzyl)-[4-(5-methoxy-2-trifluoromethyl-benzoimidazol-1-yl)-phenyl]-amine; and
pharmaceutically acceptable salts, solvates, clathrates, or prodrugs thereof.

Particular compounds of any one of formulas (I) through (XVII) include those embodiments below.

In one embodiment, ring A is an optionally substituted phenyl.
In another embodiment, ring A is an optionally substituted pyridyl.
In another embodiment, ring A is an optionally substituted thienyl.
In another embodiment, ring A is an optionally substituted furanyl.
In another embodiment, ring A is an optionally substituted pyrrolyl.
In one embodiment, A is —CH=CH—, —CH=N—, or —N=CH—.
In another embodiment, A is —NH—, —O—, or —S(O)$_p$—.
In one embodiment, L is a linker selected from the group consisting of —C(O)—, —NR—C(O)—, —C(O)—NR—, C(S)—, —NR—C(S)—, —C(S)—NR— (e.g., —NH—C(O)— or —C(O)—NH—).
In another embodiment, L is —NHC(O)— or —NHCH$_2$—.
In another embodiment, L is —NHC(O)—, —NHC(S)NH—, —NHC(O)NH—, —CH=C(CN)—, or —NHS(O)$_2$—.
In one embodiment, Y is an optionally substituted 5 or 6 membered aryl, an optionally substituted 5 or 6 membered heteroaryl, or an optionally substituted 5 or 6 membered cycloalkyl.
In another embodiment, Y is selected from the group consisting of an alkyl, an optionally substituted alkenyl, an optionally substituted phenyl, an optionally substituted pyridyl, an optionally substituted furanyl, an optionally substituted thienyl, an optionally substituted cyclopentyl, an optionally substituted cyclohexyl, an optionally substituted naphthyl, an optionally substituted benzo[1,3]dioxolyl, and an optionally substituted [1,2,3]thiadiazolyl.
In another embodiment, Y is an optionally substituted phenyl or an optionally substituted [1,2,3]thiadiazolyl.

In another embodiment, Y is an optionally substituted phenyl, an optionally substituted pyridyl, an optionally substituted thiophenyl, [1,2,3]thiadiazolyl, an optionally substituted furanyl, an optionally substituted benzo[1,3]dioxolyl, an optionally substituted naphthyl, an optionally substituted cyclopentyl, an optionally substituted cyclohexyl, or isobutyl.
In another embodiment, Y is an optionally substituted phenyl, an optionally substituted pyridyl, an optionally substituted cyclopentyl, an optionally substituted cyclohexyl, or isobutyl.
In another embodiment, Y is cyclopentyl, cyclohexyl, isobutyl, propyl, t-butyl, or 2,2-dimethylpropyl.
In another embodiment, Y is an optionally substituted cycloalkyl.
In another embodiment, Y is optionally substituted aryl or optionally substituted heteroaryl (e.g., phenyl, pyridyl, thiophenyl, [1,2,3]thiadiazolyl, furanyl, benzo[1,3]dioxolyl, or naphthyl), any of which may be optionally substituted with 1-3 (e.g., 1-2) substituents independently selected from halo (e.g., F, Cl, Br, and I), lower alkyl (e.g., methyl and ethyl), lower haloalkyl (e.g., CF$_3$), nitro, lower haloalkoxy, amino, phenyl, cyano, or lower alkoxy.
In another embodiment, Y is a phenyl which is optionally substituted with 1 to 5 substituents which are independently selected from the group consisting of a halo, lower alkyl, a lower haloalkyl, a lower haloalkoxy, cyano, or nitro.
In another embodiment, Y is an optionally substituted aryl. For example Y is selected from the group consisting of:

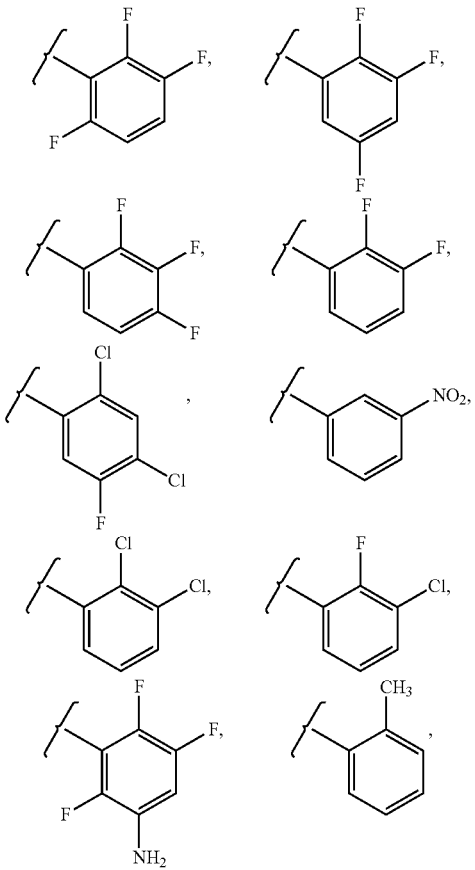

-continued
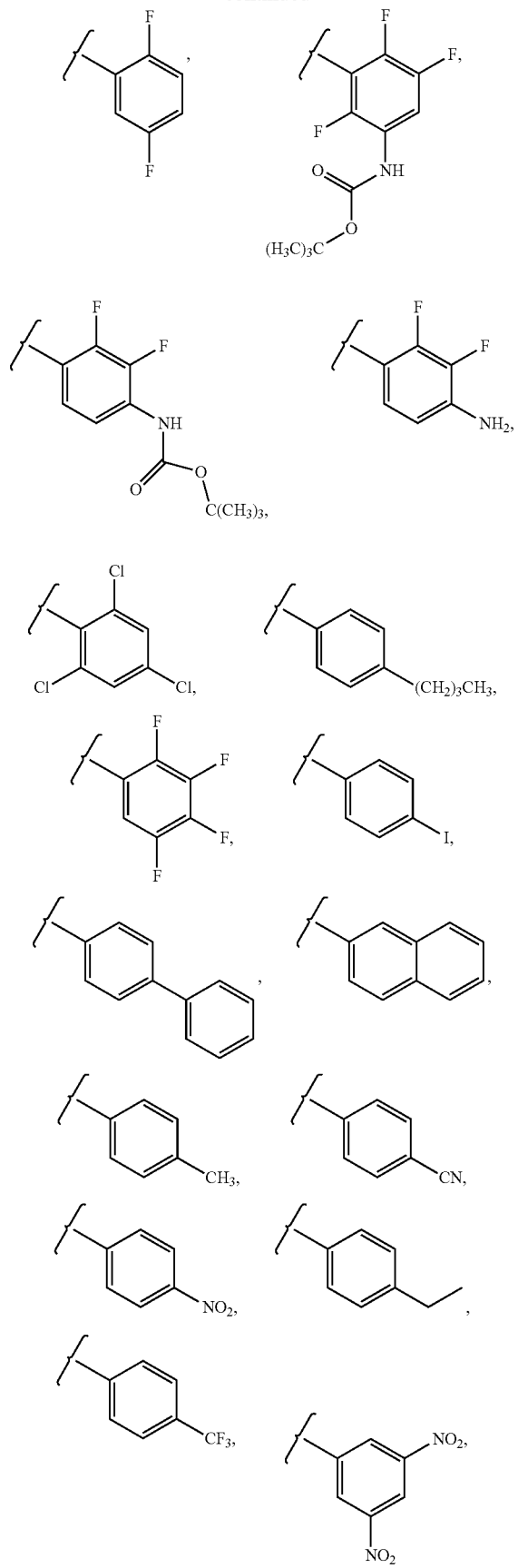
-continued
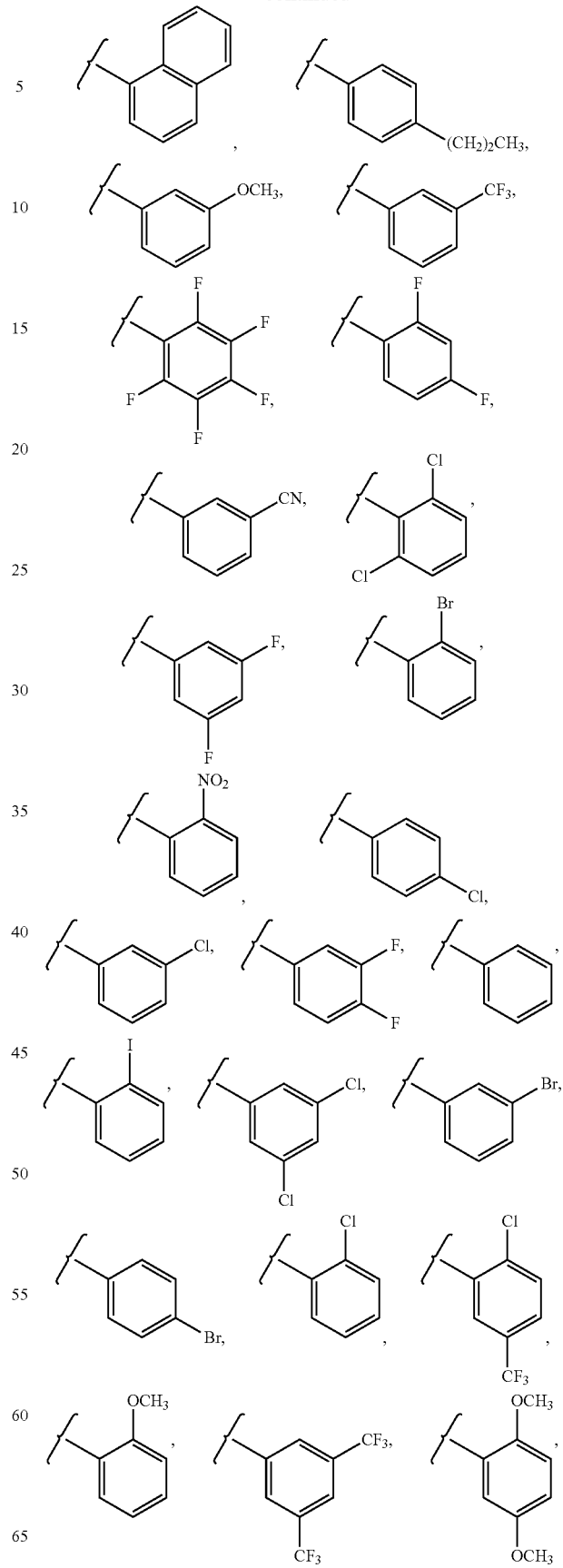

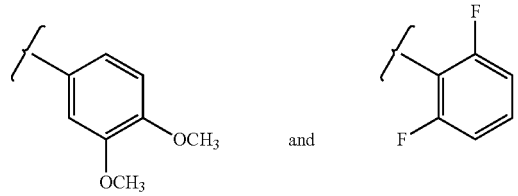

In another embodiment, Y is an optionally substituted pyridyl. For example Y is selected from the group consisting of:

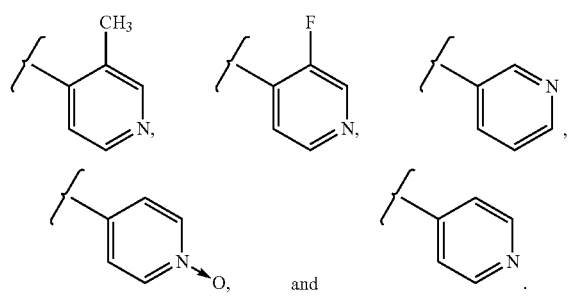

In another embodiment, Y is an optionally substituted 5-membered heteroaryl. For example Y is selected from the group consisting of:

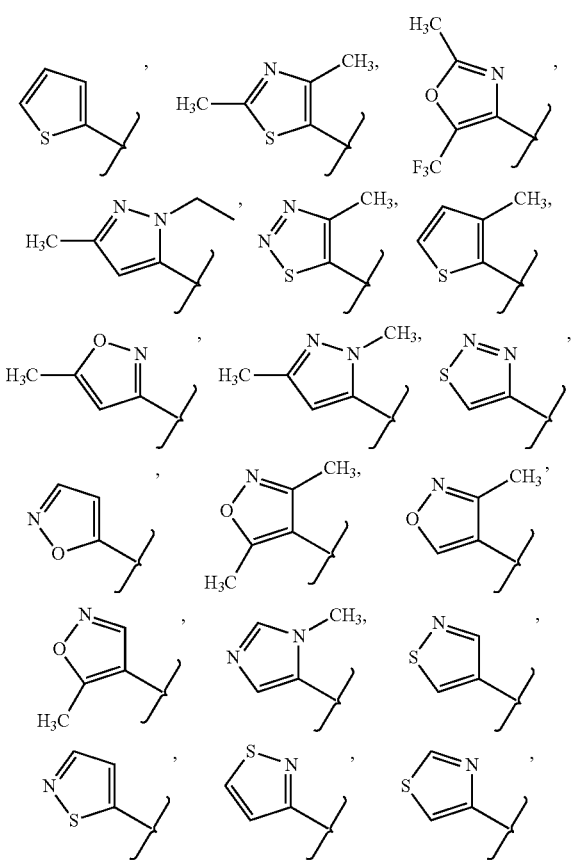

In a preferred embodiment, Y is selected from:

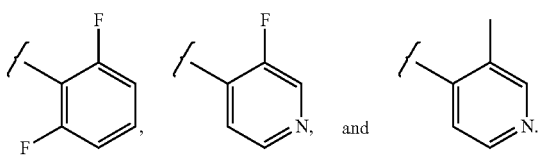

In one embodiment, $Y_1$ is an optionally substituted alkyl selected from the group consisting of propyl, 1-ethylpentyl, hexyl, isobutyl, phenylsulfanylmethyl, and O-ethyl-2-carboxyethyl, benzyloxymethyl.

In another embodiment, $Y_1$ is p-methoxybenzyl, benzyl, or m,p-dimethoxybenzyl.

In one embodiment, X is a benzoimidazolyl, a 5,6,7,8-tetrahydroindolizinyl, an imidazo[4,5-a]pyridyl, an imidazo[1,2-a]pyridyl, an imidazo[4,5-b]pyridyl, or an imidazo[4,5-c]pyridyl, each of which may be optionally substituted with one to four substituents selected from the group consisting of lower alkoxy, lower haloalkyl, lower haloalkoxy, cyano, halo, amino, hydroxyl, lower alkylsulfanyl, lower alkylsulfinyl, lower alkysulfonyl, 5-t-butyloxazolyl, —NHC(O)-(lower alkyl), —C(O)NH$_2$, —C(O)NH-(lower alkyl), —C(O)O-(lower alkyl), —C(O)OH, and —OC(O)-(lower alkyl).

In another embodiment, X is an optionally substituted benzoimidazolyl. For example, X is selected from the group consisting of

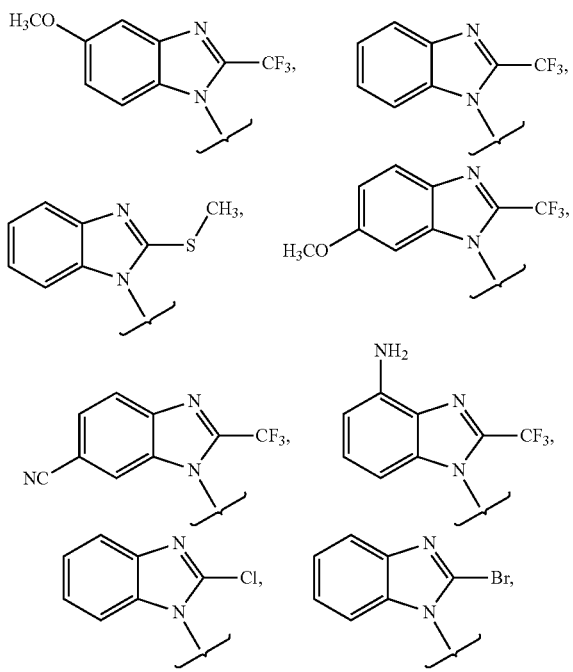

-continued

In another embodiment, X is an optionally substituted 5,6,7,8-tetrahydroindolizinyl. For example, X is selected from the group consisting of:

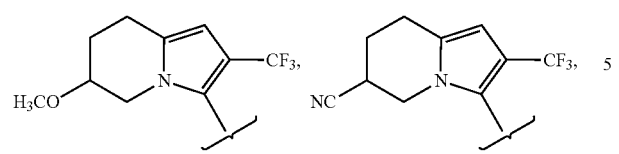
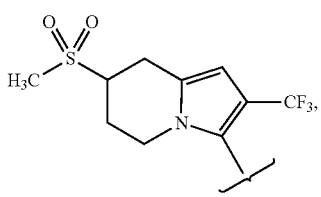
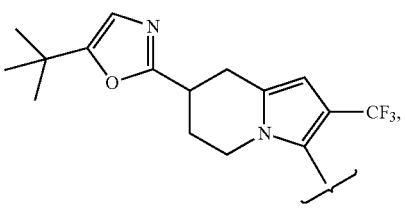
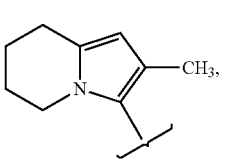
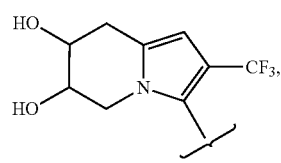
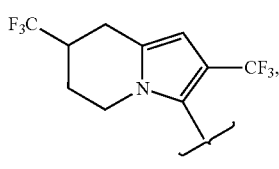
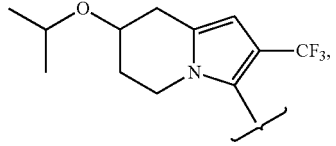
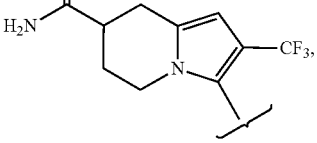
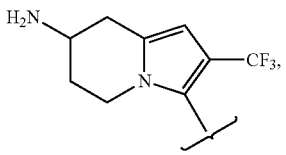
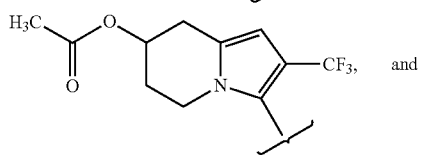
and
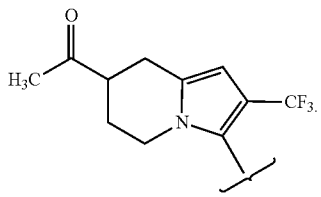

In another embodiment, X is an optionally substituted imidazopyridyl, such as an optionally substituted imidazo[1,2-a]pyridyl (e.g., 2-trifluoromethyl-imidazo[1,2-a]pyrid-3-yl), or an optionally substituted imidazo[4,5-b]pyridyl (e.g., 2-trifluoromethyl-imidazo[4,5-b]pyrid-3-yl), or an optionally substituted imidazo[4,5-c]pyridyl (e.g., 2-trifluoromethyl-imidazo[4,5-c]pyrid-1-yl).

In one embodiment, Z is independently selected from the group consisting of a lower alkyl (e.g., $CH_3$), a lower haloalkyl (e.g., $CF_3$), cyano, and halo (e.g., F and Cl).

In one embodiment, n is 0 and Z is absent.

In another embodiment, n is one.

In one embodiment, R, for each occurrence, is independently selected from —H, acetyl, tert-butoxycarbonyl, benzyloxycarbonyl (e.g., —H).

In one embodiment, $R_6$, for each occurrence, is, independently, selected from the group consisting of lower alkoxy, lower haloalkoxy, cyano, —$NH_2$, lower alkyl, —OH, lower haloalkyl, —S(O)$_2$-(lower alkyl), —NHC(O)-(lower alkyl), —C(O)O-(lower alkyl), —C(O)$NH_2$, and —C(O)-(lower alkyl).

In another embodiment, $R_6$ is —$OCH_3$, —$CF_3$, —C(O)$OCH_3$, —OH, —$OCH(CH_3)_2$, —C(O)$NH_2$, —OC(O)$CH_3$, —C(O)$CH_3$, or —$NH_2$.

In one embodiment, $R_7$ is selected from the group consisting of halo, lower haloalkyl, lower haloalkoxy, —S-(lower alkyl), and —S(O)-(lower alkyl).

In another embodiment, $R_7$ is —$CF_3$, —$OCHF_2$, —$SCH_3$, —Cl, or —Br.

In one embodiment, $R_8$, for each occurrence, is, independently, selected from the group consisting of halo, lower alkyl, nitro, —$NH_2$, —NHC(O)OC($CH_3)_3$, phenyl, cyano, lower haloalkyl, and —$OCH_3$.

In another embodiment, $R_8$, for each occurrence, is, independently, a halo, cyano or nitro.

Listed above are embodiments for substituents for the compounds represented by formulas (I) through (XVII). The substituents used for compounds of formulas (I) through (XVII) or any of the specific compound shown in Table 1 can be used in any combination that results in the formation of a stable compound. All such combinations are expressly encompassed in this invention.

In another embodiment, the invention relates to pharmaceutical compositions that comprise a compound of any one of formulas (I) through (XVII), or a compound shown in Table 1 or a pharmaceutically acceptable salt, solvate, clathrate, or prodrug thereof, as an active ingredient, and a pharmaceutically acceptable carrier or vehicle. The compositions are useful for immunosuppression or to treat or prevent inflammatory conditions, allergic disorders, and immune disorders.

In another embodiment, the invention relates to methods for immunosuppression or for treating or preventing inflammatory conditions, allergic disorders, or immune disorders in a patient in need thereof comprising administering an effective amount of a compound represented by any one of formulas (I) through (XVII), or a compound shown in Table 1 or a pharmaceutically acceptable salt, solvate, clathrate, or prodrug thereof.

In another embodiment, the invention relates to methods for immunosuppression or for treating or preventing inflammatory conditions, allergic disorders, or immune disorders in a patient in need thereof comprising administering an effective amount of a pharmaceutical composition that comprises a compound represented by any one of formulas (I) through (XVII), or a compound shown in Table 1, or a pharmaceutically acceptable salt, solvate, clathrate, or prodrug thereof.

In another embodiment, compounds of any one of formulas (I) through (XVII), or a compound shown in Table 1, or a pharmaceutically acceptable salt, solvate, clathrate, or prodrug thereof, are particularly useful inhibiting immune cell (e.g., T-cells, B-cells and/or mast cells) activation (e.g., activation in response to an antigen) and/or T cell, B cell and/or mast cell proliferation. Indicators of immune cell activation include secretion of IL-2 by T cells, proliferation of T cells, B cells, and/or mast cells and the like. In one embodiment, a compound of any one of formulas (I) through (XVII), or a compound shown in Table 1, inhibits immune cell activation and/or T cell, B cell and/or mast cell proliferation in a mammal (e.g., a human).

In another embodiment, compounds of any one of formula (I) through (XVII), or a compound shown in Table 1, or a pharmaceutically acceptable salt, solvate, clathrate, or prodrug thereof, can inhibit the production of certain cytokines that regulate immune cell activation. For example, compounds of any one of formulas (I) through (XVII), or a compound shown in Table 1, or a pharmaceutically acceptable salt, solvate, clathrate, or prodrug thereof, can inhibit the production of IL-2, IL-4, IL-5, IL-13, GM-CSF, IFN-γ, TNF-α and combinations thereof. In one embodiment, compounds of any one of formulas (I) through (XVII), or a compound shown in Table 1, or a pharmaceutically acceptable salt, solvate, clathrate, or prodrug thereof, inhibit the production of IL-2. In one embodiment, a compound of any one of formulas (I) through (XVII), or a compound shown in Table 1, inhibits cytokine production in a mammal (e.g., a human).

In another embodiment, compounds of any one of formulas (I) through (XVII), or a compound shown in Table 1, or a pharmaceutically acceptable salt, solvate, clathrate, or prodrug thereof, can modulate the activity of one or more ion channel involved in activation of immune cells, such as CRAC ion channel, TRPM4 and Kv1.3. In one embodiment, a compound of any one of formulas (I) through (XVII), or a compound shown in Table 1, or a pharmaceutically acceptable salt, solvate, clathrate, or prodrug thereof, can inhibit the influx of calcium ions into an immune cell (e.g., T cells, B cells, and/or mast cells) by inhibiting the action of CRAC ion channels. In general, a decrease in $I_{CRAC}$ current upon contacting a cell with a compound is one indicator that the compound inhibitions CRAC ion channels. $I_{CRAC}$ current can be measured, for example, using a patch clamp technique, which is described in more detail in the examples below. In another embodiment, a compound of any one of formulas (I) through (XVII), or a compound shown in Table 1, or a pharmaceutically acceptable salt, solvate, clathrate, or prodrug thereof, activates TRPM4 ion channels. In another embodiment, a compound of any one of formulas (I) through (XVII), or a compound shown in Table 1, or a pharmaceutically, acceptable salt, solvate, clathrate, or prodrug thereof, inhibits Kv1.3 ion channels. In one embodiment, a compound of any one of formulas (I) through (XVII), or a compound shown in Table 1, or a pharmaceutically acceptable salt, solvate, clathrate, or prodrug thereof, modulates an ion channel in a mammal (e.g., a human).

Exemplary Compounds of the Invention

Exemplary compounds of the invention are depicted in Table 1 below.

| Compound No. | Structure | Chemical Name |
|---|---|---|
| 1 | 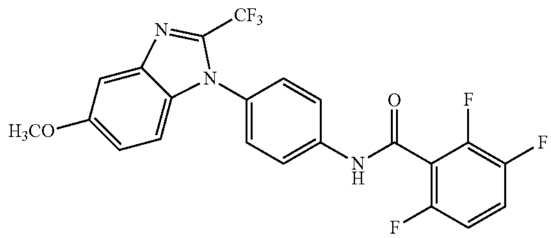 [SMILES: COc1ccc2c(c1)nc(C(F)(F)F)n2-c1ccc(NC(=O)c2c(F)ccc(F)c2F)cc1] | 2,3,6-Trifluoro-N-[4-(2-trifluoromethyl-5-methoxy-benzoimidazol-1-yl)-phenyl]-benzamide |
| 2 | 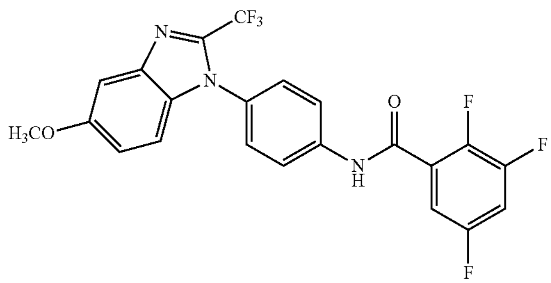 [SMILES: COc1ccc2c(c1)nc(C(F)(F)F)n2-c1ccc(NC(=O)c2cc(F)cc(F)c2F)cc1] | 2,3,5-Trifluoro-N-[4-(2-trifluoromethyl-5-methoxy-benzoimidazol-1-yl)-phenyl]-benzamide |
| 3 | 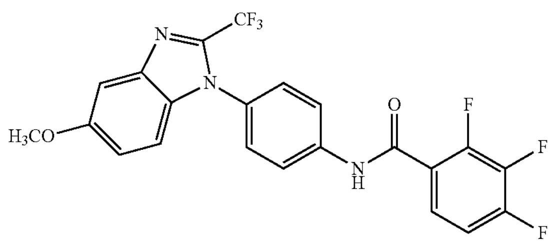 [SMILES: COc1ccc2c(c1)nc(C(F)(F)F)n2-c1ccc(NC(=O)c2ccc(F)c(F)c2F)cc1] | 2,3,4-Trifluoro-N-[4-(2-trifluoromethyl-5-methoxy-benzoimidazol-1-yl)-phenyl]-benzamide |
| 4 | 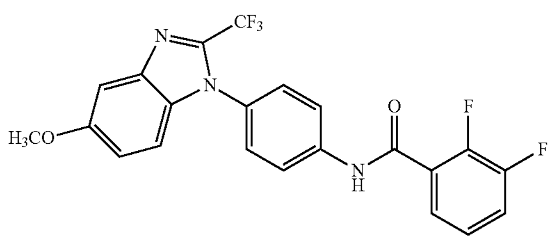 [SMILES: COc1ccc2c(c1)nc(C(F)(F)F)n2-c1ccc(NC(=O)c2cccc(F)c2F)cc1] | 2,3-Difluoro-N-[4-(2-trifluoromethyl-5-methoxy-benzoimidazol-1-yl)-phenyl]-benzamide |
| 5 | 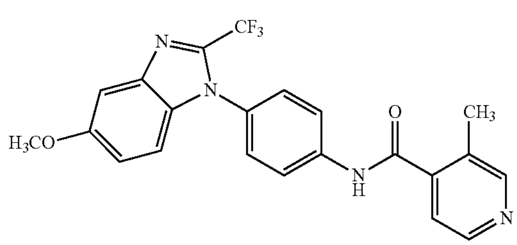 [SMILES: COc1ccc2c(c1)nc(C(F)(F)F)n2-c1ccc(NC(=O)c2ccncc2C)cc1] | 3-Methyl-N-[4-(2-trifluoromethyl-5-methoxy-benzoimidazol-1-yl)-phenyl]-isonicotinamide |
| 6 | 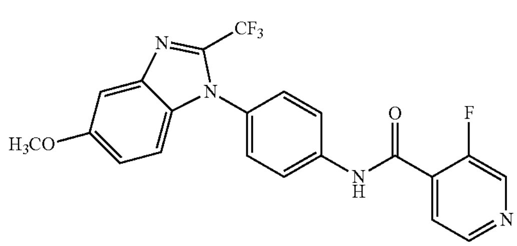 [SMILES: COc1ccc2c(c1)nc(C(F)(F)F)n2-c1ccc(NC(=O)c2ccncc2F)cc1] | 3-Fluoro-N-[4-(2-trifluoromethyl-5-methoxy-benzoimidazol-1-yl)-phenyl]-isonicotinamide |

-continued

| Compound No. | Structure | Chemical Name |
|---|---|---|
| 7 | 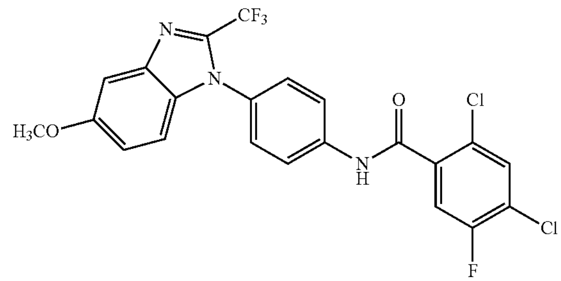 [SMILES: COc1ccc2c(c1)nc(C(F)(F)F)n2-c1ccc(NC(=O)c2cc(F)c(Cl)cc2Cl)cc1] | 2,4-Dichloro-5-fluoro-N-[4-(2-trifluoromethyl-5-methoxy-benzoimidazol-1-yl)-phenyl]-benzamide |
| 8 | 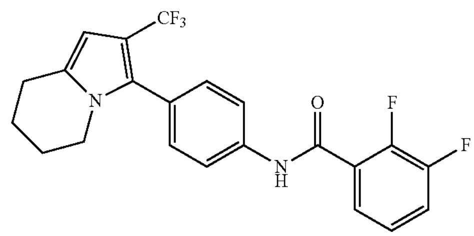 [SMILES: O=C(Nc1ccc(-c2c(C(F)(F)F)cc3n2CCCC3)cc1)c1cccc(F)c1F] | 2,3-Difluoro-N-[4-(2-trifluoromethyl-5,6,7,8-tetrahydroindolizin-3-yl)-phenyl]-benzamide |
| 9 | 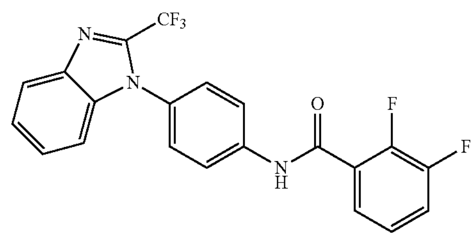 | 2,4-Difluoro-N-[4-(2-trifluoromethyl-benzoimidazol-1-yl)-phenyl]-benzamide |
| 10 | 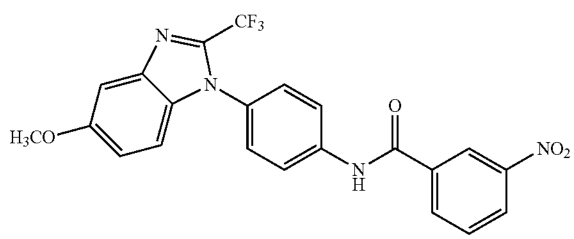 [SMILES: COc1ccc2c(c1)nc(C(F)(F)F)n2-c1ccc(NC(=O)c2cccc([N+](=O)[O-])c2)cc1] | 3-Nitro-N-[4-(2-trifluoromethyl-5-methoxy-benzoimidazol-1-yl)-phenyl]-benzamide |
| 11 | 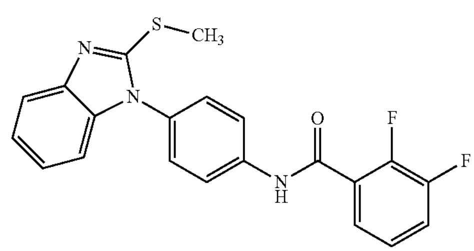 [SMILES: CSc1nc2ccccc2n1-c1ccc(NC(=O)c2cccc(F)c2F)cc1] | 2,3-Difluoro-N-[4-(2-methylsulfanyl-benzoimidazol-1-yl)-phenyl]-benzamide |
| 12 | 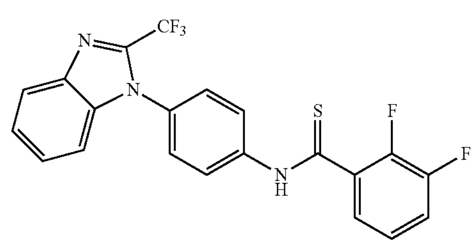 | 2,3-Difluoro-N-[4-(2-trifluoromethyl-benzoimidazol-1-yl)-phenyl]-thiobenzamide |

-continued

| Compound No. | Structure | Chemical Name |
|---|---|---|
| 13 | 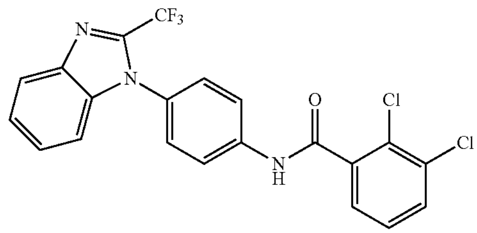 | 2,3-Dichloro-N-[4-(2-trifluoromethyl-benzoimidazol-1-yl)-phenyl]-benzamide |
| 14 | 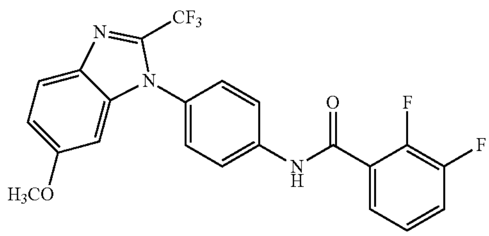 [SMILES: COc1ccc2nc(C(F)(F)F)n(-c3ccc(NC(=O)c4cccc(F)c4F)cc3)c2c1] | 2,3-Difluoro-N-[4-(2-trifluoromethyl-6-methoxy-benzoimidazol-1-yl)-phenyl]-benzamide |
| 15 | 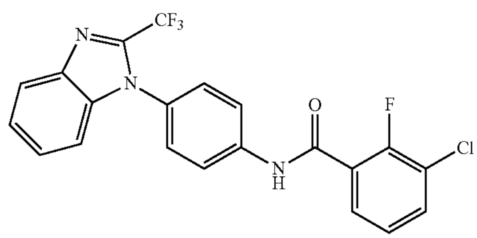 [SMILES: O=C(Nc1ccc(-n2c(C(F)(F)F)nc3ccccc32)cc1)c1cccc(Cl)c1F] | 2-Fluoro-2-chloro-N-[4-(2-trifluoromethyl-benzoimidazol-1-yl)-phenyl]-benzamide |
| 16 | 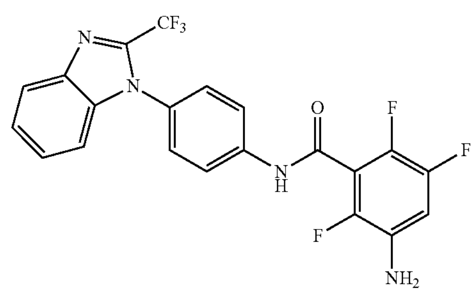 [SMILES: Nc1cc(F)c(F)c(C(=O)Nc2ccc(-n3c(C(F)(F)F)nc4ccccc43)cc2)c1F] | 2,3,6-Trifluoro-5-amino-N-[4-(2-trifluoromethyl-benzoimidazol-1-yl)-phenyl]-benzamide |
| 17 | 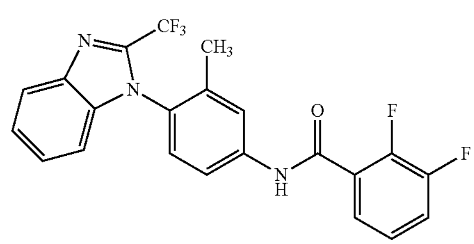 | 2,3-Difluoro-N-[3-methyl-4-(2-trifluoromethyl-benzoimidazol-1-yl)-phenyl]-benzamide |
| 18 | 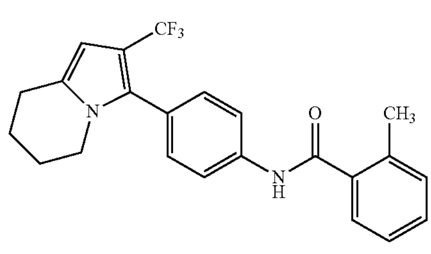 [SMILES: Cc1ccccc1C(=O)Nc1ccc(-c2c(C(F)(F)F)cc3n2CCCC3)cc1] | 2-Methyl-N-[4-(2-trifluoromethyl-5,6,7,8-tetrahydroindolizin-3-yl)-phenyl]-benzamide |

-continued

| Compound No. | Structure | Chemical Name |
|---|---|---|
| 19 | 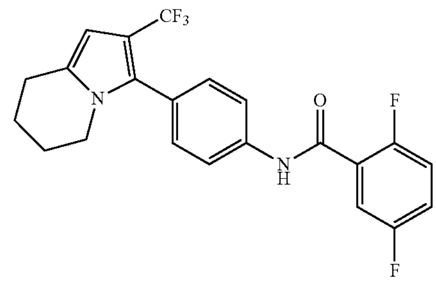 [SMILES: O=C(Nc1ccc(-c2c(C(F)(F)F)cc3n2CCCC3)cc1)c1cc(F)ccc1F] | 2,3-Difluoro-N-[4-(2-trifluoromethyl-5,6,7,8-tetrahydroindolizin-3-yl)-phenyl]-benzamide |
| 20 | 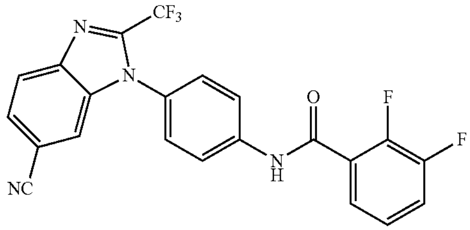 [SMILES: N#Cc1ccc2nc(C(F)(F)F)n(-c3ccc(NC(=O)c4cccc(F)c4F)cc3)c2c1] | 2,3-Difluoro-N-[4-(2-trifluoromethyl-6-cyano-benzoimidazol-1-yl)-phenyl]-benzamide |
| 21 | 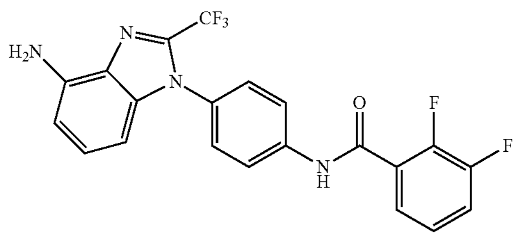 [SMILES: Nc1cccc2c1nc(C(F)(F)F)n2-c1ccc(NC(=O)c2cccc(F)c2F)cc1] | 2,3-Difluoro-N-[4-(2-trifluoromethyl-4-amino-benzoimidazol-1-yl)-phenyl]-benzamide |
| 22 | 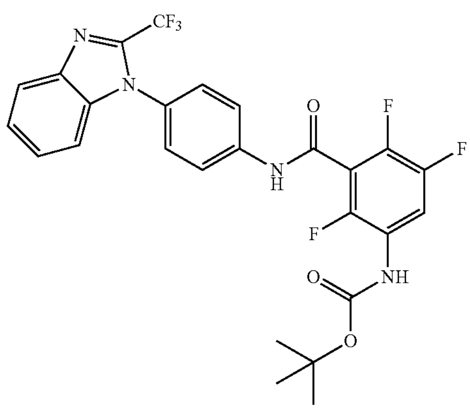 [SMILES: CC(C)(C)OC(=O)Nc1cc(F)c(F)c(C(=O)Nc2ccc(-n3c(C(F)(F)F)nc4ccccc43)cc2)c1F] | N-(3-{N-[4-(2-trifluoromethyl-benzoimidazol-1-yl)-phenyl]-carbamoyl}-2,4,5-trifluoro-phenyl)-carbamic acid t-butyl ester |
| 23 | 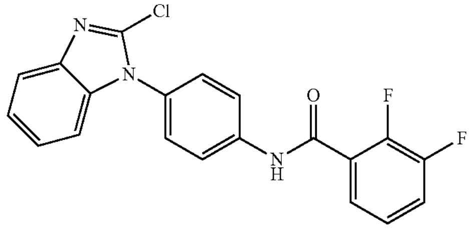 [SMILES: O=C(Nc1ccc(-n2c(Cl)nc3ccccc32)cc1)c1cccc(F)c1F] | 2,3-Difluoro-N-[4-(2-chloro-benzoimidazol-1-yl)-phenyl]-benzamide |

| Compound No. | Structure | Chemical Name |
|---|---|---|
| 24 | 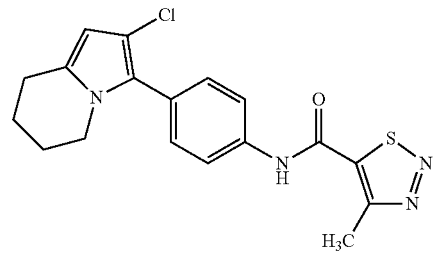 [SMILES: Cc1nnsc1C(=O)Nc1ccc(-c2c(Cl)cc3n2CCCC3)cc1] | 4-Methyl-[1,2,3]thiadiazole-5-carboxylic acid {N-[4-(2-chloro-5,6,7,8-tetrahydroindolizin-3-yl)-phenyl]} amide |
| 25 | 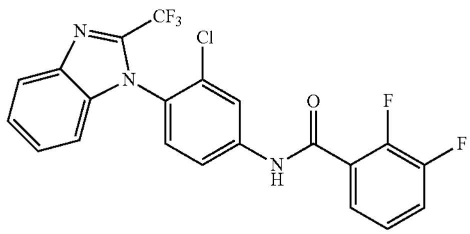 | 2,3-Difluoro-N-[2-chloro-4-(2-trifluoromethyl-benzoimidazol-1-yl)-phenyl]-benzamide |
| 26 | 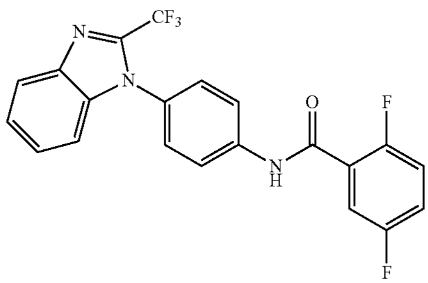 [SMILES: O=C(Nc1ccc(-n2c(C(F)(F)F)nc3ccccc32)cc1)c1cc(F)ccc1F] | 2,5-Difluoro-N-[4-(2-trifluoromethyl-benzoimidazol-1-yl)-phenyl]-benzamide |
| 27 | 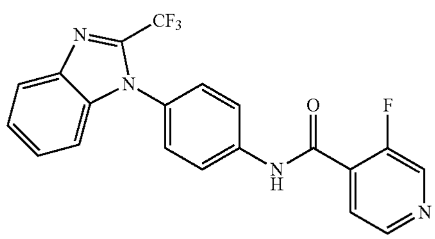 [SMILES: O=C(Nc1ccc(-n2c(C(F)(F)F)nc3ccccc32)cc1)c1ccncc1F] | 3-Fluoro-N-[4-(2-trifluoromethyl-benzoimidazol-1-yl)-phenyl]-isonicotinamide |
| 28 | 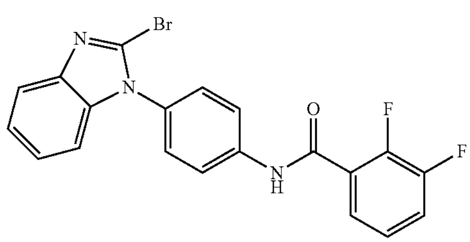 [SMILES: O=C(Nc1ccc(-n2c(Br)nc3ccccc32)cc1)c1cccc(F)c1F] | 2,3-Difluoro-N-[4-(2-bromo-benzoimidazol-1-yl)-phenyl]-benzamide |
| 29 | 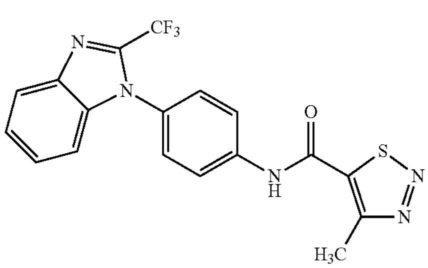 [SMILES: Cc1nnsc1C(=O)Nc1ccc(-n2c(C(F)(F)F)nc3ccccc32)cc1] | 4-Methyl-[1,2,3]thiadiazole-5-carboxylic acid {N-[4-(2-trifluoromethyl-benzoimidazol-1-yl)-phenyl]} amide |

-continued

| Compound No. | Structure | Chemical Name |
|---|---|---|
| 30 | 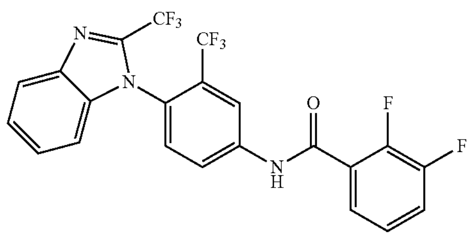 [SMILES: O=C(Nc1ccc(-n2c(C(F)(F)F)nc3ccccc32)c(C(F)(F)F)c1)c1cccc(F)c1F] | 2,3-Difluoro-N-[3-trifluoromethyl-4-(2-trifluoromethyl-benzoimidazol-1-yl)-phenyl]-benzamide |
| 31 | 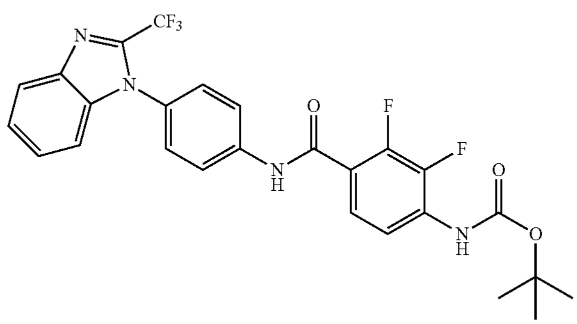 [SMILES: CC(C)(C)OC(=O)Nc1ccc(C(=O)Nc2ccc(-n3c(C(F)(F)F)nc4ccccc43)cc2)c(F)c1F] | N-(4-{N-[4-(2-trifluoromethyl-benzoimidazol-1-yl)-phenyl]-carbamoyl}-2,3-difluoro-phenyl)-carbamic acid t-butyl ester |
| 32 | 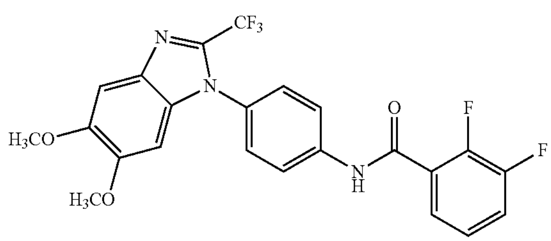 [SMILES: COc1cc2nc(C(F)(F)F)n(-c3ccc(NC(=O)c4cccc(F)c4F)cc3)c2cc1OC] | 2,3-Difluoro-N-[4-(2-trifluoromethyl-5,6-dimethoxy-benzoimidazol-1-yl)-phenyl]-benzamide |
| 33 | 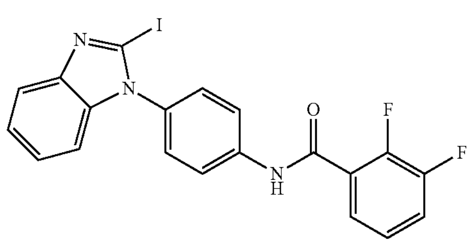 [SMILES: O=C(Nc1ccc(-n2c(I)nc3ccccc32)cc1)c1cccc(F)c1F] | 2,3-Difluoro-N-[4-(2-iodo-benzoimidazol-1-yl)-phenyl]-benzamide |
| 34 | 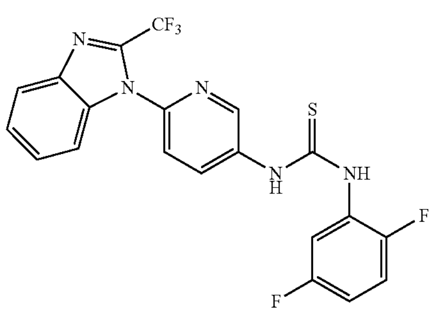 [SMILES: Fc1ccc(F)c(NC(=S)Nc2ccc(-n3c(C(F)(F)F)nc4ccccc43)nc2)c1] | N'-[2-(2-trifluoromethyl-benzoimidazol-1-yl)-pyrid-5-yl]-N-(2,5-difluoro-phenyl)-thiourea |
| 35 | 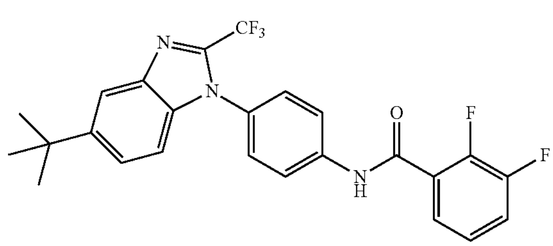 [SMILES: CC(C)(C)c1ccc2c(c1)nc(C(F)(F)F)n2-c1ccc(NC(=O)c2cccc(F)c2F)cc1] | 2,3-Difluoro-N-[4-(2-trifluoromethyl-5-tert-butyl-benzoimidazol-1-yl)-phenyl]-benzamide |

-continued

| Compound No. | Structure | Chemical Name |
|---|---|---|
| 36 | 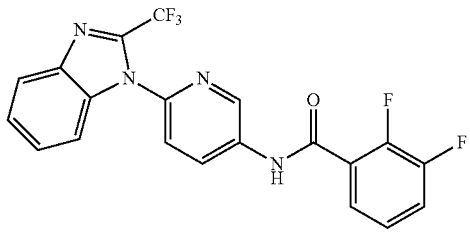 | 2,3-Difluoro-N-[2-(2-trifluoromethyl-benzoimidazol-1-yl)-pyrid-3-yl]-benzamide |
| 37 | 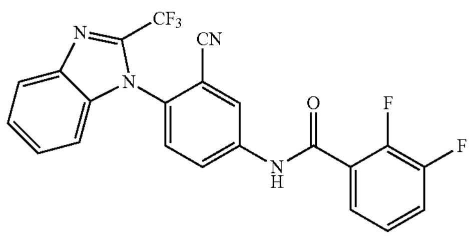 [SMILES: N#Cc1cc(NC(=O)c2cccc(F)c2F)ccc1-n1c(C(F)(F)F)nc2ccccc21] | 2,3-Difluoro-N-[3-cyano-4-(2-trifluoromethyl-benzoimidazol-1-yl)-phenyl]-benzamide |
| 38 | 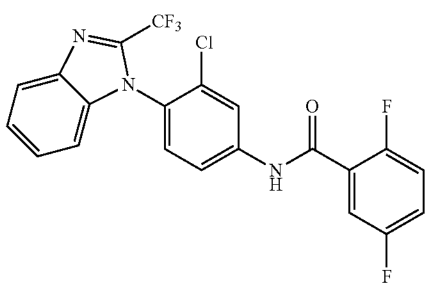 [SMILES: O=C(Nc1ccc(-n2c(C(F)(F)F)nc3ccccc32)c(Cl)c1)c1cc(F)ccc1F] | 2,5-Difluoro-N-[3-chloro-4-(2-trifluoromethyl-benzoimidazol-1-yl)-phenyl]-benzamide |
| 39 | 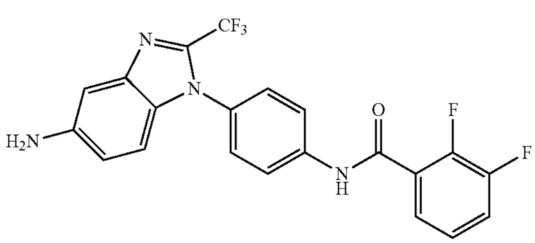 [SMILES: Nc1ccc2c(c1)nc(C(F)(F)F)n2-c1ccc(NC(=O)c2cccc(F)c2F)cc1] | 2,3-Difluoro-N-[4-(2-trifluoromethyl-5-amino-benzoimidazol-1-yl)-phenyl]-benzamide |
| 40 | 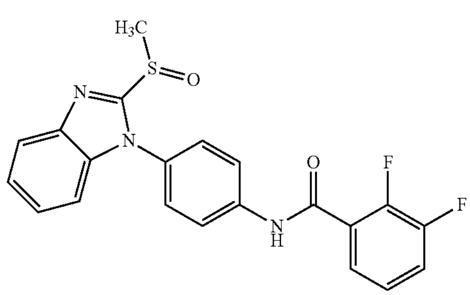 [SMILES: CS(=O)c1nc2ccccc2n1-c1ccc(NC(=O)c2cccc(F)c2F)cc1] | 2,3-Difluoro-N-[4-(2-methanesulfinyl-benzoimidazol-1-yl)-phenyl]-benzamide |

| Compound No. | Structure | Chemical Name |
|---|---|---|
| 41 | 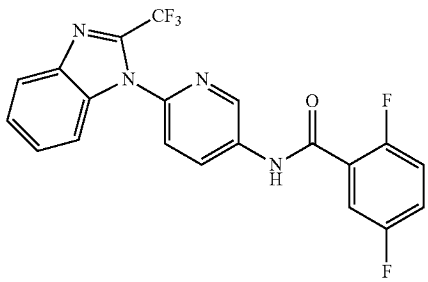 [SMILES: O=C(Nc1ccc(-n2c(C(F)(F)F)nc3ccccc32)nc1)c1cc(F)ccc1F] | 2,5-Difluoro-N-[2-(2-trifluoromethyl-benzoimidazol-1-yl)-pyrid-5-yl]-benzamide |
| 42 | 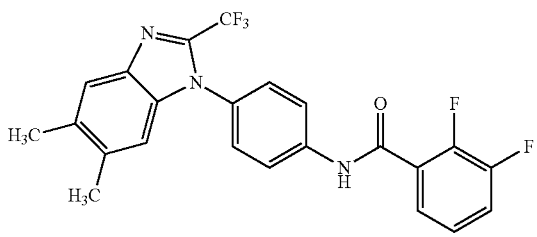 [SMILES: Cc1cc2nc(C(F)(F)F)n(-c3ccc(NC(=O)c4cccc(F)c4F)cc3)c2cc1C] | 2,3-Difluoro-N-[4-(2-trifluoromethyl-5,6-dimethyl-benzoimidazol-1-yl)-phenyl]-benzamide |
| 43 | 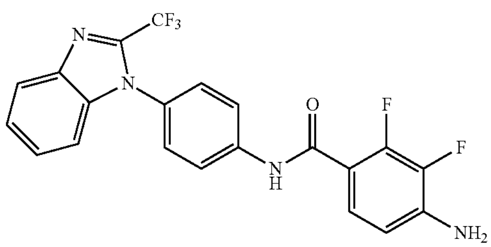 [SMILES: Nc1ccc(C(=O)Nc2ccc(-n3c(C(F)(F)F)nc4ccccc43)cc2)c(F)c1F] | 2,3-Difluoro-4-amino-N-[4-(2-trifluoromethyl-benzoimidazol-1-yl)-phenyl]-benzamide |
| 44 | 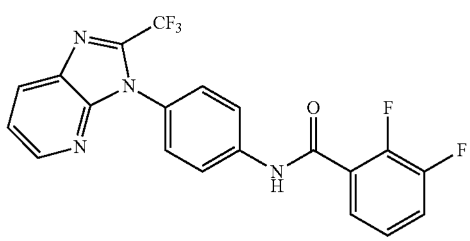 | 2,3-Difluoro-N-[4-(2-trifluoromethyl-imidazo[4,5-b]pyrid-3-yl)-phenyl]-benzamide |
| 45 | 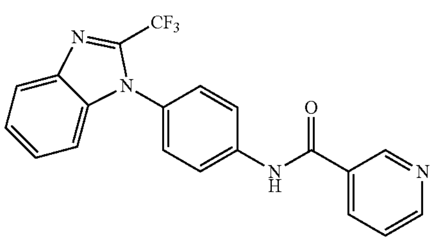 [SMILES: O=C(Nc1ccc(-n2c(C(F)(F)F)nc3ccccc32)cc1)c1cccnc1] | N-[4-(2-trifluoromethyl-benzoimidazol-1-yl)-phenyl]-nicotinamide |
| 46 | 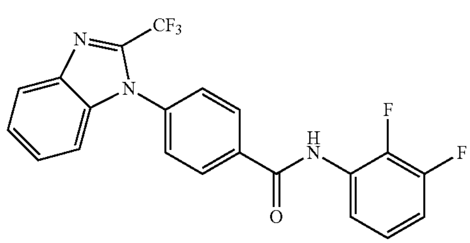 [SMILES: O=C(Nc1cccc(F)c1F)c1ccc(-n2c(C(F)(F)F)nc3ccccc32)cc1] | N-(2,3-difluorophenyl)-4-(2-trifluoromethyl-benzoimidazol-1-yl)-benzamide |

-continued

| Compound No. | Structure | Chemical Name |
|---|---|---|
| 47 | 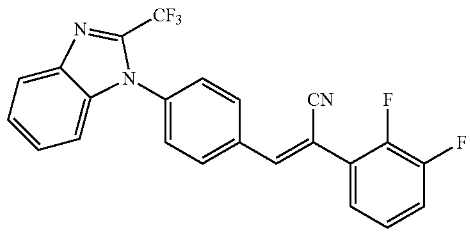 [SMILES: N#C/C(=C\c1ccc(-n2c(C(F)(F)F)nc3ccccc32)cc1)c1cccc(F)c1F] | 1-(2,3-difluoro-phenyl)-3-[4-(2-trifluoromethyl-benzoimidazol-1-yl)-phenyl]-acrylonitrile |
| 48 | 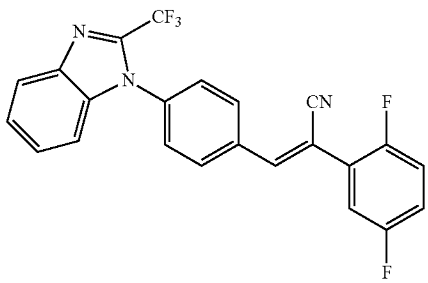 [SMILES: N#C/C(=C\c1ccc(-n2c(C(F)(F)F)nc3ccccc32)cc1)c1cc(F)ccc1F] | 1-(2,5-difluoro-phenyl)-3-[4-(2-trifluoromethyl-benzoimidazol-1-yl)-phenyl]-acrylonitrile |
| 49 | 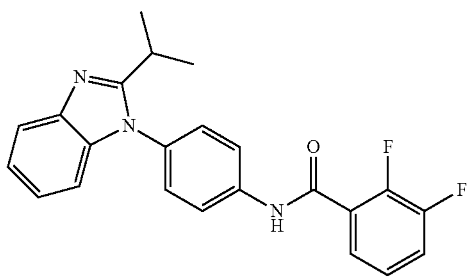 [SMILES: CC(C)c1nc2ccccc2n1-c1ccc(NC(=O)c2cccc(F)c2F)cc1] | 2,3-Difluoro-N-[4-(2-isopropyl-benzoimidazol-1-yl)-phenyl]-benzamide |
| 50 | 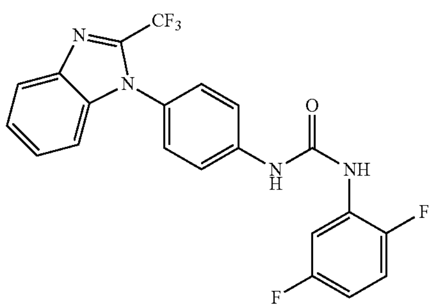 [SMILES: O=C(Nc1ccc(-n2c(C(F)(F)F)nc3ccccc32)cc1)Nc1cc(F)ccc1F] | N'-[4-(2-trifluoromethy-benzoimidazol-1-yl)-phenyl]-N-(2,5-difluoropheyl)-urea |
| 51 | 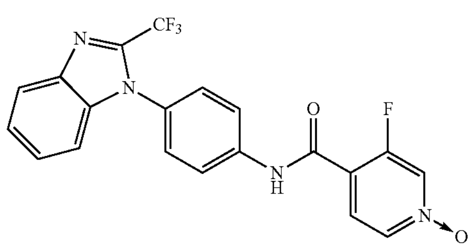 [SMILES: O=C(Nc1ccc(-n2c(C(F)(F)F)nc3ccccc32)cc1)c1cc[n+]([O-])cc1F] | 1-Oxo-3-fluoro-N-[4-(2-trifluoromethyl-benzoimidazol-1-yl)-phenyl]-isonicotinamide |
| 52 | 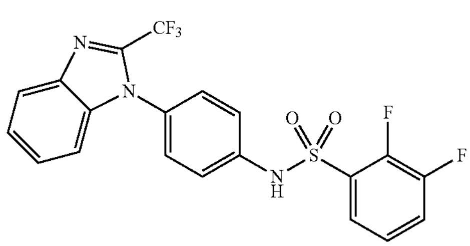 [SMILES: O=S(=O)(Nc1ccc(-n2c(C(F)(F)F)nc3ccccc32)cc1)c1cccc(F)c1F] | 2,3-Difluoro-N-[4-(trifluoromethyl-benzoimidazol-1-yl)-phenyl]-benzenesulfonamide |

-continued

| Compound No. | Structure | Chemical Name |
|---|---|---|
| 53 | 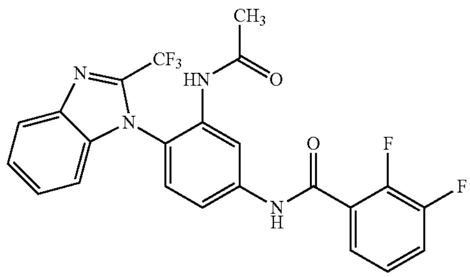 [SMILES: CC(=O)Nc1cc(NC(=O)c2cccc(F)c2F)ccc1-n1c(C(F)(F)F)nc2ccccc21] | 2,3-Difluoro-N-[3-acetylamino-4-(2-trifluoromethyl-benzoimidazol-1-yl)-phenyl]-benzamide |
| 54 | 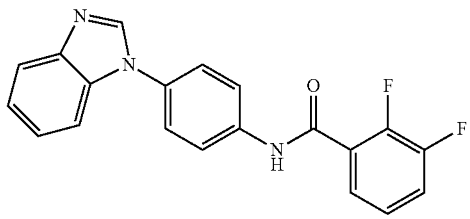 [SMILES: O=C(Nc1ccc(-n2cnc3ccccc32)cc1)c1cccc(F)c1F] | 2,3-Difluoro-N-[4-(benzoimidazol-1-yl)-phenyl]-benzamide |
| 55 | 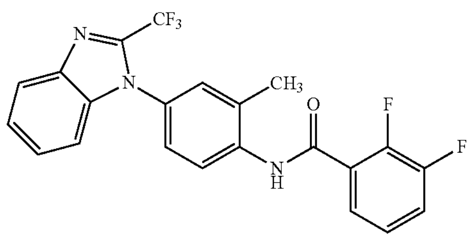 [SMILES: Cc1cc(-n2c(C(F)(F)F)nc3ccccc32)ccc1NC(=O)c1cccc(F)c1F] | 2,3-Difluoro-N-[2-methyl-4-(2-trifluoromethyl-benzoimidazol-1-yl)-phenyl]-benzamide |
| 56 | 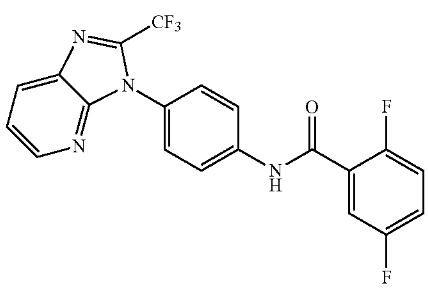 | 2,5-Difluoro-N-[4-(2-trifluoromethyl-imidazo[4,5-b]pyrid-3-yl)-phenyl]-benzamide |
| 57 | 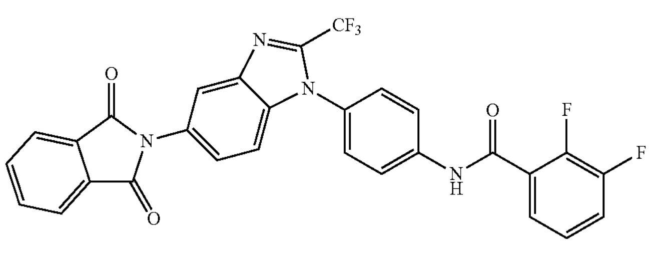 [SMILES: O=C(Nc1ccc(-n2c(C(F)(F)F)nc3cc(N4C(=O)c5ccccc5C4=O)ccc32)cc1)c1cccc(F)c1F] | 2,3-Difluoro-N-{4-[2-trifluoromethyl-5-(1,3-dioxo-isoindol-2-yl)-benzoimidazol-1-yl]-phenyl}-benzamide |
| 58 | 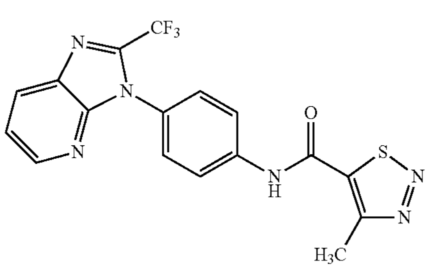 [SMILES: Cc1nnsc1C(=O)Nc1ccc(-n2c(C(F)(F)F)nc3cccnc32)cc1] | 4-Methyl-[1,2,3]thiadiazole-5-carboxylic acid {N-[4-(2-trifluoromethyl-imidazo[4,5-b]pyrid-3-yl)-phenyl]} amide |

| Compound No. | Structure | Chemical Name |
|---|---|---|
| 59 | 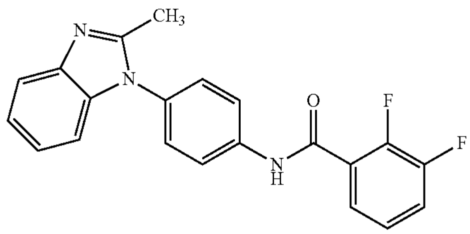 [SMILES: Cc1nc2ccccc2n1-c1ccc(NC(=O)c2cccc(F)c2F)cc1] | 2,3-Difluoro-N-[4-(2-methyl-benzoimidazol-1-yl)-phenyl]-benzamide |
| 60 | 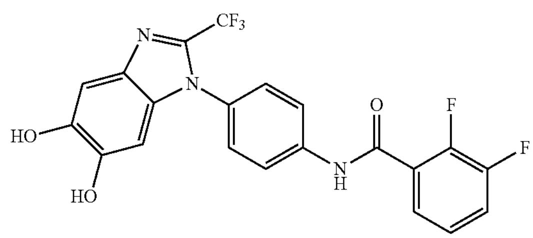 [SMILES: O=C(Nc1ccc(-n2c(C(F)(F)F)nc3cc(O)c(O)cc32)cc1)c1cccc(F)c1F] | 2,3-Difluoro-N-[4-(2-trifluoromethyl-5,6-dihydroxy-benzoimidazol-1-yl)-phenyl]-benzamide |
| 61 | 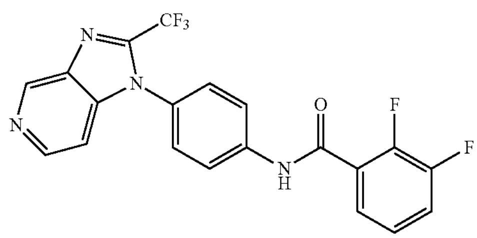 [SMILES: O=C(Nc1ccc(-n2c(C(F)(F)F)nc3cnccc32)cc1)c1cccc(F)c1F] | 2,3-Difluoro-N-[4-(2-trifluoromethyl-imidazo[4,5-c]pyrid-1-yl)-phenyl]-benzamide |
| 62 | 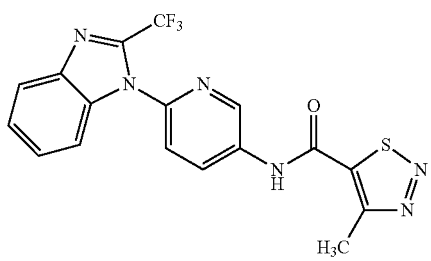 | 4-Methyl-[1,2,3]thiadiazole-5-carboxylic acid {N-[2-(2-trifluoromethyl-benzoimidazol-1-yl)-pyrid-5-yl]} amide |
| 63 | 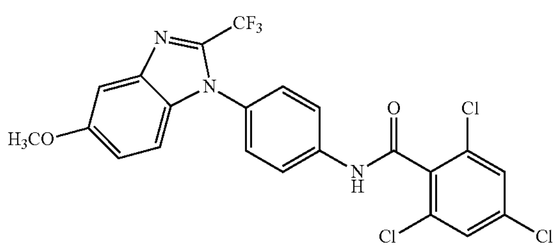 [SMILES: COc1ccc2c(c1)nc(C(F)(F)F)n2-c1ccc(NC(=O)c2c(Cl)cc(Cl)cc2Cl)cc1] | 2,4,6-Trichloro-N-[4-(2-trifluoromethyl-5-methoxy-benzoimidazol-1-yl)-phenyl]-benzamide |
| 64 | 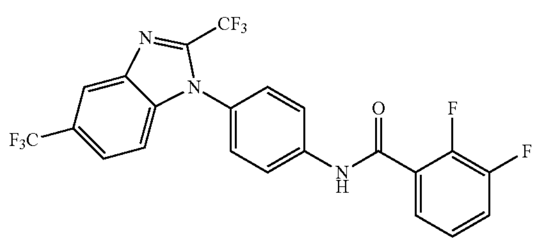 [SMILES: O=C(Nc1ccc(-n2c(C(F)(F)F)nc3cc(C(F)(F)F)ccc32)cc1)c1cccc(F)c1F] | 2,3-Difluoro-N-{4-[2,5-di-(trifluoromethyl)-benzoimidazol-1-yl]-phenyl}-benzamide |

-continued

| Compound No. | Structure | Chemical Name |
|---|---|---|
| 65 | 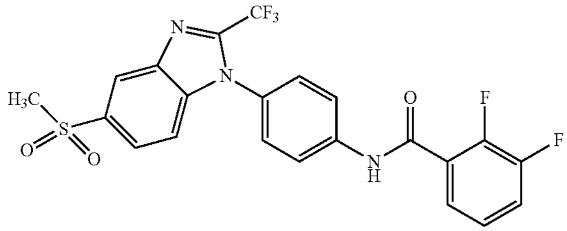 [SMILES: CS(=O)(=O)c1ccc2c(c1)nc(C(F)(F)F)n2-c1ccc(NC(=O)c2cccc(F)c2F)cc1] | 2,3-Difluoro-N-[4-(2-trifluoromethyl-5-methanesulfonyl-benzoimidazol-1-yl)-phenyl]-benzamide |
| 66 | 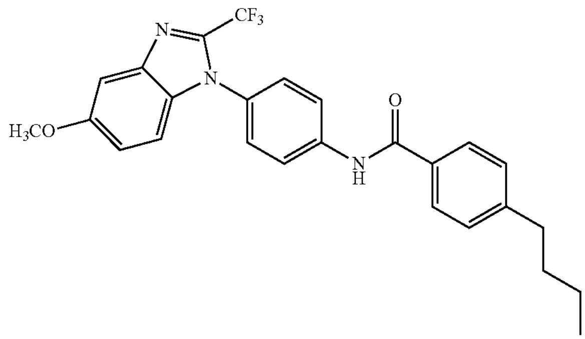 [SMILES: CCCCc1ccc(C(=O)Nc2ccc(-n3c(C(F)(F)F)nc4cc(OC)ccc43)cc2)cc1] | 4-Butyl-N-[4-(2-trifluoromethyl-5-methoxy-benzoimidazol-1-yl)-phenyl]-benzamide |
| 67 | 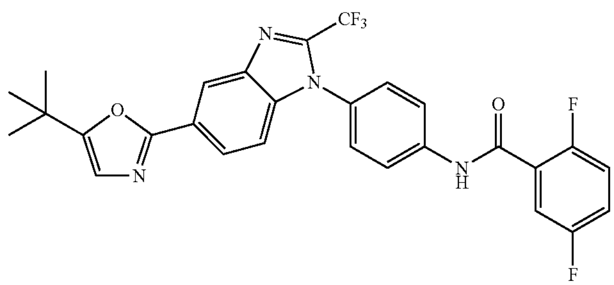 [SMILES: CC(C)(C)c1cnc(-c2ccc3c(c2)nc(C(F)(F)F)n3-c2ccc(NC(=O)c3cc(F)ccc3F)cc2)o1] | 2,5-Difluoro-N-{4-[2-trifluoromethyl-5-(5-tert-butyl-oxazol-2-yl)-benzoimidazol-1-yl]-phenyl}-benzamide |
| 68 | 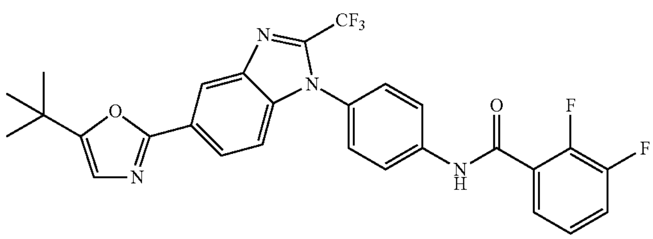 [SMILES: CC(C)(C)c1cnc(-c2ccc3c(c2)nc(C(F)(F)F)n3-c2ccc(NC(=O)c3cccc(F)c3F)cc2)o1] | 2,3-Difluoro-N-{4-[2-trifluoromethyl-5-(5-tert-butyl-oxazol-2-yl)-benzoimidazol-1-yl]-phenyl}-benzamide |
| 69 | 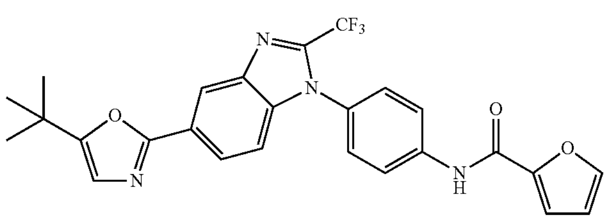 [SMILES: CC(C)(C)c1cnc(-c2ccc3c(c2)nc(C(F)(F)F)n3-c2ccc(NC(=O)c3ccco3)cc2)o1] | Furan-2-carboxylic acid (N-{4-[2-trifluoromethyl-5-(5-tert-butyl-oxazol-2-yl)-benzoimidazol-1-yl]-phenyl}) amide |
| 70 | 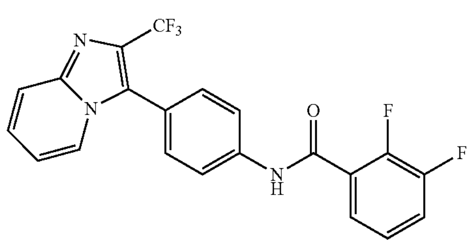 [SMILES: O=C(Nc1ccc(-c2c(C(F)(F)F)nc3ccccn23)cc1)c1cccc(F)c1F] | 2,3-Difluoro-N-[4-(2-trifluoromethyl-imidazo[1,2-a]pyrid-3-yl)-phenyl]-benzamide |

-continued

| Compound No. | Structure | Chemical Name |
|---|---|---|
| 71 | 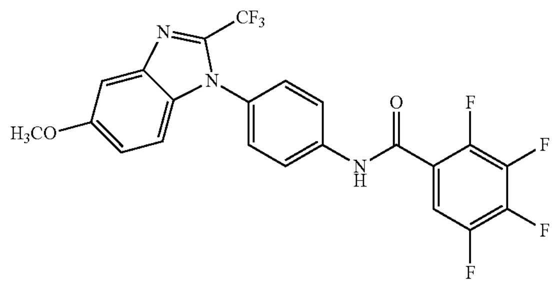 [SMILES: COc1ccc2c(c1)nc(C(F)(F)F)n2-c1ccc(NC(=O)c2cc(F)c(F)c(F)c2F)cc1] | 2,3,4,5-Tetrafluoro-N-[4-(2-trifluoromethyl-5-methoxy-benzoimidazol-1-yl)phenyl]-benzamide |
| 72 | 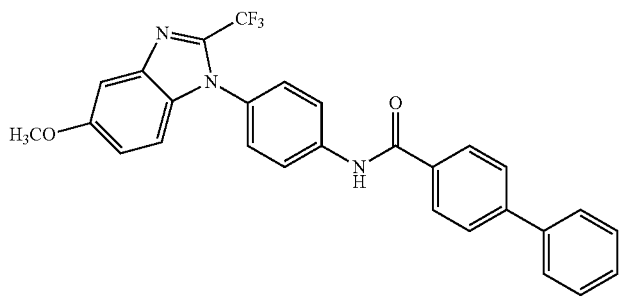 [SMILES: COc1ccc2c(c1)nc(C(F)(F)F)n2-c1ccc(NC(=O)c2ccc(-c3ccccc3)cc2)cc1] | 4-Phenyl-N-[4-(2-trifluoromethyl-5-methoxy-benzoimidazol-1-yl)-phenyl]-benzamide |
| 73 | 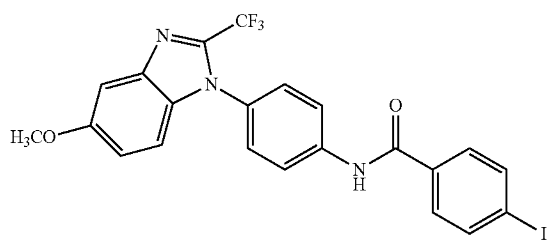 [SMILES: COc1ccc2c(c1)nc(C(F)(F)F)n2-c1ccc(NC(=O)c2ccc(I)cc2)cc1] | 4-Iodo-N-[4-(2-trifluoromethyl-5-methoxy-benzoimidazol-1-yl)-phenyl]-benzamide |
| 74 | 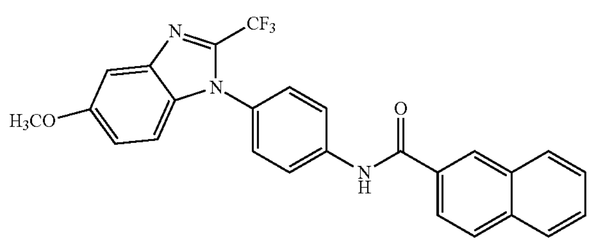 [SMILES: COc1ccc2c(c1)nc(C(F)(F)F)n2-c1ccc(NC(=O)c2ccc3ccccc3c2)cc1] | Naphthalene-2-carboxylic acid {N-[4-(2-trifluoromethyl-5-methoxy-benzoimidazol-1-yl)-phenyl]} amide |
| 75 | 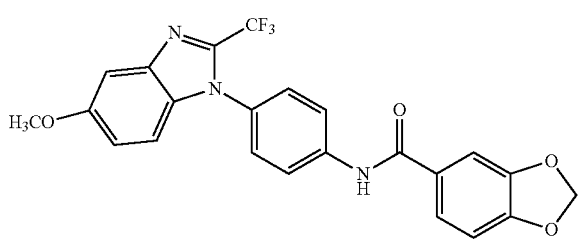 [SMILES: COc1ccc2c(c1)nc(C(F)(F)F)n2-c1ccc(NC(=O)c2ccc3c(c2)OCO3)cc1] | Benzo[1,3]dioxole-5-carboxylic acid {N-[4-(2-trifluoromethyl-5-methoxy-benzoimidazol-1-yl)-phenyl]} amide |
| 76 | 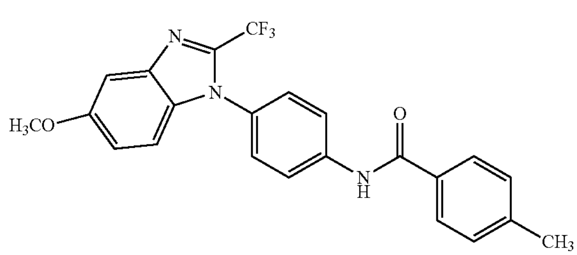 [SMILES: COc1ccc2c(c1)nc(C(F)(F)F)n2-c1ccc(NC(=O)c2ccc(C)cc2)cc1] | 4-Methyl-N-[4-(2-trifluoromethyl-5-methoxy-benzoimidazol-1-yl)-phenyl]-benzamide |

-continued

| Compound No. | Structure | Chemical Name |
|---|---|---|
| 77 | 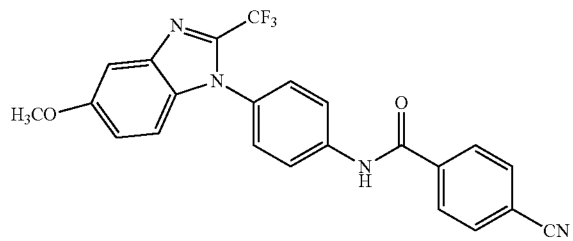 [SMILES: COc1ccc2c(c1)nc(C(F)(F)F)n2-c1ccc(NC(=O)c2ccc(C#N)cc2)cc1] | 4-Cyano-N-[4-(2-trifluoromethyl-5-methoxy-benzoimidazol-1-yl)-phenyl]-benzamide |
| 78 | 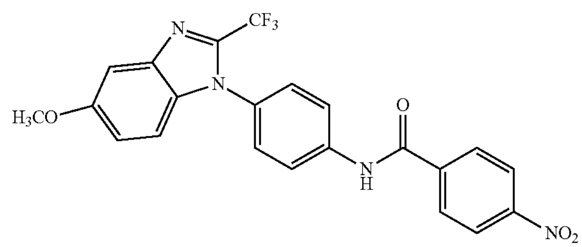 [SMILES: COc1ccc2c(c1)nc(C(F)(F)F)n2-c1ccc(NC(=O)c2ccc([N+](=O)[O-])cc2)cc1] | 4-Nitro-N-[4-(2-trifluoromethyl-5-methoxy-benzoimidazol-1-yl)-phenyl]-benzamide |
| 79 | 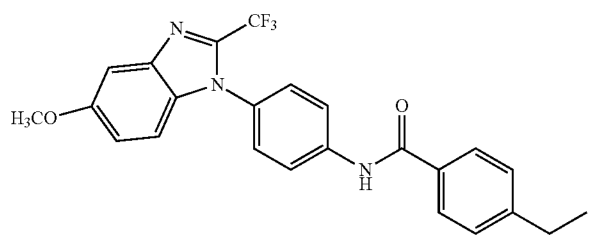 [SMILES: CCc1ccc(C(=O)Nc2ccc(-n3c(C(F)(F)F)nc4cc(OC)ccc43)cc2)cc1] | 4-Ethyl-N-[4-(2-trifluoromethyl-5-methoxy-benzoimidazol-1-yl)-phenyl]-benzamide |
| 80 | 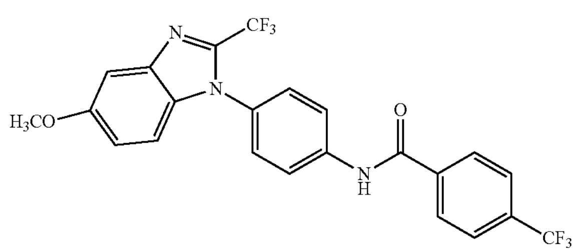 [SMILES: COc1ccc2c(c1)nc(C(F)(F)F)n2-c1ccc(NC(=O)c2ccc(C(F)(F)F)cc2)cc1] | 4-Trifluoromethyl-N-[4-(2-trifluoromethyl-5-methoxy-benzoimidazol-1-yl)-phenyl]-benzamide |
| 81 | 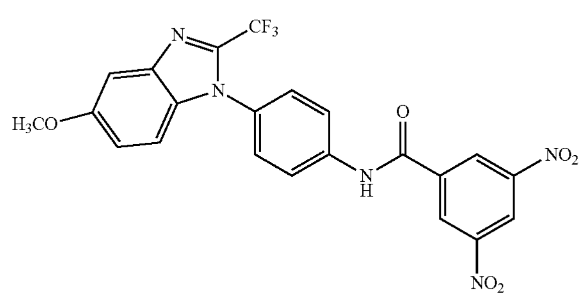 [SMILES: COc1ccc2c(c1)nc(C(F)(F)F)n2-c1ccc(NC(=O)c2cc([N+](=O)[O-])cc([N+](=O)[O-])c2)cc1] | 3,5-Dinitro-N-[4-(2-trifluoromethyl-5-methoxy-benzoimidazol-1-yl)-phenyl]-benzamide |
| 82 | 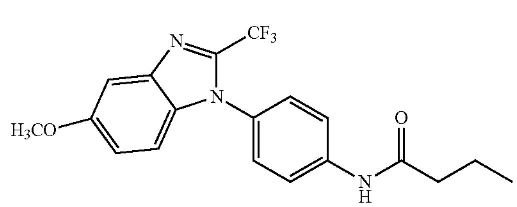 [SMILES: CCCC(=O)Nc1ccc(-n2c(C(F)(F)F)nc3cc(OC)ccc32)cc1] | N-[4-(2-trifluoromethyl-5-methoxy-benzoimidazol-1-yl)-phenyl]-butyramide |

-continued

| Compound No. | Structure | Chemical Name |
|---|---|---|
| 83 | 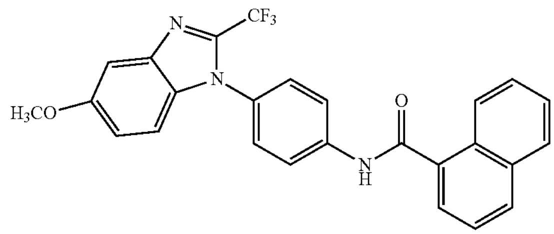 [SMILES: COc1ccc2c(c1)nc(C(F)(F)F)n2-c1ccc(NC(=O)c2cccc3ccccc23)cc1] | Naphthalene-1-carboxylic acid {N-[4-(2-trifluoromethyl-5-methoxy-benzoimidazol-1-yl)-phenyl]} amide |
| 84 | 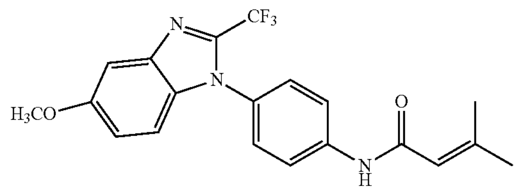 [SMILES: COc1ccc2c(c1)nc(C(F)(F)F)n2-c1ccc(NC(=O)C=C(C)C)cc1] | 3-Methyl-N-[4-(2-trifluoromethyl-5-methoxy-benzoimidazol-1-yl)-phenyl]-but-2-enoic acid amide |
| 85 | 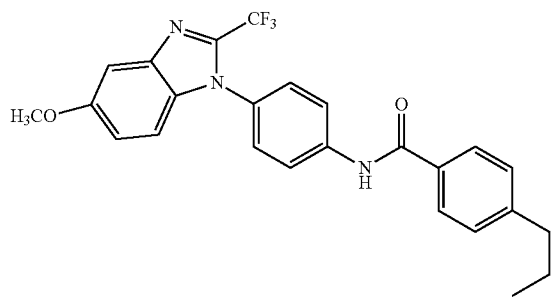 [SMILES: CCCc1ccc(C(=O)Nc2ccc(-n3c(C(F)(F)F)nc4cc(OC)ccc43)cc2)cc1] | 4-Propyl-N-[4-(2-trifluoromethyl-5-methoxy-benzoimidazol-1-yl)-phenyl]-benzamide |
| 86 | 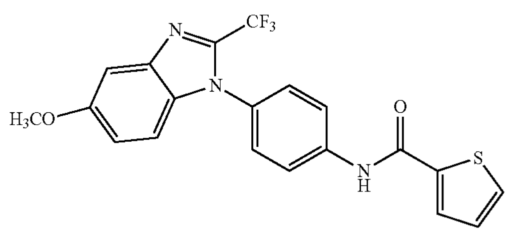 [SMILES: COc1ccc2c(c1)nc(C(F)(F)F)n2-c1ccc(NC(=O)c2cccs2)cc1] | Thiophene-2-carboxylic acid {N-[4-(2-trifluoromethyl-5-methoxy-benzoimidazol-1-yl)-phenyl]} amide |
| 87 | 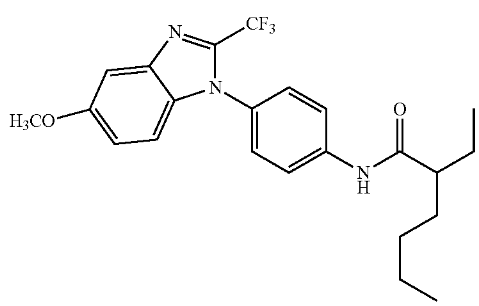 [SMILES: CCCCC(CC)C(=O)Nc1ccc(-n2c(C(F)(F)F)nc3cc(OC)ccc32)cc1] | 2-Ethyl-N-[4-(2-trifluoromethyl-5-methoxy-benzoimidazol-1-yl)-phenyl]-hexanoic acid amide |
| 88 | 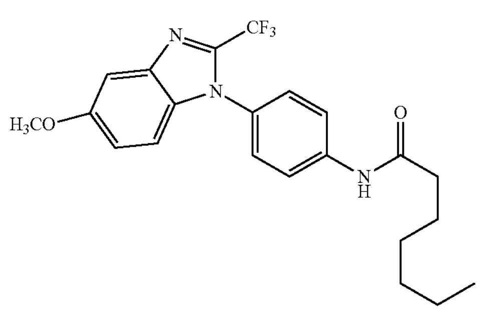 [SMILES: CCCCCCC(=O)Nc1ccc(-n2c(C(F)(F)F)nc3cc(OC)ccc32)cc1] | N-[4-(2-trifluoromethyl-5-methoxy-benzoimidazol-1-yl)-phenyl]-heptanoic acid amide |

| Compound No. | Structure | Chemical Name |
|---|---|---|
| 89 | 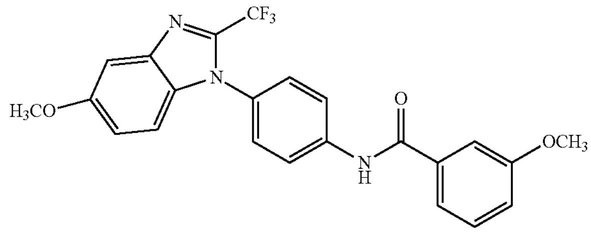 [SMILES: COc1cccc(C(=O)Nc2ccc(-n3c(C(F)(F)F)nc4cc(OC)ccc43)cc2)c1] | 3-Methoxy-N-[4-(2-trifluoromethyl-5-methoxy-benzoimidazol-1-yl)-phenyl]-benzamide |
| 90 | 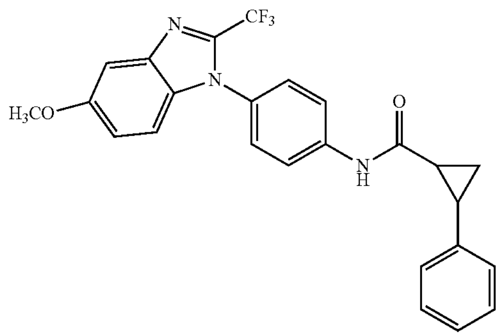 [SMILES: COc1ccc2c(c1)nc(C(F)(F)F)n2-c1ccc(NC(=O)C2CC2c2ccccc2)cc1] | 2-Phenyl-N-[4-(2-trifluoromethyl-5-methoxy-benzoimidazol-1-yl)-phenyl]-cyclopropanecarboxylic acid amide |
| 91 | 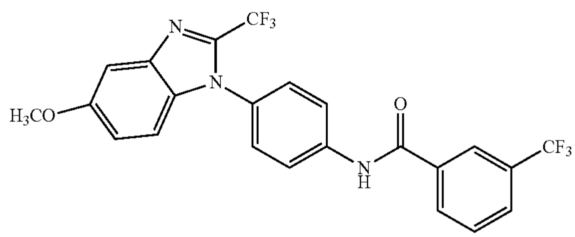 [SMILES: COc1ccc2c(c1)nc(C(F)(F)F)n2-c1ccc(NC(=O)c2cccc(C(F)(F)F)c2)cc1] | 3-Trifluoromethyl-N-[4-(2-trifluoromethyl-5-methoxy-benzoimidazol-1-yl)-phenyl]-benzamide |
| 92 | 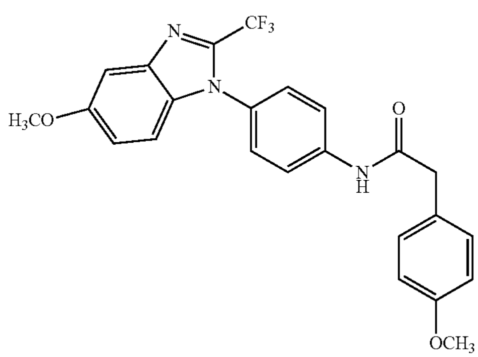 [SMILES: COc1ccc(CC(=O)Nc2ccc(-n3c(C(F)(F)F)nc4cc(OC)ccc43)cc2)cc1] | 2-(4-Methoxy-phenyl)-N-[4-(2-trifluoromethyl-5-methoxy-benzoimidazol-1-yl)-phenyl]-acetamide |
| 93 | 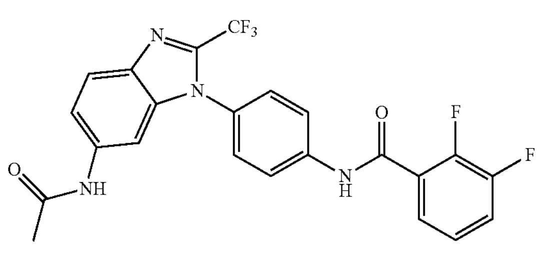 [SMILES: CC(=O)Nc1ccc2nc(C(F)(F)F)n(-c3ccc(NC(=O)c4cccc(F)c4F)cc3)c2c1] | 2,3-Difluoro-N-[4-(2-trifluoromethyl-6-acetylamino-benzoimidazol-1-yl)-phenyl]-benzamide |

-continued

| Compound No. | Structure | Chemical Name |
|---|---|---|
| 94 | 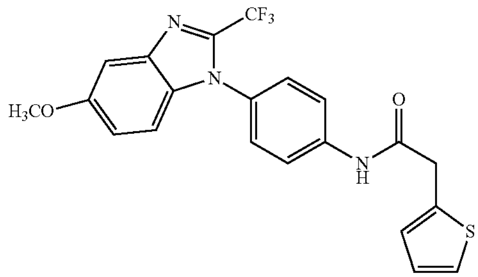 [SMILES: COc1ccc2c(c1)nc(C(F)(F)F)n2-c1ccc(NC(=O)Cc2cccs2)cc1] | 2-(Thien-2-yl)-N-[4-(2-trifluoromethyl-5-methoxy-benzoimidazol-1-yl)-phenyl]-acetamide |
| 95 | 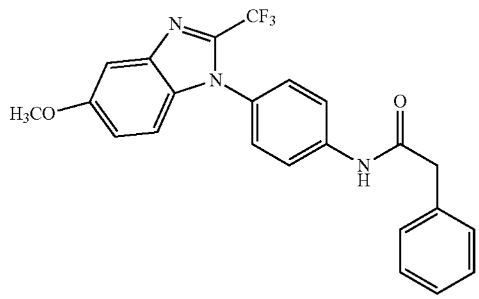 [SMILES: COc1ccc2c(c1)nc(C(F)(F)F)n2-c1ccc(NC(=O)Cc2ccccc2)cc1] | 2-phenyl-N-[4-(2-trifluoromethyl-5-methoxy-benzoimidazol-1-yl)-phenyl]-acetamide |
| 96 | 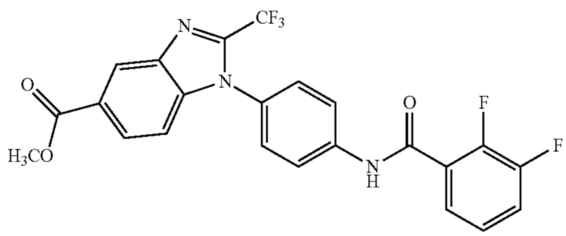 [SMILES: COC(=O)c1ccc2c(c1)nc(C(F)(F)F)n2-c1ccc(NC(=O)c2cccc(F)c2F)cc1] | 2-Trifluoromethyl-1-[4-(2,3-difluoro-benzoylamimo)-phenyl]-1H-benzoimidazole-5-carboxylic acid methyl ester |
| 97 | 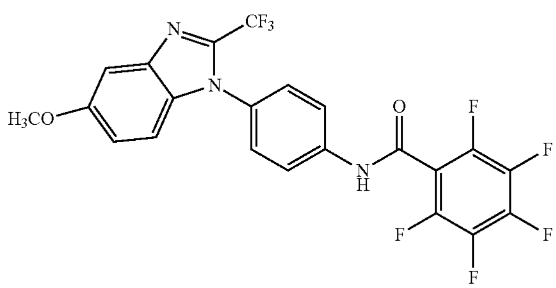 [SMILES: COc1ccc2c(c1)nc(C(F)(F)F)n2-c1ccc(NC(=O)c2c(F)c(F)c(F)c(F)c2F)cc1] | 2,3,4,5,6-Pentafluoro-N-[4-(2-trifluoromethyl-5-methoxy-benzoimidazol-1-yl)-phenyl]-benzamide |
| 98 | 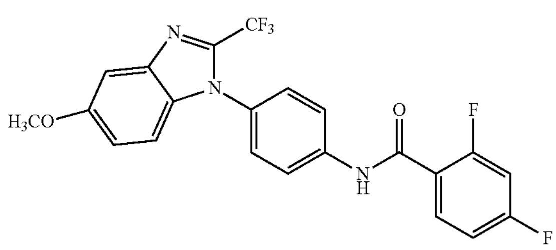 [SMILES: COc1ccc2c(c1)nc(C(F)(F)F)n2-c1ccc(NC(=O)c2ccc(F)cc2F)cc1] | 2,4-Difluoro-N-[4-(2-trifluoromethyl-5-methoxy-benzoimidazol-1-yl)-phenyl]-benzamide |
| 99 | 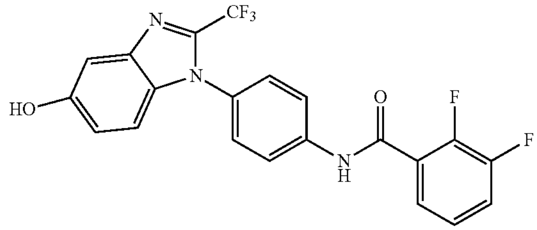 [SMILES: O=C(Nc1ccc(-n2c(C(F)(F)F)nc3cc(O)ccc32)cc1)c1cccc(F)c1F] | 2,3-Difluoro-N-[4-(2-trifluoromethyl-5-hydroxy-benzoimidazol-1-yl)-phenyl]-benzamide |

| Compound No. | Structure | Chemical Name |
|---|---|---|
| 100 | 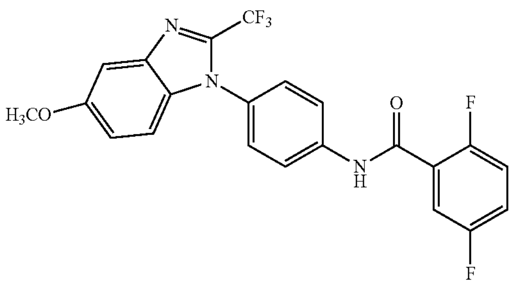 [SMILES: COc1ccc2c(c1)nc(C(F)(F)F)n2-c1ccc(NC(=O)c2cc(F)ccc2F)cc1] | 2,5-Difluoro-N-[4-(2-trifluoromethyl-5-methoxy-benzoimidazol-1-yl)-phenyl]-benzamide |
| 101 | 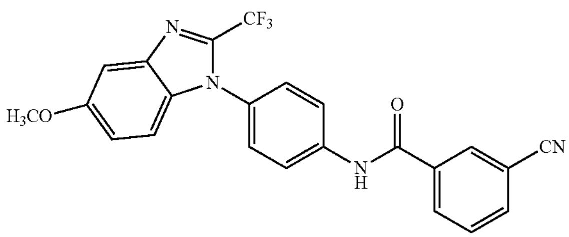 [SMILES: COc1ccc2c(c1)nc(C(F)(F)F)n2-c1ccc(NC(=O)c2cccc(C#N)c2)cc1] | 3-Cyano-N-[4-(2-trifluoromethyl-5-methoxy-benzoimidazol-1-yl)-phenyl]-benzamide |
| 102 | 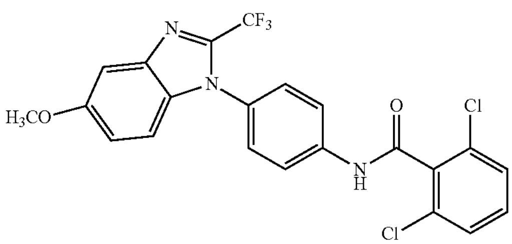 [SMILES: COc1ccc2c(c1)nc(C(F)(F)F)n2-c1ccc(NC(=O)c2c(Cl)cccc2Cl)cc1] | 2,6-Dichloro-N-[4-(2-trifluoromethyl-5-methoxy-benzoimidazol-1-yl)-phenyl]-benzamide |
| 103 | 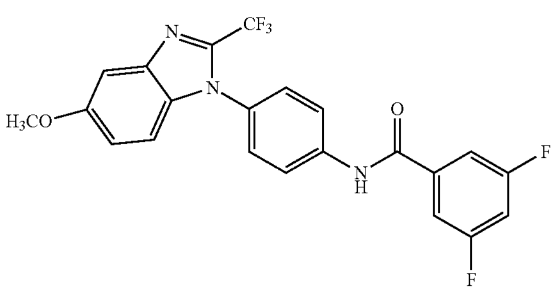 [SMILES: COc1ccc2c(c1)nc(C(F)(F)F)n2-c1ccc(NC(=O)c2cc(F)cc(F)c2)cc1] | 3,5-Dichloro-N-[4-(2-trifluoromethyl-5-methoxy-benzoimidazol-1-yl)-phenyl]-benzamide |
| 104 | 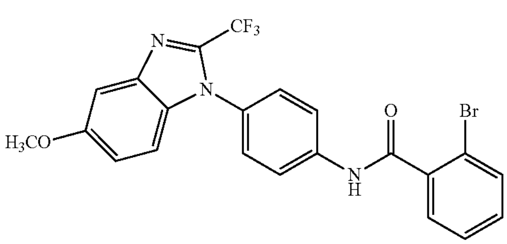 [SMILES: COc1ccc2c(c1)nc(C(F)(F)F)n2-c1ccc(NC(=O)c2ccccc2Br)cc1] | 2-Bromo-N-[4-(2-trifluoromethyl-5-methoxy-benzoimidazol-1-yl)-phenyl]-benzamide |
| 105 | 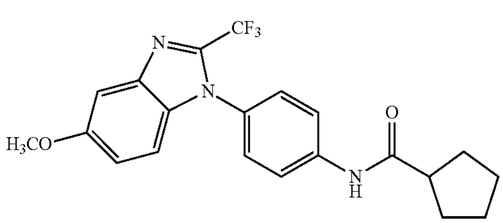 [SMILES: COc1ccc2c(c1)nc(C(F)(F)F)n2-c1ccc(NC(=O)C2CCCC2)cc1] | N-[4-(2-trifluoromethyl-5-methoxy-benzoimidazol-1-yl)-phenyl]-cyclopentanecarboxylic acid amide |

-continued

| Compound No. | Structure | Chemical Name |
| --- | --- | --- |
| 106 | 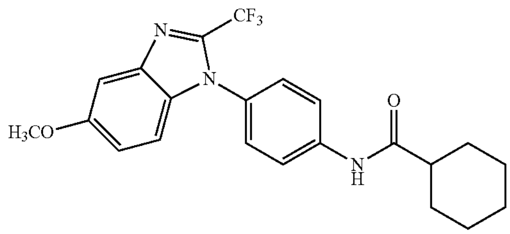 [SMILES: COc1ccc2c(c1)nc(C(F)(F)F)n2-c1ccc(NC(=O)C2CCCCC2)cc1] | N-[4-(2-trifluoromethyl-5-methoxy-benzoimidazol-1-yl)-phenyl]-cyclohexanecarboxylic acid amide |
| 107 | 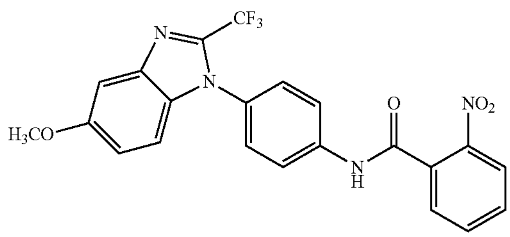 [SMILES: COc1ccc2c(c1)nc(C(F)(F)F)n2-c1ccc(NC(=O)c2ccccc2[N+](=O)[O-])cc1] | 2-Nitro-N-[4-(2-trifluoromethyl-5-methoxy-benzoimidazol-1-yl)-phenyl]-benzamide |
| 108 | 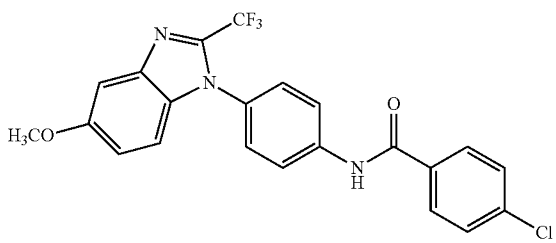 [SMILES: COc1ccc2c(c1)nc(C(F)(F)F)n2-c1ccc(NC(=O)c2ccc(Cl)cc2)cc1] | 4-Chloro-N-[4-(2-trifluoromethyl-5-methoxy-benzoimidazol-1-yl)-phenyl]-benzamide |
| 109 | 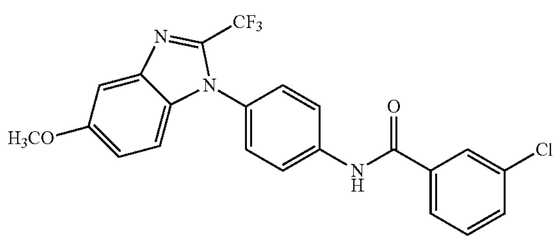 [SMILES: COc1ccc2c(c1)nc(C(F)(F)F)n2-c1ccc(NC(=O)c2cccc(Cl)c2)cc1] | 3-Chloro-N-[4-(2-trifluoromethyl-5-methoxy-benzoimidazol-1-yl)-phenyl]-benzamide |
| 110 | 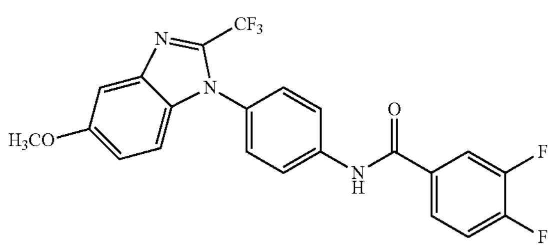 [SMILES: COc1ccc2c(c1)nc(C(F)(F)F)n2-c1ccc(NC(=O)c2ccc(F)c(F)c2)cc1] | 3,4-Difluoro-N-[4-(2-trifluoromethyl-5-methoxy-benzoimidazol-1-yl)-phenyl]-benzamide |
| 111 | 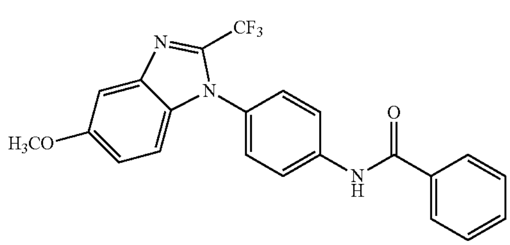 [SMILES: COc1ccc2c(c1)nc(C(F)(F)F)n2-c1ccc(NC(=O)c2ccccc2)cc1] | N-[4-(2-trifluoromethyl-5-methoxy-benzoimidazol-1-yl)-phenyl]-benzamide |

| Compound No. | Structure | Chemical Name |
|---|---|---|
| 112 | 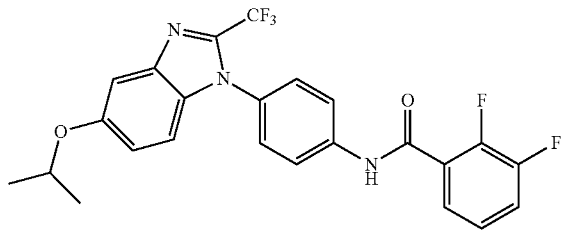 [SMILES: CC(C)Oc1ccc2c(c1)nc(C(F)(F)F)n2-c1ccc(NC(=O)c2cccc(F)c2F)cc1] | 2,3-Difluoro-N-[4-(2-trifluoromethyl-5-isopropoxy-benzoimidazol-1-yl)-phenyl]-benzamide |
| 113 | 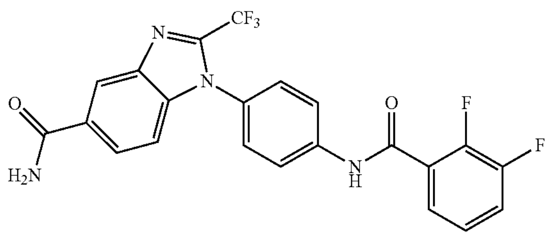 [SMILES: NC(=O)c1ccc2c(c1)nc(C(F)(F)F)n2-c1ccc(NC(=O)c2cccc(F)c2F)cc1] | 2,3-Difluoro-N-[4-(2-trifluoromethyl-5-carbamoyl-benzoimidazol-1-yl)-phenyl]-benzamide |
| 114 | 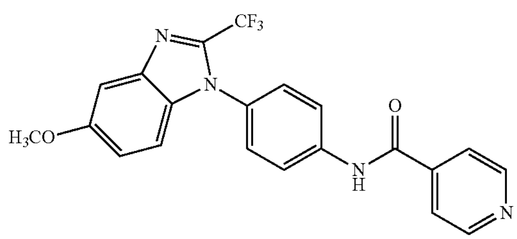 [SMILES: COc1ccc2c(c1)nc(C(F)(F)F)n2-c1ccc(NC(=O)c2ccncc2)cc1] | N-[4-(2-trifluoromethyl-5-methoxy-benzoimidazol-1-yl)-phenyl]-isonicotinamide |
| 115 | 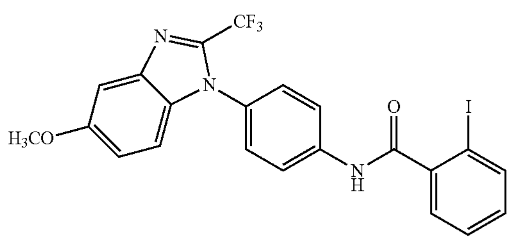 [SMILES: COc1ccc2c(c1)nc(C(F)(F)F)n2-c1ccc(NC(=O)c2ccccc2I)cc1] | 2-Iodo-N-[4-(2-trifluoromethyl-5-methoxy-benzoimidazol-1-yl)-phenyl]-benzamide |
| 116 | 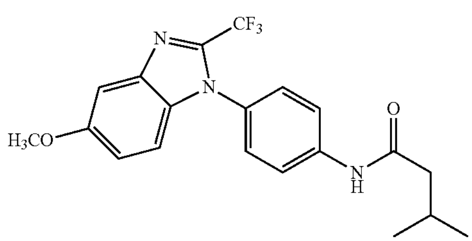 [SMILES: COc1ccc2c(c1)nc(C(F)(F)F)n2-c1ccc(NC(=O)CC(C)C)cc1] | 3-Methyl-N-[4-(2-trifluoromethyl-5-methoxy-benzoimidazol-1-yl)-phenyl]-butyramide |
| 117 | 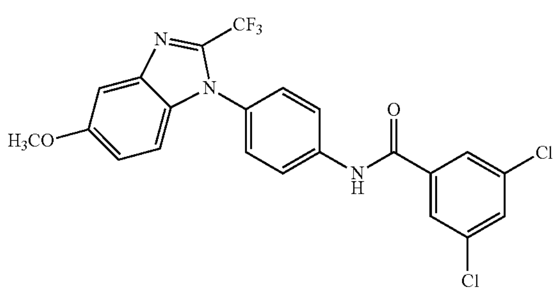 [SMILES: COc1ccc2c(c1)nc(C(F)(F)F)n2-c1ccc(NC(=O)c2cc(Cl)cc(Cl)c2)cc1] | 3,5-Dichloro-N-[4-(2-trifluoromethyl-5-methoxy-benzoimidazol-1-yl)-phenyl]-benzamide |

-continued

| Compound No. | Structure | Chemical Name |
|---|---|---|
| 118 | 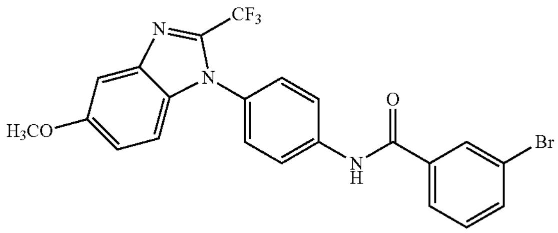 [SMILES: COc1ccc2c(c1)nc(C(F)(F)F)n2-c1ccc(NC(=O)c2cccc(Br)c2)cc1] | 3-Bromo-N-[4-(2-trifluoromethyl-5-methoxy-benzoimidazol-1-yl)-phenyl]-benzamide |
| 119 | 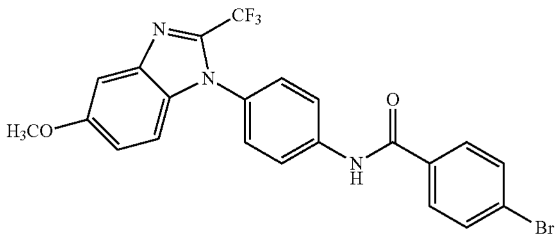 [SMILES: COc1ccc2c(c1)nc(C(F)(F)F)n2-c1ccc(NC(=O)c2ccc(Br)cc2)cc1] | 4-Bromo-N-[4-(2-trifluoromethyl-5-methoxy-benzoimidazol-1-yl)-phenyl]-benzamide |
| 120 | 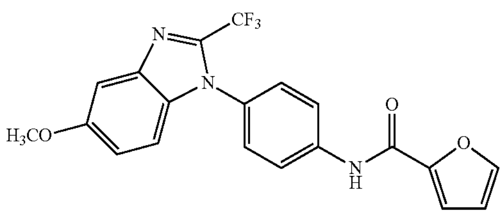 [SMILES: COc1ccc2c(c1)nc(C(F)(F)F)n2-c1ccc(NC(=O)c2ccco2)cc1] | Furan-2-carboxylic acid {N-[4-(2-trifluoromethyl-5-methoxy-benzoimidazol-1-yl)-phenyl]}-amide |
| 121 | 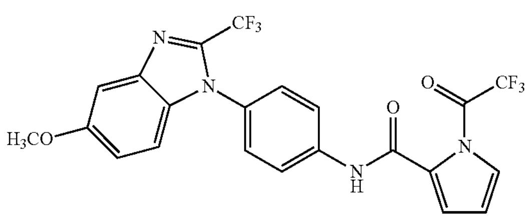 [SMILES: COc1ccc2c(c1)nc(C(F)(F)F)n2-c1ccc(NC(=O)c2cccn2C(=O)C(F)(F)F)cc1] | 1-(2,2,2-Trifluoroacetyl)-N-[4-(2-trifluoromethyl-5-methoxy-benzoimidazol-1-yl)-phenyl]-pyrrolidine-2-carboxylic acid amide |
| 122 | 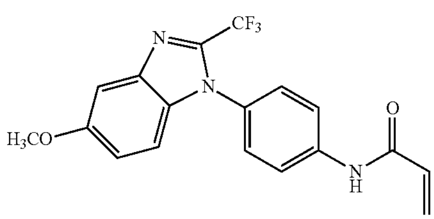 [SMILES: C=CC(=O)Nc1ccc(-n2c(C(F)(F)F)nc3cc(OC)ccc32)cc1] | N-[4-(2-trifluoromethyl-5-methoxy-benzoimidazol-1-yl)-phenyl]-acrylamide |
| 123 | 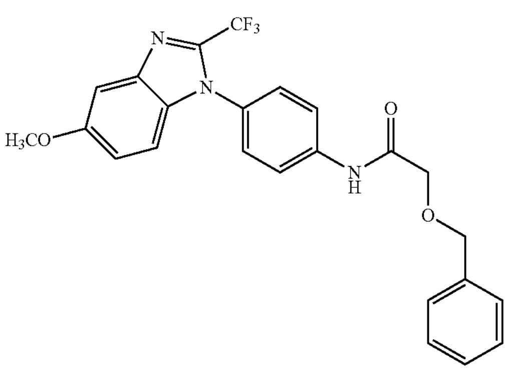 [SMILES: COc1ccc2c(c1)nc(C(F)(F)F)n2-c1ccc(NC(=O)COCc2ccccc2)cc1] | 2-Benzyloxy-N-[4-(2-trifluoromethyl-5-methoxy-benzoimidazol-1-yl)-phenyl]-acetamide |

-continued

| Compound No. | Structure | Chemical Name |
|---|---|---|
| 124 | 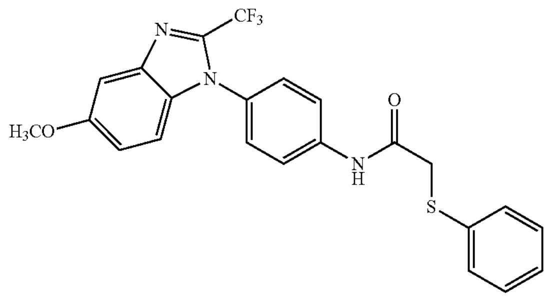 [SMILES: COc1ccc2c(c1)nc(C(F)(F)F)n2-c1ccc(NC(=O)CSc2ccccc2)cc1] | 2-Phenylsulfanyl-N-[4-(2-trifluoromethyl-5-methoxy-benzoimidazol-1-yl)-phenyl]-acetamide |
| 125 | 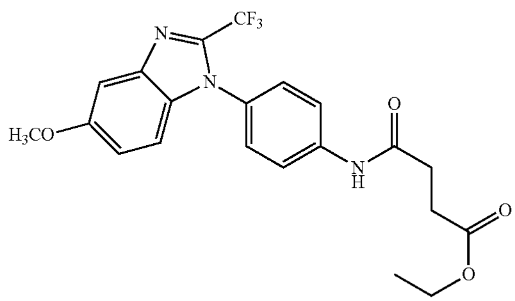 [SMILES: CCOC(=O)CCC(=O)Nc1ccc(-n2c(C(F)(F)F)nc3cc(OC)ccc32)cc1] | N-[4-(2-trifluoromethyl-5-methoxy-benzoimidazol-1-yl)-phenyl]-succinamic acid ethyl ester |
| 126 | 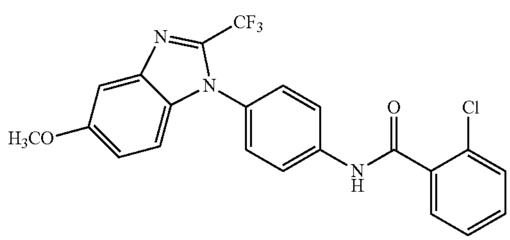 [SMILES: COc1ccc2c(c1)nc(C(F)(F)F)n2-c1ccc(NC(=O)c2ccccc2Cl)cc1] | 2-Chloro-N-[4-(2-trifluoromethyl-5-methoxy-benzoimidazol-1-yl)-phenyl]-benzamide |
| 127 | 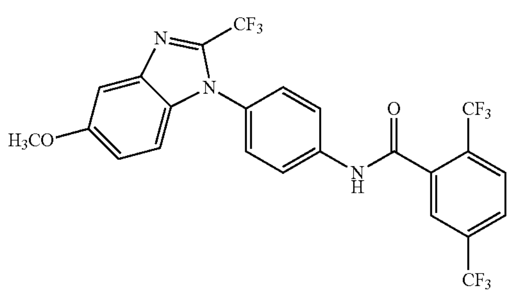 [SMILES: COc1ccc2c(c1)nc(C(F)(F)F)n2-c1ccc(NC(=O)c2cc(C(F)(F)F)ccc2C(F)(F)F)cc1] | 2,5-Di-(trifluoromethyl)-N-[4-(2-trifluoromethyl-5-methoxy-benzoimidazol-1-yl)-phenyl]-benzamide |
| 128 | 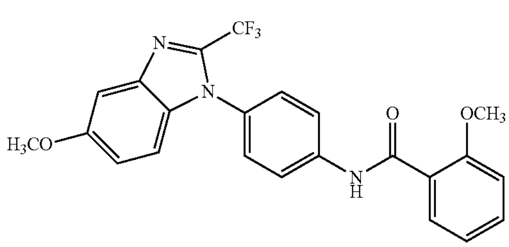 [SMILES: COc1ccc2c(c1)nc(C(F)(F)F)n2-c1ccc(NC(=O)c2ccccc2OC)cc1] | 2-Methoxy-N-[4-(2-trifluoromethyl-5-methoxy-benzoimidazol-1-yl)-phenyl]-benzamide |

-continued

| Compound No. | Structure | Chemical Name |
|---|---|---|
| 129 | 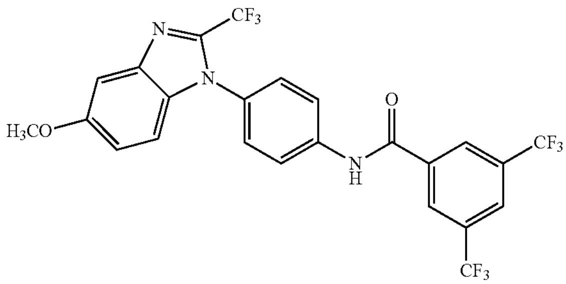 [SMILES: COc1ccc2c(c1)nc(C(F)(F)F)n2-c1ccc(NC(=O)c2cc(C(F)(F)F)cc(C(F)(F)F)c2)cc1] | 3,5-Di-(trifluoromethyl)-N-[4-(2-trifluoromethyl-5-methoxy-benzoimidazol-1-yl)-phenyl]-benzamide |
| 130 | 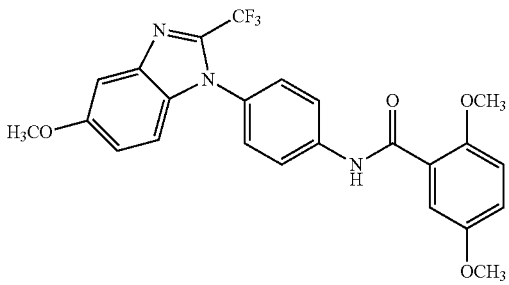 [SMILES: COc1ccc(OC)c(C(=O)Nc2ccc(-n3c(C(F)(F)F)nc4cc(OC)ccc43)cc2)c1] | 2,5-Dimethoxy-N-[4-(2-trifluoromethyl-5-methoxy-benzoimidazol-1-yl)-phenyl]-benzamide |
| 131 | 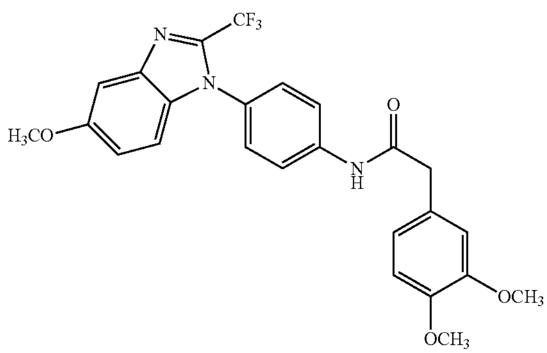 [SMILES: COc1ccc2c(c1)nc(C(F)(F)F)n2-c1ccc(NC(=O)Cc2ccc(OC)c(OC)c2)cc1] | 2-(3,4-dimethoxy-phenyl)-N-[4-(2-trifluoromethyl-5-methoxy-benzoimidazol-1-yl)-phenyl]-acetamide |
| 132 | 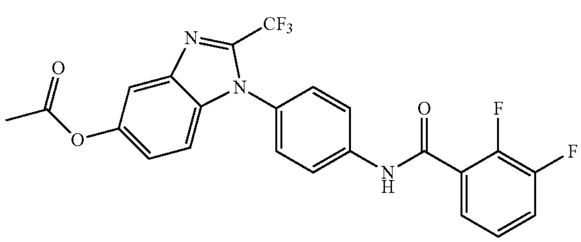 [SMILES: CC(=O)Oc1ccc2c(c1)nc(C(F)(F)F)n2-c1ccc(NC(=O)c2cccc(F)c2F)cc1] | 2,3-Difluoro-N-[4-(2-trifluoromethyl-5-acetoxy-benzoimidazol-1-yl)-phenyl]-benzamide |
| 133 | 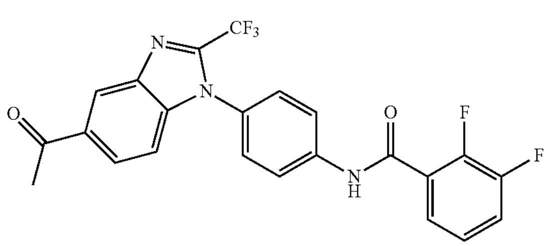 [SMILES: CC(=O)c1ccc2c(c1)nc(C(F)(F)F)n2-c1ccc(NC(=O)c2cccc(F)c2F)cc1] | 2,3-Difluoro-N-[4-(2-trifluoromethyl-5-acetyl-benzoimidazol-1-yl)-phenyl]-benzamide |

-continued

| Compound No. | Structure | Chemical Name |
|---|---|---|
| 134 | 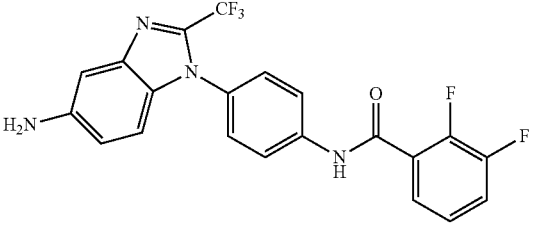 [SMILES: Nc1ccc2c(c1)nc(C(F)(F)F)n2-c1ccc(NC(=O)c2cccc(F)c2F)cc1] | 2,3-Difluoro-N-[4-(2-trifluoromethyl-5-amino-benzoimidazol-1-yl)-phenyl]-benzamide |
| 135 | 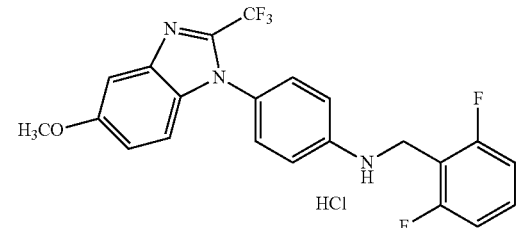 | 2,6-Difluoro-N-[4-(2-trifluoromethyl-5-methoxy-benzoimidazol-1-yl)-phenyl]-benzylamine, HCl salt |
| 136 | 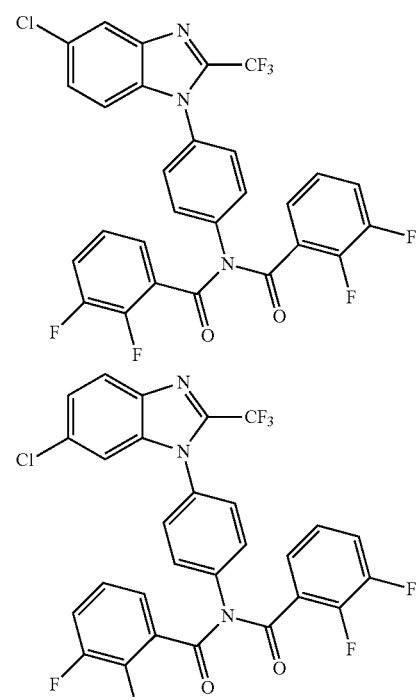 | Isomeric mixture of N-[4-(5-Chloro-2-trifluoromethyl-benzoimidazol-1-yl)-phenyl]-N-(2,3-difluoro-benzoyl)-2,3-difluoro-benzamide & N-[4-(6-Chloro-2-trifluoromethyl-benzoimidazol-1-yl)-phenyl]-N-(2,3-difluoro-benzoyl)-2,3-difluoro-benzamide |
| 137 | 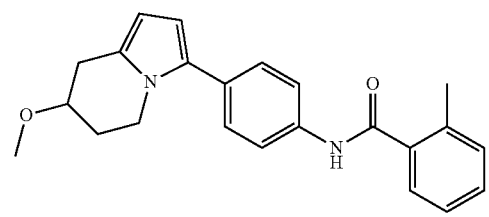 | 2-Methyl-N-[4-(7-methoxy-5,6,7,8-tetrahydroindolizin-3-yl)-phenyl]-benzamide |

-continued

| Compound No. | Structure | Chemical Name |
|---|---|---|
| 138 | 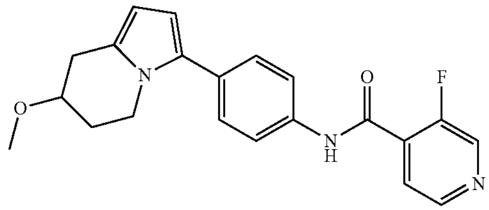 [SMILES: COC1CCn2c(ccc2-c2ccc(NC(=O)c3ccncc3F)cc2)C1] | 3-Methyl-N-[4-(7-methoxy-5,6,7,8-tetrahydroindolizin-3-yl)-phenyl]-isonicotinamide |
| 139 | 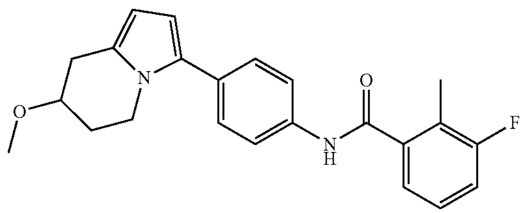 [SMILES: COC1CCn2c(ccc2-c2ccc(NC(=O)c3cccc(F)c3C)cc2)C1] | 2-Methyl-3-fluoro-N-[4-(7-methoxy-5,6,7,8-tetrahydroindolizin-3-yl)-phenyl]-benzamide |
| 140 | 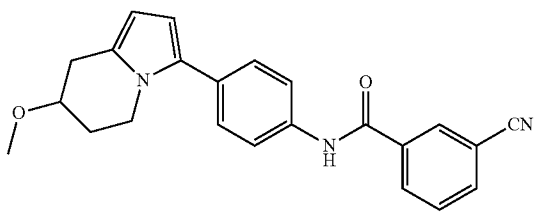 [SMILES: COC1CCn2c(ccc2-c2ccc(NC(=O)c3cccc(C#N)c3)cc2)C1] | 3-Cyano-N-[4-(7-methoxy-5,6,7,8-tetrahydroindolizin-3-yl)-phenyl]-benzamide |
| 141 | 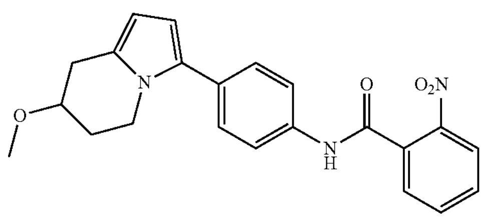 [SMILES: COC1CCn2c(ccc2-c2ccc(NC(=O)c3ccccc3[N+](=O)[O-])cc2)C1] | 2-Nitro-N-[4-(7-methoxy-5,6,7,8-tetrahydroindolizin-3-yl)-phenyl]-benzamide |
| 142 | 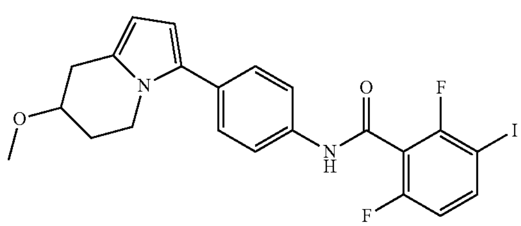 [SMILES: COC1CCn2c(ccc2-c2ccc(NC(=O)c3c(F)ccc(I)c3F)cc2)C1] | 2,6-Difluoro-3-iodo-N-[4-(7-methoxy-5,6,7,8-tetrahydroindolizin-3-yl)-phenyl]-benzamide |
| 143 | 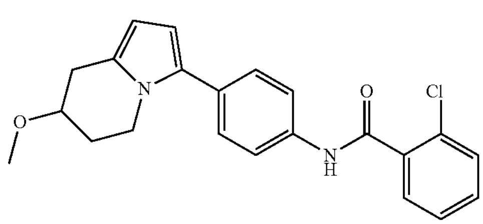 [SMILES: COC1CCn2c(ccc2-c2ccc(NC(=O)c3ccccc3Cl)cc2)C1] | 2-Chloro-N-[4-(7-methoxy-5,6,7,8-tetrahydroindolizin-3-yl)-phenyl]-benzamide |
| 144 | 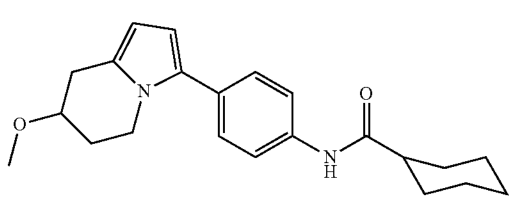 [SMILES: COC1CCn2c(ccc2-c2ccc(NC(=O)C3CCCCC3)cc2)C1] | N-[4-(7-methoxy-5,6,7,8-tetrahydroindolizin-3-yl)-phenyl]-cyclohexanecarboxylic acid amide |

-continued

| Compound No. | Structure | Chemical Name |
|---|---|---|
| 145 | 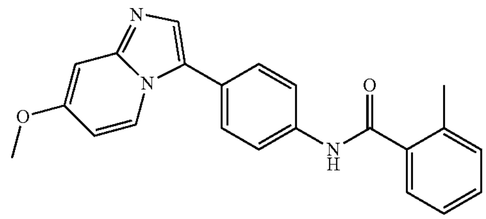 [SMILES: COc1ccn2c(-c3ccc(NC(=O)c4ccccc4C)cc3)cnc2c1] | 2-Methyl-N-[4-(7-methoxy-imidazo[1,2-a]pyrid-3-yl)-phenyl]-benzamide |
| 146 | 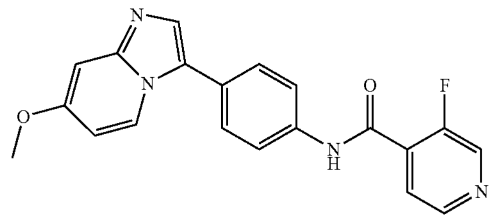 [SMILES: COc1ccn2c(-c3ccc(NC(=O)c4ccncc4F)cc3)cnc2c1] | 3-Fluoro-N-[4-(7-methoxy-imidazo[1,2-a]pyrid-3-yl)-phenyl]-isonicotinamide |
| 147 | 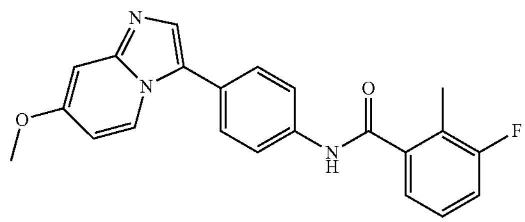 [SMILES: COc1ccn2c(-c3ccc(NC(=O)c4cccc(F)c4C)cc3)cnc2c1] | 2-Methyl-3-fluoro-N-[4-(7-methoxy-imidazo[1,2-a]pyrid-3-yl)-phenyl]-benzamide |
| 148 | 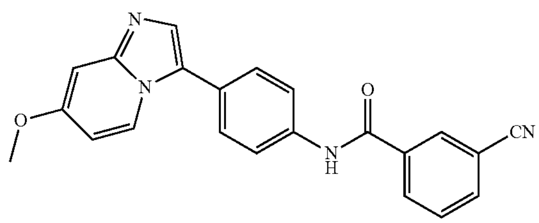 [SMILES: COc1ccn2c(-c3ccc(NC(=O)c4cccc(C#N)c4)cc3)cnc2c1] | 3-Cyano-N-[4-(7-methoxy-imidazo[1,2-a]pyrid-3-yl)-phenyl]-benzamide |
| 149 | 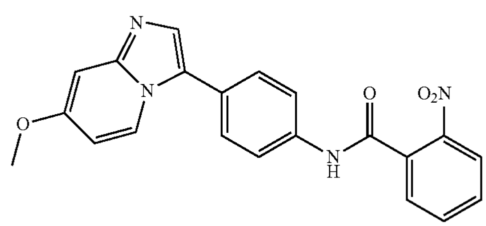 [SMILES: COc1ccn2c(-c3ccc(NC(=O)c4ccccc4[N+](=O)[O-])cc3)cnc2c1] | 3-Nitro-N-[4-(7-methoxy-imidazo[1,2-a]pyrid-3-yl)-phenyl]-benzamide |
| 150 | 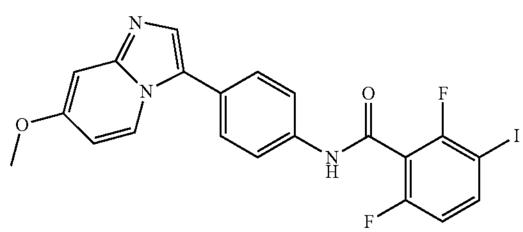 [SMILES: COc1ccn2c(-c3ccc(NC(=O)c4c(F)ccc(I)c4F)cc3)cnc2c1] | 2,6-Difluoro-3-iodo-N-[4-(7-methoxy-imidazo[1,2-a]pyrid-3-yl)-phenyl]-benzamide |
| 151 | 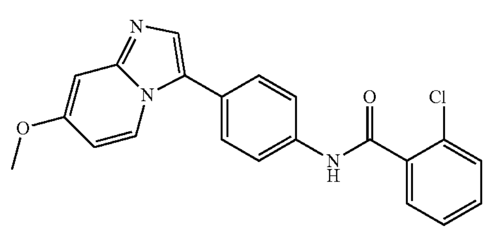 | 2-Chloro-N-[4-(7-methoxy-imidazo[1,2-a]pyrid-3-yl)-phenyl]-benzamide |

-continued

| Compound No. | Structure | Chemical Name |
|---|---|---|
| 152 | 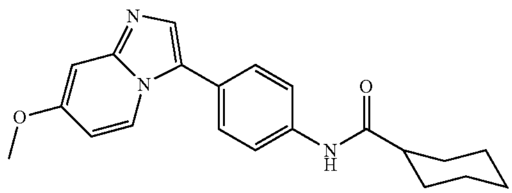 [SMILES: COc1ccn2c(-c3ccc(NC(=O)C4CCCCC4)cc3)cnc2c1] | N-[4-(7-methoxy-imidazo[1,2-a]pyrid-3-yl)-phenyl]-cyclohexanecarboxylic acid amide |
| 153 | 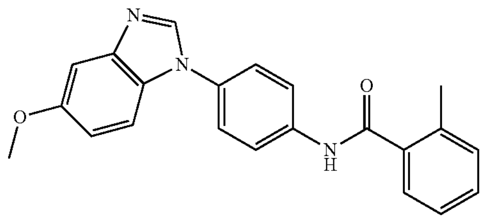 [SMILES: COc1ccc2c(c1)ncn2-c1ccc(NC(=O)c2ccccc2C)cc1] | 2-Methyl-N-[4-(5-methoxy-benzoimidazol-1-yl)-phenyl]-benzamide |
| 154 | 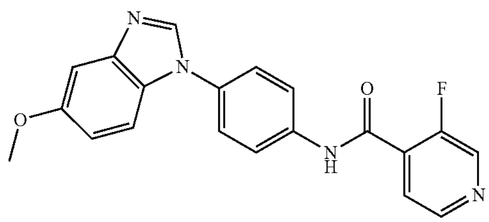 [SMILES: COc1ccc2c(c1)ncn2-c1ccc(NC(=O)c2ccncc2F)cc1] | 2-Fluoro-N-[4-(5-methoxy-benzoimidazol-1-yl)-phenyl]-isonicotinamide |
| 156 | 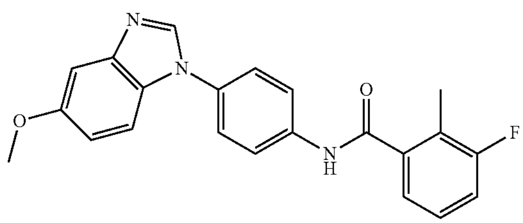 [SMILES: COc1ccc2c(c1)ncn2-c1ccc(NC(=O)c2cccc(F)c2C)cc1] | 2-Methyl-3-fluoro-N-[4-(5-methoxy-benzoimidazol-1-yl)-phenyl]-benzamide |
| 157 | 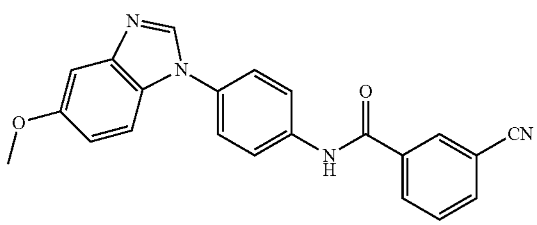 [SMILES: COc1ccc2c(c1)ncn2-c1ccc(NC(=O)c2cccc(C#N)c2)cc1] | 3-Cyano-N-[4-(5-methoxy-benzoimidazol-1-yl)-phenyl]-benzamide |
| 158 | 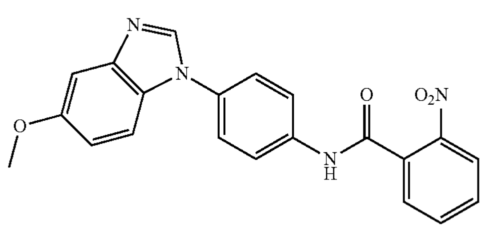 [SMILES: COc1ccc2c(c1)ncn2-c1ccc(NC(=O)c2ccccc2[N+](=O)[O-])cc1] | 2-Nitro-N-[4-(5-methoxy-benzoimidazol-1-yl)-phenyl]-benzamide |
| 159 | 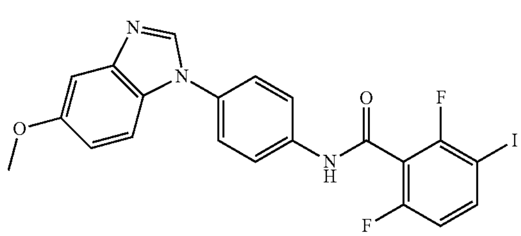 [SMILES: COc1ccc2c(c1)ncn2-c1ccc(NC(=O)c2c(F)ccc(I)c2F)cc1] | 2,6-Difluoro-3-iodo-N-[4-(5-methoxy-benzoimidazol-1-yl)-phenyl]-benzamide |

-continued

| Compound No. | Structure | Chemical Name |
|---|---|---|
| 160 | 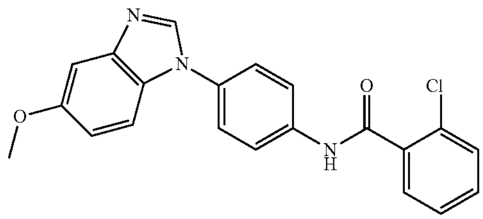 [SMILES: COc1ccc2c(c1)ncn2-c1ccc(NC(=O)c2ccccc2Cl)cc1] | 2-Chloro-N-[4-(5-methoxy-benzoimidazol-1-yl)-phenyl]-benzamide |
| 161 | 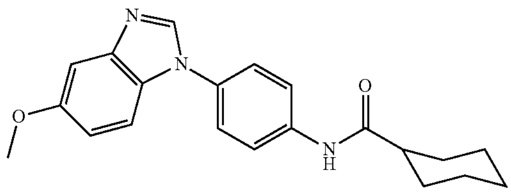 [SMILES: COc1ccc2c(c1)ncn2-c1ccc(NC(=O)C2CCCCC2)cc1] | N-[4-(5-methoxy-benzoimidazol-1-yl)-phenyl]-cyclohexanecarboxylic acid amide |
| 187 | 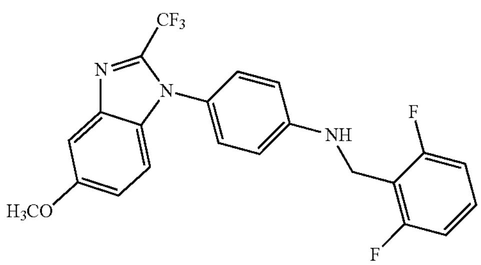 [SMILES: COc1ccc2c(c1)nc(C(F)(F)F)n2-c1ccc(NCc2c(F)cccc2F)cc1] | (2,6-Difluoro-benzyl)-[4-(5-methoxy-2-trifluoromethyl-benzoimidazol-1-yol)-phenyl]-amine |
| 188 | 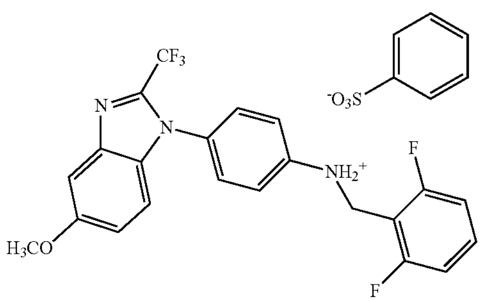 | (2,6-Difluoro-benzyl)-[4-(5-methoxy-2-trifluoromethyl-benzoimidazol-1-yol)-phenyl]-amine, benzenesulfonic acid salt |
| 189 | 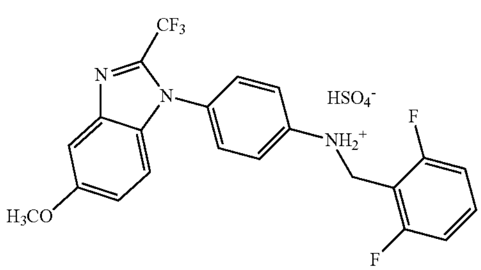 | (2,6-Difluoro-benzyl)-[4-(5-methoxy-2-trifluoromethyl-benzoimidazol-1-yol)-phenyl]-amine, sulfuric acid salt |

Mechanism of Action

Activation of 1-lymphocytes in response to an antigen is dependent on calcium ion oscillations. Calcium ion oscillations in T-lymphocytes are triggered through stimulation of the T-cell antigen receptor, and involve calcium ion influx through the stored-operated $Ca^{2+}$-release-activated $Ca^{2+}$ (CRAC) channel. Although the molecular structure of the CRAC ion channel has not been identified, a detailed electrophysiological profile of the channel exist. Thus, inhibition of CRAC ion channels can be measured by measuring inhibition of the $I_{CRAC}$ current. Calcium ion oscillations in T-cells have been implicated in the activation of several transcription factors (e.g., NEAT, Oct/Oap and NFκB) which are critical for T-cell activation (Lewis, *Biochemical Society Transactions* (2003), 31:925-929, the entire teachings of which are incorporated herein by reference). Certain compounds of any one of formulas (I) through (XVII), or compounds shown in Table 1, or a pharmaceutically acceptable salt, solvate, clathrate, or prodrug thereof, inhibit the activity of CRAC ion channels. Without wishing to be bound by any theory, it is believed that the compounds of the invention inhibit immune cell activation by inhibiting the activity of CRAC ion channels.

Compounds of any one of formulas (I) through (XVII), or compounds shown in Table 1, or a pharmaceutically acceptable salt, solvate, clathrate, or prodrug thereof, activate transient receptor potential melastatin 4 (TRPM4) ion channels. TRPM4 ion channels have been shown to modulate the membrane potential of the cell and, when activated, depolarize the cell membrane, thereby inhibiting calcium entry through other calcium permeable pathways (see Launay et al., *Cell* (2002), 109:397-407, the entire teachings of which are incorporated herein by reference). Therefore, it has been suggested that activation of the TRPM4 channels inhibits T-cell activation by inhibiting the activation of transcription factors that are dependent on calcium ion signalling.

Compounds of any one of formulas (I) through (XVII), or compounds shown in Table 1, or a pharmaceutically acceptable salt, solvate, clathrate, or prodrug thereof, inhibit the activity of Kv1.3 potassium ion channels. Kv1.3 is another ion channel which is involved in control of membrane potential and calcium influx. Blockade of Kv1.3 has been shown to prevent T-cell activation and attenuate immune responses in vivo (Koo et al., *Cellular Immunology* (1999), 197:99-107, the entire teachings of which are incorporated herein by reference).

Methods of Treatment and Prevention

In accordance with the invention, an effective amount of a compound of any one of formulas (I) through (XVII), or a compound shown in Table 1, or a pharmaceutically acceptable salt, solvate, clathrate, or prodrug thereof, or a pharmaceutical composition comprising a compound of any one of formulas (I) through (XVII), or a compound shown in Table 1, or a pharmaceutically acceptable salt, solvate, clathrate, or prodrug thereof, is administered to a patient in need of immunosuppression or in need of treatment or prevention of an inflammatory condition or immune disorder. Such patients may be treatment naïve or may experience partial or no response to conventional therapies.

Responsiveness of a particular inflammatory condition or immune disorder in a subject can be measured directly (e.g., measuring blood levels of inflammatory cytokines (such as IL-2, IL-4, IL-5, IL-13, GM-CSF, TNF-α, IFN-γ and the like) after administration of a compound or formulation of this invention), or can be inferred based on an understanding of disease etiology and progression. A compound of any one of formulas (I) through (XVII), or a compound shown in Table 1, or a pharmaceutically acceptable salt, solvate, clathrate, or prodrug thereof, can be assayed in vitro or in vivo, for the desired therapeutic or prophylactic activity, prior to use in humans. For example, known animal models of inflammatory conditions or immune disorders can be used to demonstrate the safety and efficacy of compounds of this invention.

Pharmaceutical Compositions and Dosage Forms

Pharmaceutical compositions and dosage forms of the invention comprise one or more active ingredients in relative amounts and formulated in such a way that a given pharmaceutical composition or dosage form can be used for immunosuppression or to treat or prevent inflammatory conditions and immune disorders. Preferred pharmaceutical compositions and dosage forms comprise a compound of any one of formulas (I) through (XVII), or a compound shown in Table 1, or a pharmaceutically acceptable salt, solvate, clathrate, or prodrug thereof, optionally in combination with one or more additional active agents.

Single unit dosage forms of the invention are suitable for oral, mucosal (e.g., nasal, sublingual, vaginal, buccal, or rectal), parenteral (e.g., subcutaneous, intravenous, bolus injection, intramuscular, or intraarterial), or transdermal administration, to a patient. Examples of dosage forms include, but are not limited to: tablets; caplets; capsules, such as soft elastic gelatin capsules; cachets; troches; lozenges; dispersions; suppositories; ointments; cataplasms (poultices); pastes; powders; dressings; creams; plasters; solutions; patches; aerosols (e.g., nasal sprays or inhalers); gels; liquid dosage forms suitable for oral or mucosal administration to a patient, including suspensions (e.g., aqueous or non-aqueous liquid suspensions, oil-in-water emulsions, or a water-in-oil liquid emulsions), solutions, and elixirs; liquid dosage forms suitable for parenteral administration to a patient; and sterile solids (e.g., crystalline or amorphous solids) that can be reconstituted to provide liquid dosage forms suitable for parenteral administration to a patient.

The composition, shape, and type of dosage forms of the invention will typically vary depending on their use. For example, a dosage form suitable for mucosal administration may contain a smaller amount of active ingredient(s) than an oral dosage form used to treat the same indication. This aspect of the invention will be readily apparent to those skilled in the art. See, e.g., Remington's Pharmaceutical Sciences (1990) 18th ed., Mack Publishing, Easton Pa.

Typical pharmaceutical compositions and dosage forms comprise one or more excipients. Suitable excipients are well known to those skilled in the art of pharmacy, and non-limiting examples of suitable excipients are provided herein. Whether a particular excipient is suitable for incorporation into a pharmaceutical composition or dosage form depends on a variety of factors well known in the art including, but not limited to, the way in which the dosage form will be administered to a patient. For example, oral dosage forms such as tablets may contain excipients not suited for use in parenteral dosage forms.

The suitability of a particular excipient may also depend on the specific active ingredients in the dosage form. For example, the decomposition of some active ingredients can be accelerated by some excipients such as lactose, or when exposed to water. Active ingredients that comprise primary or secondary amines are particularly susceptible to such accelerated decomposition. Consequently, this invention encompasses pharmaceutical compositions and dosage forms that contain little, if any, lactose. As used herein, the term "lactose-free" means that the amount of lactose present, if any, is insufficient to substantially increase the degradation rate of an active ingredient. Lactose-free compositions of the invention can comprise excipients that are well known in the art and are listed, for example, in the U.S. Pharmacopeia (USP) SP (XXI)/NF (XVI). In general, lactose-free compositions comprise active ingredients, a binder/filler, and a lubricant in pharmaceutically compatible and pharmaceutically acceptable amounts. Preferred lactose-free dosage forms comprise active ingredients, microcrystalline cellulose, pre-gelatinized starch, and magnesium stearate.

This invention further encompasses anhydrous pharmaceutical compositions and dosage forms comprising active ingredients, since water can facilitate the degradation of some compounds. For example, the addition of water (e.g., 5%) is widely accepted in the pharmaceutical arts as a means of simulating long-term storage in order to determine characteristics such as shelf-life or the stability of formulations over time. See, e.g., Jens T. Carstensen (1995) Drug Stability: Principles & Practice, 2d. Ed., Marcel Dekker, NY, N.Y., 379-80. In effect, water and heat accelerate the decomposition of some compounds. Thus, the effect of water on a formulation can be of great significance since moisture and/or humidity are commonly encountered during manufacture, handling, packaging, storage, shipment, and use of formulations.

Anhydrous pharmaceutical compositions and dosage forms of the invention can be prepared using anhydrous or low moisture containing ingredients and low moisture or low humidity conditions. Pharmaceutical compositions and dosage forms that comprise lactose and at least one active ingredient that comprises a primary or secondary amine are preferably anhydrous if substantial contact with moisture and/or humidity during manufacturing, packaging, and/or storage is expected.

An anhydrous pharmaceutical composition should be prepared and stored such that its anhydrous nature is maintained. Accordingly, anhydrous compositions are preferably packaged using materials known to prevent exposure to water such that they can be included in suitable formulary kits. Examples of suitable packaging include, but are not limited to, hermetically sealed foils, plastics, unit dose containers (e.g., vials), blister packs, and strip packs.

The invention further encompasses pharmaceutical compositions and dosage forms that comprise one or more compounds that reduce the rate by which an active ingredient will decompose. Such compounds, which are referred to herein as "stabilizer" include, but are not limited to, antioxidants such as ascorbic acid, pH buffers, or salt buffers.

Like the amounts and types of excipients, the amounts and specific types of active ingredients in a dosage form may differ depending on factors such as, but not limited to, the route by which it is to be administered to patients. However, typical dosage forms of the invention comprise a compound of any one of formulas (I) through (XVII), or a compound shown in Table 1, or a pharmaceutically acceptable salt, solvate, clathrate, or prodrug thereof, in an amount of from about 1 mg to about 1000 mg, preferably in an amount of from about 50 mg to about 500 mg, and most preferably in an amount of from about 75 mg to about 350 mg. The typical total daily dosage of a compound of any one of formulas (I) through (XVII), or a compound shown in Table 1, or a pharmaceutically acceptable salt, solvate, clathrate, or prodrug thereof, can range from about 1 mg to about 5000 mg per day, preferably in an amount from about 50 mg to about 1500 mg per day, more preferably from about 75 mg to about 1000 mg per day. It is within the skill of the art to determine the appropriate dose and dosage form for a given patient.

Oral Dosage Forms

Pharmaceutical compositions of the invention that are suitable for oral administration can be presented as discrete dosage forms, such as, but are not limited to, tablets (e.g., chewable tablets), caplets, capsules, and liquids (e.g., flavored syrups). Such dosage forms contain predetermined amounts of active ingredients, and may be prepared by methods of pharmacy well known to those skilled in the art. See generally, Remington's Pharmaceutical Sciences (1990) 18th ed., Mack Publishing, Easton Pa.

Typical oral dosage forms of the invention are prepared by combining the active ingredient(s) in an admixture with at least one excipient according to conventional pharmaceutical compounding techniques. Excipients can take a wide variety of forms depending on the form of preparation desired for administration. For example, excipients suitable for use in oral liquid or aerosol dosage forms include, but are not limited to, water, glycols, oils, alcohols, flavoring agents, preservatives, and coloring agents. Examples of excipients suitable for use in solid oral dosage forms (e.g., powders, tablets, capsules, and caplets) include, but are not limited to, starches, sugars, micro-crystalline cellulose, diluents, granulating agents, lubricants, binders, and disintegrating agents.

Because of their ease of administration, tablets and capsules represent the most advantageous oral dosage unit forms, in which case solid excipients are employed. If desired, tablets can be coated by standard aqueous or nonaqueous techniques. Such dosage forms can be prepared by any of the methods of pharmacy. In general, pharmaceutical compositions and dosage forms are prepared by uniformly and intimately admixing the active ingredients with liquid carriers, finely divided solid carriers, or both, and then shaping the product into the desired presentation if necessary.

For example, a tablet can be prepared by compression or molding. Compressed tablets can be prepared by compressing in a suitable machine the active ingredients in a free-flowing form such as powder or granules, optionally mixed with an excipient. Molded tablets can be made by molding in a suitable machine a mixture of the powdered compound moistened with an inert liquid diluent.

Examples of excipients that can be used in oral dosage forms of the invention include, but are not limited to, binders, fillers, disintegrants, and lubricants. Binders suitable for use in pharmaceutical compositions and dosage forms include, but are not limited to, corn starch, potato starch, or other starches, gelatin, natural and synthetic gums such as acacia, sodium alginate, alginic acid, other alginates, powdered tragacanth, guar gum, cellulose and its derivatives (e.g., ethyl cellulose, cellulose acetate, carboxymethyl cellulose calcium, sodium carboxymethyl cellulose), polyvinyl pyrrolidone, methyl cellulose, pre-gelatinized starch, hydroxypropyl methyl cellulose, (e.g., Nos. 2208, 2906, 2910), microcrystalline cellulose, and mixtures thereof.

Suitable forms of microcrystalline cellulose include, but are not limited to, the materials sold as AVICEL-PH-101, AVICEL-PH-103 AVICEL RC-581, AVICEL-PH-105 (available from FMC Corporation, American Viscose Division, Avicel Sales, Marcus Hook, Pa.), and mixtures thereof. One specific binder is a mixture of microcrystalline cellulose and sodium carboxymethyl cellulose sold as AVICEL RC-581. Suitable anhydrous or low moisture excipients or additives include AVICEL-PH-103J and Starch 1500 LM.

Examples of fillers suitable for use in the pharmaceutical compositions and dosage forms disclosed herein include, but are not limited to, talc, calcium carbonate (e.g., granules or powder), microcrystalline cellulose, powdered cellulose, dextrates, kaolin, mannitol, silicic acid, sorbitol, starch, pre-gelatinized starch, and mixtures thereof. The binder or filler in pharmaceutical compositions of the invention is typically present in from about 50 to about 99 weight percent of the pharmaceutical composition or dosage form.

Disintegrants are used in the compositions of the invention to provide tablets that disintegrate when exposed to an aqueous environment. Tablets that contain too much disintegrant may disintegrate in storage, while those that contain too little may not disintegrate at a desired rate or under the desired conditions. Thus, a sufficient amount of disintegrant that is neither too much nor too little to detrimentally alter the release of the active ingredients should be used to form solid oral dosage forms of the invention. The amount of disintegrant used varies based upon the type of formulation, and is readily discernible to those of ordinary skill in the art. Typical pharmaceutical compositions comprise from about 0.5 to about 15 weight percent of disintegrant, preferably from about 1 to about 5 weight percent of disintegrant.

Disintegrants that can be used in pharmaceutical compositions and dosage forms of the invention include, but are not limited to, agar-agar, alginic acid; calcium carbonate, microcrystalline cellulose, croscarmellose sodium, crospovidone, polacrilin potassium, sodium starch glycolate, potato or tapioca starch, other starches, pre-gelatinized starch, other starches, clays, other algins, other celluloses, gums, and mixtures thereof.

Lubricants that can be used in pharmaceutical compositions and dosage forms of the invention, include, but are not limited to, calcium stearate, magnesium stearate, mineral oil, light mineral oil, glycerin, sorbitol, mannitol, polyethylene glycol, other glycols, stearic acid, sodium lauryl sulfate, talc, hydrogenated vegetable oil (e.g., peanut oil, cottonseed oil, sunflower oil, sesame oil, olive oil, corn oil, and soybean oil), zinc stearate, ethyl oleate, ethyl laureate, agar, and mixtures thereof. Additional lubricants include, for example, a syloid silica gel (AEROSIL 200, manufactured by W.R. Grace Co. of Baltimore, Md.), a coagulated aerosol of synthetic silica (marketed by Degussa Co. of Plano, Tex.), CAB-O-SIL (a pyrogenic silicon dioxide product sold by Cabot Co. of Boston, Mass.), and mixtures thereof. If used at all, lubricants are typically used in an amount of less than about 1 weight percent of the pharmaceutical compositions or dosage forms into which they are incorporated.

Controlled Release Dosage Forms

Active ingredients of the invention can be administered by controlled release means or by delivery devices that are well known to those of ordinary skill in the art. Examples include, but are not limited to, those described in U.S. Pat. Nos. 3,845,770; 3,916,899; 3,536,809; 3,598,123; and 4,008,719, 5,674,533, 5,059,595, 5,591,767, 5,120,548, 5,073,543, 5,639,476, 5,354,556, and 5,733,566, each of which is incorporated herein by reference. Such dosage forms can be used to provide slow or controlled-release of one or more active ingredients using, for example, hydroxypropylmethyl cellulose, other polymer matrices, gels, permeable membranes, osmotic systems, multilayer coatings, microparticles, liposomes, microspheres, or a combination thereof to provide the desired release profile in varying proportions. Suitable controlled-release formulations known to those of ordinary skill in the art, including those described herein, can be readily selected for use with the active ingredients of the invention. The invention thus encompasses single unit dosage forms suitable for oral administration such as, but not limited to, tablets, capsules, gelcaps, and caplets that are adapted for controlled-release.

All controlled-release pharmaceutical products have a common goal of improving drug therapy over that achieved by their non-controlled counterparts. Ideally, the use of an optimally designed controlled-release preparation in medical treatment is characterized by a minimum of drug substance being employed to cure or control the condition in a minimum amount of time. Advantages of controlled-release, formulations include extended activity of the drug, reduced dosage frequency, and increased patient compliance. In addition, controlled-release formulations can be used to affect the time of onset of action or other characteristics, such as blood levels of the drug, and can thus affect the occurrence of side (e.g., adverse) effects.

Most controlled-release formulations are designed to initially release an amount of drug (active ingredient) that promptly produces the desired therapeutic effect, and gradually and continually release of other amounts of drug to maintain this level of therapeutic or prophylactic effect over an extended period of time. In order to maintain this constant level of drug in the body, the drug must be released from the dosage form at a rate that will replace the amount of drug being metabolized and excreted from the body. Controlled-release of an active ingredient can be stimulated by various conditions including, but not limited to, pH, temperature, enzymes, water, or other physiological conditions or compounds.

A particular extended release formulation of this invention comprises a therapeutically or prophylactically effective amount of a compound of formula (I), or a pharmaceutically acceptable salt, solvate, hydrate, clathrate, or prodrug thereof, in spheroids which further comprise microcrystalline cellulose and, optionally, hydroxypropylmethyl-cellulose coated with a mixture of ethyl cellulose and hydroxypropylmethyl-cellulose. Such extended release formulations can be prepared according to U.S. Pat. No. 6,274,171, the entirely of which is incorporated herein by reference.

A specific controlled-release formulation of this invention comprises from about 6% to about 40% a compound of any one of formulas (I) through (XVII), or a compound shown in Table 1, or a pharmaceutically acceptable salt, solvate, clathrate, or prodrug thereof, by weight, about 50% to about 94% microcrystalline cellulose, NF, by weight, and optionally from about 0.25% to about 1% by weight of hydroxypropyl-methylcellulose, USP, wherein the spheroids are coated with a film coating composition comprised of ethyl cellulose and hydroxypropylmethylcellulose.

Parenteral Dosage Forms

Parenteral dosage forms can be administered to patients by various routes including, but not limited to, subcutaneous, intravenous (including bolus injection), intramuscular, and intraarterial. Because their administration typically bypasses patients' natural defenses against contaminants, parenteral dosage forms are preferably sterile or capable of being sterilized prior to administration to a patient. Examples of parenteral dosage forms include, but are, not limited to, solutions ready for injection, dry products ready to be dissolved or suspended in a pharmaceutically acceptable vehicle for injection, suspensions ready for injection, and emulsions.

Suitable vehicles that can be used to provide parenteral dosage forms of the invention are well known to those skilled in the art. Examples include, but are not limited to: Water for Injection USP; aqueous vehicles such as, but not limited to, Sodium Chloride Injection, Ringers Injection, Dextrose Injection, Dextrose and Sodium Chloride Injection, and Lactated Ringer's Injection; water-miscible vehicles such as, but not limited to, ethyl alcohol, polyethylene glycol, and polypropylene glycol; and non-aqueous vehicles such as, but not limited to, corn oil, cottonseed, oil, peanut oil, sesame oil, ethyl oleate, isopropyl myristate, and benzyl benzoate.

Compounds that increase the solubility of one or more of the active ingredients disclosed herein can also be incorporated into the parenteral dosage forms of the invention.

Transdermal, Topical, and Mucosal Dosage Forms

Transdermal, topical, and mucosal dosage forms of the invention include, but are not limited to, ophthalmic solutions, sprays, aerosols, creams, lotions, ointments, gels, solutions, emulsions, suspensions, or other forms known to one of skill in the art. See, e.g., Remington's Pharmaceutical Sciences (1980 & 1990) 16th and 18th eds., Mack Publishing, Easton Pa. and Introduction to Pharmaceutical Dosage Forms (1985) 4th ed., Lea & Febiger, Philadelphia. Dosage forms suitable for treating mucosal tissues within the oral cavity can be formulated as mouthwashes or as oral gels. Further, transdermal dosage forms include "reservoir type" or "matrix type" patches, which can be applied to the skin and worn for a specific period of time to permit the penetration of a desired amount of active ingredients.

Suitable excipients (e.g., carriers and diluents) and other materials that can be used to provide transdermal, topical, and mucosal dosage forms encompassed by this invention are well known to those skilled in the pharmaceutical arts, and depend on the particular tissue to which a given pharmaceutical composition or dosage form will be applied. With that fact in mind, typical excipients include, but are not limited to, water, acetone, ethanol, ethylene glycol, propylene glycol, butane-1,3-diol, isopropyl myristate, isopropyl palmitate, mineral oil, and mixtures thereof to form lotions, tinctures, creams, emulsions, gels or ointments, which are non-toxic and pharmaceutically acceptable. Moisturizers or humectants can also be added to pharmaceutical compositions and dosage forms if desired. Examples of such additional ingredients are well known in the art. See, e.g., Remington's Pharmaceutical Sciences (1980 & 1990) 16th and 18th eds., Mack Publishing, Easton Pa.

Depending on the specific tissue to be treated, additional components may be used prior to, in conjunction with, or subsequent to treatment with active ingredients of the invention. For example, penetration enhancers can, be used to assist in delivering the active ingredients to the tissue. Suitable penetration enhancers include, but are not limited to: acetone; various alcohols such as ethanol, oleyl, and tetrahydrofuryl; alkyl sulfoxides such as dimethyl sulfoxide; dimethyl acetamide; dimethyl formamide; polyethylene glycol; pyrrolidones such as polyvinylpyrrolidone; Kollidon grades (Povidone, Polyvidone); urea; and various water-soluble or insoluble sugar esters such as Tween 80 (polysorbate 80) and Span 60 (sorbitan monostearate).

The pH of a pharmaceutical composition or dosage form, or of the tissue to which the pharmaceutical composition or dosage form is applied, may also be adjusted to improve delivery of one or more active ingredients. Similarly, the polarity of a solvent carrier, its ionic strength, or tonicity can be adjusted to improve delivery. Compounds such as stearates can also be added to pharmaceutical compositions or dosage forms to advantageously alter the hydrophilicity or lipophilicity of one or more active ingredients so as to improve delivery. In this regard, stearates can serve as a lipid vehicle for the formulation, as an emulsifying agent or surfactant, and as a delivery-enhancing or penetration-enhancing agent. Different salts, hydrates or solvates of the active ingredients can be used to further adjust the properties of the resulting composition.

Combination Therapy

The methods for immunosuppression or for treating or preventing inflammatory conditions and immune disorders in a patient in need thereof can further comprise administering to the patient being administered a compound of this invention, an effective amount of one or more other active agents. Such active agents may include those used conventionally for immunosuppression or for inflammatory conditions or immune disorders. These other active agents may also be those that provide other benefits when administered in combination with the compounds of this invention. For example, other therapeutic agents may include, without limitation, steroids, non-steroidal anti-inflammatory agents, antihistamines, analgesics, immunosuppressive agents and suitable mixtures thereof. In such combination therapy treatment, both the compounds of this invention and the other drug agent(s) are administered to a subject (e.g., humans, male or female) by conventional methods. The agents may be administered in a single dosage form or in separate dosage forms. Effective amounts of the other therapeutic agents and dosage forms are well known to those skilled in the art. It is well within the skilled artisan's purview to determine the other therapeutic agents optimal effective-amount range.

In one embodiment of the invention where another therapeutic agent is administered to a subject, the effective amount of the compound of this invention is less than its effective amount when the other therapeutic agent is not administered. In another embodiment, the effective amount of the conventional agent is less than its effective amount when the compound of this invention is not administered. In this way, undesired side effects associated with high doses of either agent may be minimized. Other potential advantages (including without limitation improved dosing regimens and/or reduced drug cost) will be apparent to those of skill in the art.

In one embodiment relating to autoimmune and inflammatory conditions, the other therapeutic agent may be a steroid or a non-steroidal anti-inflammatory agent. Particularly useful non-steroidal anti-inflammatory agents, include, but are not limited to, aspirin, ibuprofen, diclofenac, naproxen, benoxaprofen, flurbiprofen, fenoprofen, flubufen, ketoprofen, indoprofen, piroprofen, carprofen, oxaprozin, pramoprofen, muroprofen, trioxaprofen, suprofen, aminoprofen, tiaprofenic acid, fiuprofen, bucloxic acid, indomethacin, sulindac, tolmetin, zomepirac, tiopinac, zidometacin, acemetacin, fentiazac, clidanac, oxpinac, mefenamic acid, meclofenamic acid, flufenamic acid, niflumic acid, tolfenamic acid, diflurisal, flufenisal, piroxicam, sudoxicam, isoxicam; salicylic acid derivatives, including aspirin, sodium salicylate, choline magnesium trisalicylate, salsalate, diflunisal, salicylsalicylic acid, sulfasalazine, and olsalazin; para-aminophenol derivatives including acetaminophen and phenacetin; indole and indene acetic acids, including indomethacin, sulindac, and etodolac; heteroaryl acetic acids, including tolmetin, diclofenac, and ketorolac; anthranilic acids (fenamates), including mefenamic acid, and meclofenamic acid; enolic acids, including oxicams (piroxicam, tenoxicam), and pyrazolidinediones (phenylbutazone, oxyphenthartazone); and alkanones, including nabumetone and pharmaceutically acceptable salts thereof and mixtures thereof. For a more detailed description of the NSAIDs, see Paul A. Insel, *Analgesic-Antipyretic and Antiinflammatory Agents and Drugs Employed in the Treatment of Gout*, in Goodman & Gilman's The Pharmacological Basis of Therapeutics 617-57 (Perry B. Molinhoff and Raymond W. Ruddon eds., 9$^{th}$ ed 1996) and Glen R. Hanson, *Analgesic, Antipyretic and Anti-Inflammatory Drugs in Remington: The Science and Practice of Pharmacy Vol II* 1196-1221 (A. R. Gennaro ed. 19th ed. 1995) which are hereby incorporated by reference in their entireties.

Of particular relevance to allergic disorders, the other therapeutic agent may be an antihistamine. Useful antihistamines include, but are not limited to, loratidine, cetirizine, fexofenadine, desloratidine, diphenhydramine, chlorpheniramine, chlorcyclizine, pyrilamine, promethazine, terfenadine, doxepin, carbinoxamine, clemastine, tripelennamine, brompheniramine, hydroxyzine, cyclizine, meclizine, cyproheptadine, phenindamine, acrivastine, azelastine, levocabastine, and mixtures thereof. For a more detailed description of antihistamines, see Goodman & Gilman's The Pharmacological Basis of Therapeutics (2001) 651-57, 10$^{th}$ ed).

Immunosuppressive agents include glucocorticoids, corticosteroids (such as Prednisone or Solumedrol), T cell blockers (such as cyclosporin A and FK506), purine analogs (such as azathioprine (Imuran)), pyrimidine analogs (such as cytosine arabinoside), alkylating agents (such as nitrogen mustard, phenylalanine mustard, buslfan, and cyclophosphamide), folic acid antagonists (such as aminopterin and methotrexate), antibiotics (such as rapamycin, actinomycin D, mitomycin C, puramycin, and chloramphenicol), human IgG, antilymphocyte globulin (ALG), and antibodies (such as anti-CD3 (OKT3), anti-CD4 (OKT4), anti-CD5, anti-CD7, anti-IL-2 receptor, anti-alpha/beta TCR, anti-ICAM-1, anti-CD20 (Rituxan), anti-IL-12 and antibodies to immunotoxins).

The foregoing and other useful combination therapies will be understood and appreciated by those of skill in the art. Potential advantages of such combination therapies include, a different efficacy profile, the ability to use less of each of the individual active ingredients to minimize toxic side effects, synergistic improvements in efficacy, improved ease of administration or use and/or reduced overall expense of compound preparation or formulation.

Other Embodiments

The compounds of this invention may be used as research tools (for example, as a positive control for evaluating other potential TRPM4 activators, CRAC or Kv1.3 inhibitors, or IL-2, IL-4, IL-5, IL-13, GM-CSF, TNF-α, and/or INF-γ inhibitors). These and other uses and embodiments of the compounds and compositions of this invention will be apparent to those of ordinary skill in the art.

The invention is further defined by reference to the following examples describing in detail the preparation of compounds of the invention. It will be apparent to those skilled in the art that many modifications, both to materials and methods, may be practiced without departing from the purpose and interest of this invention. The following examples are set forth to assist in understanding the invention and should not be construed as specifically limiting the invention described and claimed herein. Such variations of the invention, including the substitution of all equivalents now known or later developed, which would be within the purview of those skilled in the art, and changes in formulation or minor changes in experimental design, are to be considered to fall within the scope of the invention incorporated herein.

EXAMPLES

Experimental Rationale

Without wishing to be bound by theory, it is believed that the compounds of this invention activate TRPM4, and/or inhibit Kv1.3 and CRAC ion channels thereby inhibiting production of IL-2 and other key cytokines involved with inflammatory and immune responses. The examples that follow demonstrate these properties.

Materials and General Methods

Reagents and solvents used below can be obtained from commercial sources such as Aldrich Chemical Co. (Milwaukee, Wis., USA). $^1$H-NMR and $^{13}$C-NMR spectra were recorded on a Varian 300 MHz NMR spectrometer. Significant peaks are tabulated in the order: δ (ppm): chemical shift, multiplicity (s, singlet; d, doublet; t, triplet; q, quartet; m, multiplet; br s, broad singlet), coupling constant(s) in Hertz (Hz) and number of protons.

Human leukemic T cells (Jurkat cells) and HEK 293 cells transfected with the FLAG-humanTRPM4/pcDNA4/TO construct were grown on glass coverslips with DMEM medium supplemented with 10% FBS, blasticidin (5 μg/mL) and zeocin (0.4 g/mL). TRPM4 expression was induced one day before use by adding 1 μg/mL tetracycline to the culture medium and patch clamp experiments were performed 16-24 hours post-induction (for additional details see Launay et al. (2000)).

Patch clamp experiments were performed in the tight-seal whole-cell configuration at 21-25° C. High resolution current recordings were acquired by a computer-based patch clamp amplifier system (EPC-9, HEKA, Lambrecht, Germany). Patch pipettes had resistances between 2-4 MΩ after filling with the standard intracellular solution. Immediately following establishment of the whole-cell configuration, voltage ramps of 50-200 ms duration spanning the voltage range of −100 to +100 mV were delivered at a rate of 0.5 Hz over a period of 300-400 seconds. All voltages were corrected from a liquid junction potential of 10 mV between external and internal solutions when using glutamate as the intracellular anion. Currents were filtered at 2.9 kHz and digitized at 10 μs intervals. Capacitive currents and series resistance were determined and corrected before each voltage ramp using the automatic capacitance compensation of the EPC-9. The low resolution temporal development of membrane currents was assessed by extracting the current amplitude at −80 mV or +80 mV from individual ramp current records.

Example 1

Synthesis of Representative Exemplary Compounds of this Invention

A. General Synthesis of Compounds in which X is a Benzoimidazolyl (Method 1)

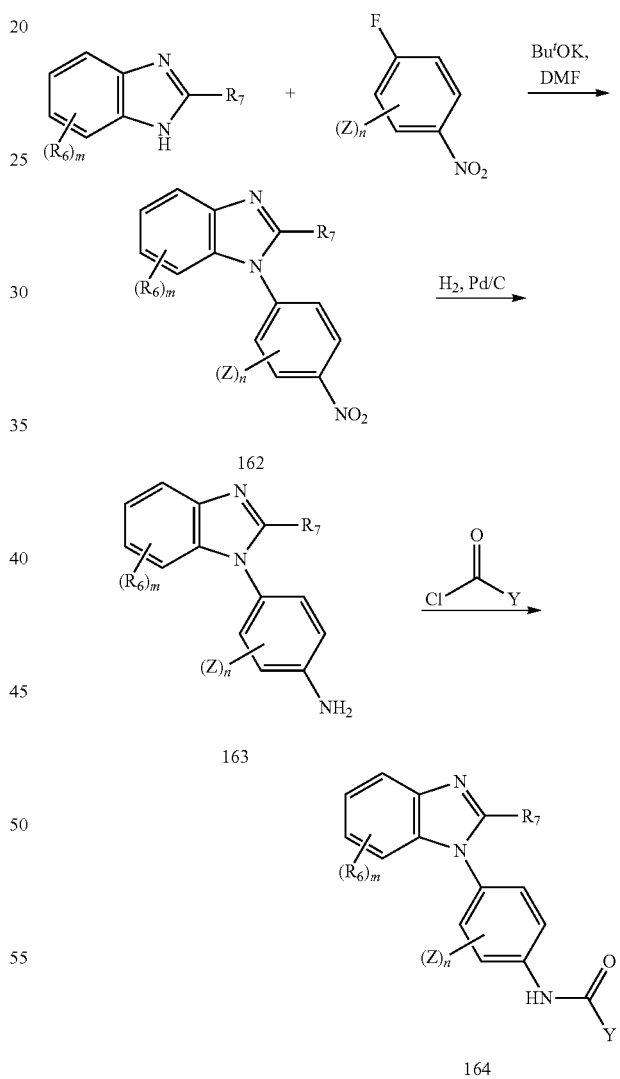

A suspension of a substituted benzoimidazole (27 mmol) and potassium t-butoxide (3.6 g, 30 mmol) in DMF (50 mL) was stirred at rt for 30 min. 1-Fluoro-4-nitro-benzene (4.2 g, 30 mmol) was added and the reaction mixture was heated to 150° C. for 4 h. The reaction mixture was diluted with water and extracted with ethyl acetate (EtOAc). The organic extract was washed with water and dried. The oil obtained, on concentration was flash chromatographed on silica gel to give 162 in 10-90% yields.

A stirred suspension of compound 162 (12 mmol) in EtOAc (100 mL) and 10% Pd—C (150 mg) was attached to a H$_2$ balloon for 4-12 h. The mixture was filtered through celite and concentrated to give compound 163.

To a mixture of compound 163 (4.0 mmol) and pyridine (1.3 mL) in chloroform (50 mL) at room temperature was added an acid chloride (5.0 mmol). The reaction mixture was stirred for 2-12 h. The reaction mixture was diluted with 1N HCl, extracted with chloroform and dried. The residue obtained on concentration was crystallized from EtOAc/hexane or flash chromatographed to give the product 164 in 30%-95% yields.

B. General Synthesis of Compounds in which X is a Benzoimidazolyl (Method 2)

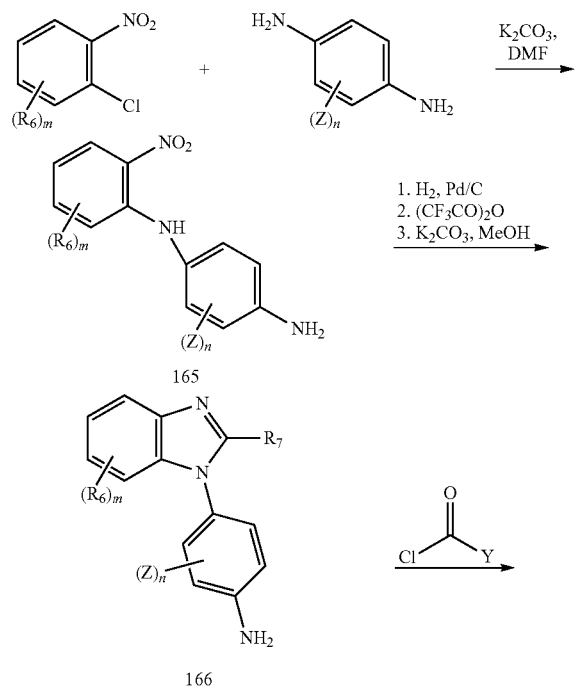

165

166

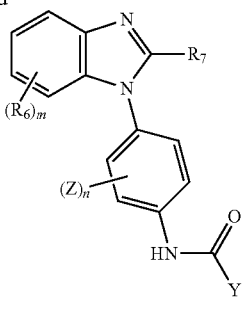

167

A suspension of (optionally substituted)-1-chloro-2-nitrobenzene (60 mmol), (optionally substituted)-benzene-1,4-diamine (33 g, 0.30 mol) and potassium carbonate (25 g, 0.30 mol) in DMF (200 mL) was heated at 120° C. for 4-120 hours. The reaction mixture was diluted with water and extracted with EtOAc. The organic extract was washed with water and dried. The oil obtained on concentration was flash chromatographed on silica gel to give compound 165 in 10-90% yields.

A stirred suspension of compound 165 (15 mmol) in EtOAc (100 mL) and 10% Pd—C (150 mg) was hydrogenated at room temperature for 4-12 h. The mixture was filtered through celite and concentrated (step 1). The oil obtained was mixed with trifluoroacetic acid (5 mL) and trifluoroacetic anhydride (5 mL) and heated at 80° C. for 30 min. The mixture was diluted with water, neutralized with sodium bicarbonate, and extracted with EtOAc. The organic extract was dried and concentrated (step 2). The oil obtained was diluted with methanol (100 mL), potassium carbonate (2.5 g, 30 mmol) was added, and the mixture was refluxed for 24 h. The reaction mixture was diluted with water and extracted with EtOAc. The organic extract was washed and dried (step 3). Removal of solvent gave compound 1.66 in 20-95% yields.

To a mixture of compound 166 (0.1.6 mmol) and pyridine (0.1 mL) in chloroform (5 mL) at room temperature was added an acyl chloride (0.25 mmol), and the reaction was stirred for 2 h. The reaction mixture was diluted with 1N HCl, extracted with chloroform and dried. The residue obtained on concentration was crystallized from EtOAc/hexane to give the product 167 in 30%-95% yields.

C. General Synthesis of Compounds in which X is a Benzoimidazolyl (Method 3)

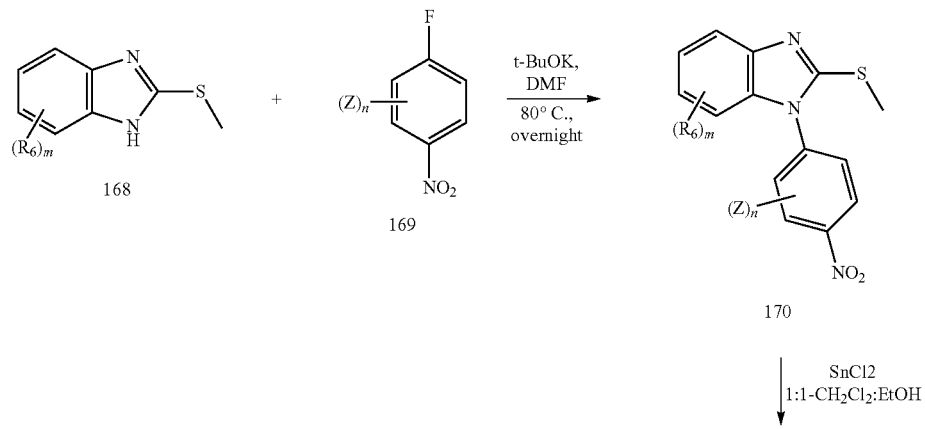

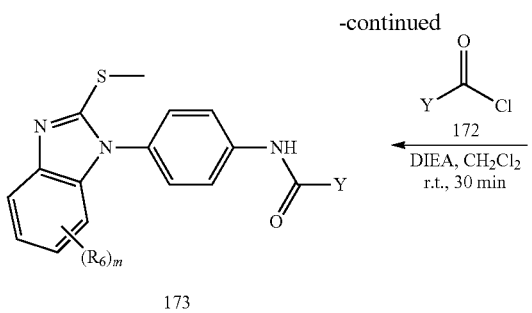
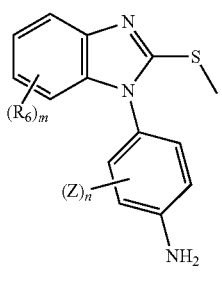

To a stirred solution of benzimidazole 168 (6.00 mmols) and p-fluoronitrobenzene 169 (6.00 mmols) in 10 mL of anhydrous DMF, was added [potassium t-butoxide (t-BuOK) (7.61 mmols, 1.25 eq.), and the reaction mixture was stirred at 80° C. overnight. The reaction mixture was added into 50 mL of water and the product was extracted with ethyl acetate (3×20 mL). The extracts were washed with brine and concentrated. Column chromatography on silica gel using mixture of hexane:ethyl acetate provided compound 170 in 25-45% yields.

To a stirred solution of compound 170 (1.31 mmols) in 20 mL of 1:1 $CH_2Cl_2$:EtOH, was added $SnCl_2$ (13.06 mmols) followed by a few drops of water. The mixture was stirred overnight and concentrated. 20 mL of water was added to the residue, and the solution the brought to pH~8-9 using 2N NaOH. The resulting mixture was extracted with ethyl acetate (20 mL×4), washed with brine (20 mL), dried over $Na_2SO_4$, and concentrated to afforded compound 171 in 70-97% yields.

To a solution of compound 171 (0.30 mmols) in 5 mL of $CH_2Cl_2$, was added an acyl chloride 172 (0.30 mmols), followed by diisopropyl-ethylamine (0.60 mmols). The resultant mixture was stirred at room temperature for 30 min and eluted through a short pad of silica gel using mixture of hexane:ethyl acetate to afford, upon concentration, the product 173 in 80-96% yields.

D. Synthesis of Compounds 34 and 50

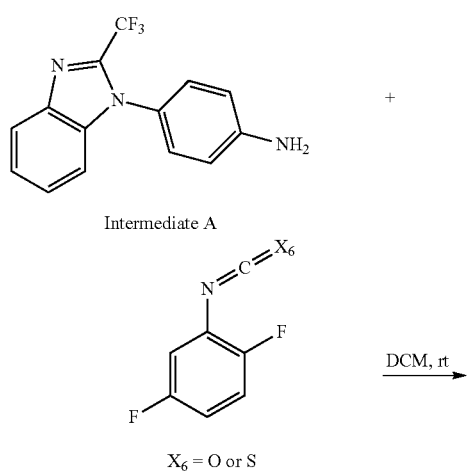

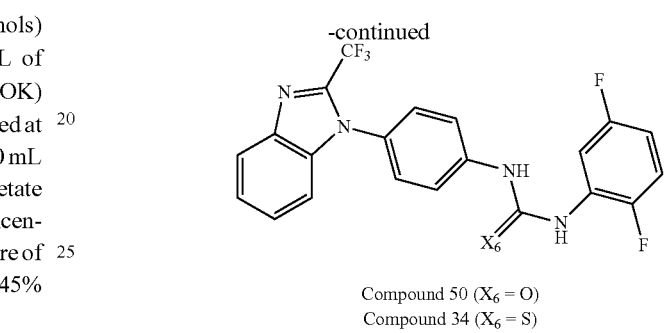

Compound 50 ($X_6$ = O)
Compound 34 ($X_6$ = S)

A solution of the intermediate A (see Method 1, Compound 163) (2 mmol) and 1,4-Difluoro-2-isocyanato-benzene (2 mmol) or 1,4-Difluoro-2-isothiocyanato-benzene (2 mmol) in DCM (2 mL) was stirred at room temperature for 48 hours. After removal of the solvent and volatile components, the crude material was separated by silica gel chromatography (hexane to 10% hexane/EtOAc to 50% hexane/EtOAc) to afford Compound 34 or Compound 5.

E. Synthesis of Compound 12

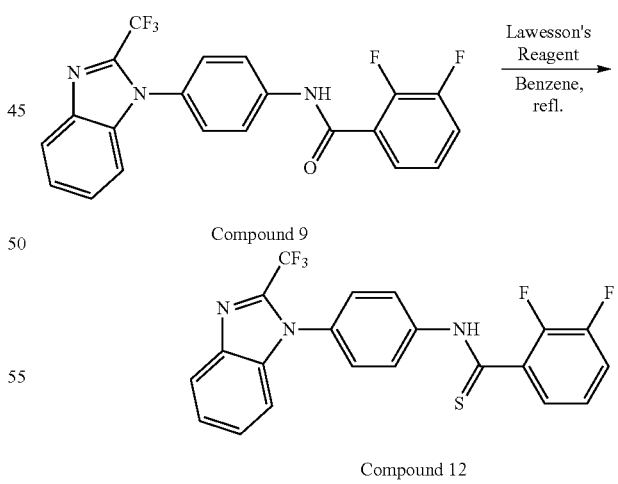

To a solution of Compound 9 (100 mg, 0.24 mmol) in dry benzene (10 mL) was added Lawesson's reagent (80 mg, 0.2 mmol) and the mixture was heated to reflux for 2 h. Undissolvable materials were then filtered off through celite, and the filtrate was concentrated followed by silica gel chromatography (hexane to 20% hexane/EtOAc) to afford Compound 12 as a yellow solid.

F. Synthesis of Compound 52

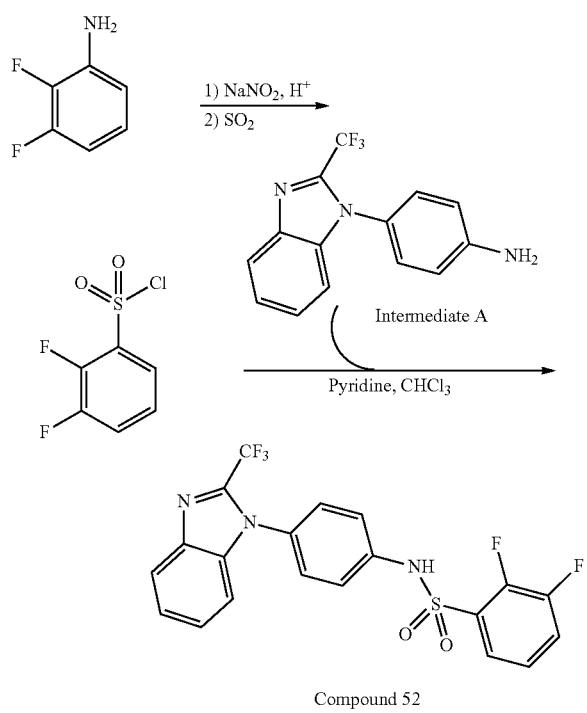

To a stirred solution of 2,3-difluoroanilline (2.58 g, 20 mmol) in water (25 mL) and concentrated hydrochloric acid (15 mL) at −10° C. was added a solution of NaNO₂ (1.45 g, 21 mmol) in water (3 mL) dropwise over a period of 30 min. After 10 min, this mixture was added to a SO₂ saturated solution in acetic acid (20 mL) and concentrated hydrochloric acid (2 mL) containing CuCl (0.6 g) at 0° C. The mixture was partitioned between water and EtOAc. Organic layer was separated and washed with NaHCO₃; dried (Na₂SO₄). The crude product 2,3-Difluoro-benzenesulfonyl chloride thus obtained was used directly without further purification.

The above obtained 2,3-Difluoro-benzenesulfonyl chloride (1.2 equiv.) was added to a solution of the "intermediate A" in chloroform and pyridine and the mixture was allowed to react at room temperature for 3 h. The mixture was diluted with dichloromethane (DCM) and washed with dilute hydrochloric acid and dried (Na₂SO₄). Pure product of Compound 52 was obtained by silica gel chromatography (30% hexane/EtOAc) as a white solid.

G. Synthesis of Compounds 46 and 47

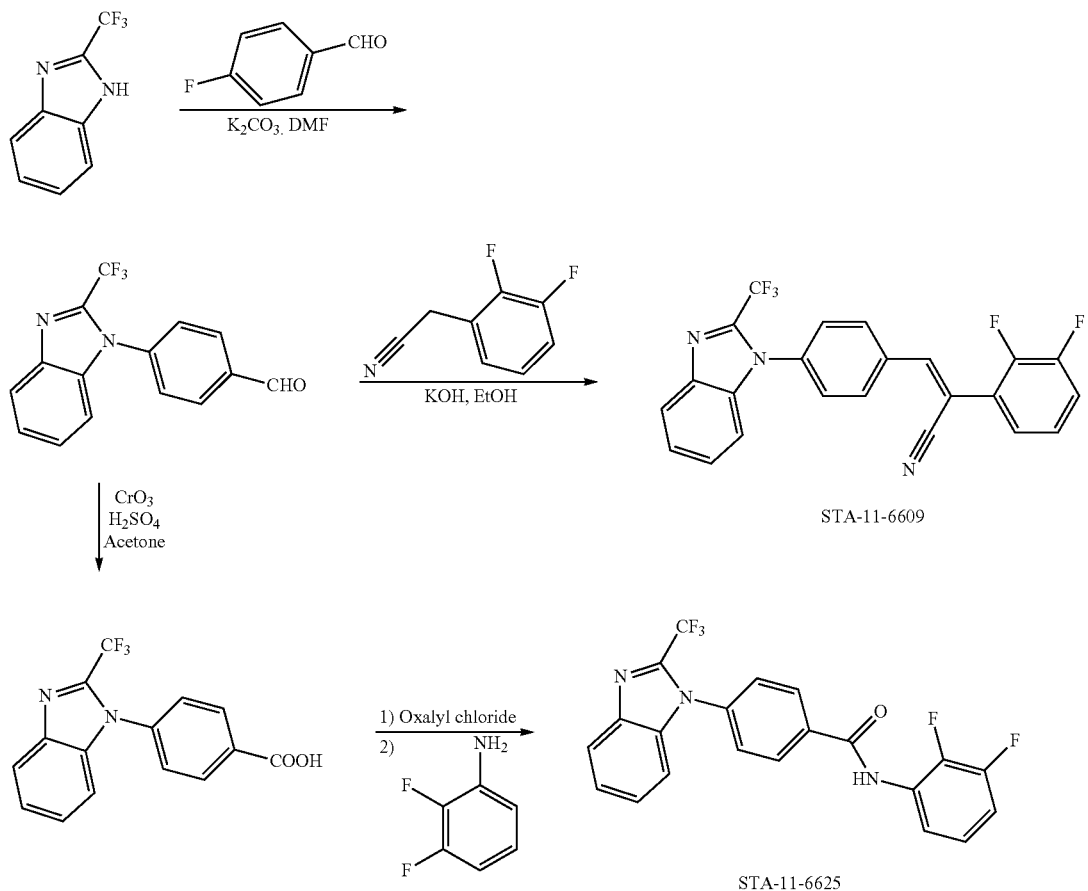

A stirred mixture of 2-Trifluoromethyl-1H-benzoimidazole (4.92 g, 26.4 mmol), 4-fluorobenaldehyde (3.1 mL, 29.1 mmol), and $K_2CO_3$ (4.37 g, 31.7 mmol) in DMF (50 mL) was heated to 150° C. for 16 h. After being cooled to room temperature, the reaction mixture was partitioned between $H_2O$ and EtOAC. After usual workup, the crude product was purified by silica gel chromatography (20% Hexane/EtOAc to 30% Hexane/EtOAc) to afford a yellow oil which was subjected to a second silica gel chromatography (DMC) to provide the aldehyde intermediate 4-(2-Trifluoromethyl-benzoimidazol-1-yl)-benzaldehyde as a white solid (4.0 g).

To a solution of the above 4-(2-Trifluoromethyl-benzoimidazol-1-yl)-benzaldehyde (0.155 g, 0.53 mmol) and (2,3-Difluoro-phenyl)-acetonitrile (83 mg, 0.54 mmol) in EtOH (5 mL) was added a solution of KOH (0.2 g) in H2O (0.5 mL). The mixture was then stirred at rt for 1 h, partitioned between EtOAc/$H_2O$. The organic layer was dried and concentrated followed by silica gel chromatography (20% Hexane/EtOAc) to afford the product Compound 47 as a colorless oil.

To a stirred solution of 4-(2-Trifluoromethyl-benzoimidazol-1-yl)-benzaldehyde (0.58 g, 2 mmol) in acetone (25 mL) was added Jones's reagent (1.0 mL, 2.0 M) at 0° C. After stirring at room temperature for 2 h, the mixture was partitioned between EtOAc and saturated $NaHCO_3$ solution. After usual workup, the crude material was separated by silica gel chromatography (50% Hexane/EtOAc to EtOAc) to afford the intermediate acid 4-(2-Trifluoromethyl-benzoimidazol-1-yl)-benzoic acid as awhile solid (490 mg).

To a stirred solution of 4-(2-Trifluoromethyl-benzoimidazol-1-yl)-benzoic acid (102 mg, 0.33 mmol) in dry $CHCl_3$ (15 mL) was added oxalyl chloride (0.09 mL) followed by one drop of DMF at room temperature. After 1 h, the reaction pot was concentrated and Vacuum dried. Dry chloroform (15 mL) and pyridine (0.1 mL) was then added followed by the addition of 2,3-difluoroanilline (36 mg, 0.28 mmol). The reaction was monitored by TLC, after completion, the mixture was partitioned between 1N HCl and DCM. Organic layer was separated and dried ($Na_2SO_4$). Removal of solvents followed silica gel chromatography (20% hexane/EtOAc) afforded the product Compound 46 as a white solid.

Methods 1-3, shown above, were utilized with appropriate starting materials and reagents to produce the following compounds of the invention. Choice of the appropriate starting materials and reagents will be readily apparent to one of skill in the art for these and other compounds of this invention.

Compound 3
$^1$H-NMR ($CDCl_3$) δ (ppm) 8.5 (br, 1H), 7.9 (m, 3H), 7.5 (d, 2H, J=8), 7.34 (s, 1H), 7.2 (m, 1H), 7.0 (m, 2H), 3.88 (s, 3H); ESMS clcd for $C_{22}H_{13}F_6N_3O_2$: 465.1; Found: 466.1 (M+H)$^+$.

Compound 6
$^1$H NMR δ (DMSO-$d_6$) 11.06 (s, 1H), 8.81 (d, J=0.9 Hz, 1H), 8.64 (dd, $J_1$=0.9 Hz, $J_2$=4.8 Hz, 1H), 7.96 (d, J=9 Hz, 2H), 7.76 (t, J=5.7 Hz, 1H), 7.62 (d, J=9 Hz, 2H), 7.43 (d, J=2.4 Hz, 1H), 7.07-7.15 (m, 2H), 3.84 (s, 3H); ESMS Calcd ($C_{21}H_{14}F_4N_4O_2$): 430.11, found (M+1) 431.11

Compound 9
$^1$H-NMR (CDCl3) δ (ppm), 8.50 (d, J=13.8 Hz, 1H), 7.97-7.90 (m, 4H), 7.48-7.39 (m, 5H), 7.34-7.31 (m, 1H), 7.21-7.18 (m, 1H); ESMS clcd for $C_{21}H_{12}F_5N_3O$: 417.10; Found: 418.1 (M+H)$^+$.

Compound 11
$^1$H NMR (300 MHz, $CDCl_3$), δ (ppm): 8.5 (d, J=15 Hz, 1H), 7.91-7.86 (m, 3H), 7.73 (d, J=7.8 Hz, 1H), 7.49-7.44 (m, 2H), 7.42-7.35 (m, 1H), 7.32-7.10 (m, 4H), 2.76 (s, 3H).

Compound 21
$^1$H-NMR (DMSO-$d_6$) δ (ppm) 10.9 (br, 1H), 8.0 (d, 2H, J=9), 7.7 (m, 1H), 7.6 (m, 3H), 7.4 (m, 1H), 7.1 (m, 1H), 6.5 (d, 1H, J=9), 6.3 (d, 1H, J=9), 5.8 (br, 2H); ESMS clcd for $C_{21}H_{13}F_6N_4O$: 432.1; Found: 433.0 (M+H)$^+$.

Compound 22
$^1$H-NMR ($CDCl_3$) δ (ppm) 9.0 (br, 1H), 8.1 (m, 1H), 7.9 (m, 3H), 7.4 (m, 4H), 7.2 (m, 1H), 6.7 (br, 1H), 1.56 (s, 9H); ESMS clcd for $C_{26}H_{20}F_6N_4O_3$: 550.1; Found: 551.1 (M+H)$^+$.

Compound 27
$^1$H-NMR (DMSO-$d_6$) δ (ppm) 11.1 (br, 1H), 8.7 (s, 1H), 8.4 (m, 1H), 8.0 (d, 2H, J=9), 7.8 (d, 2H, J=9), 7.7 (m, 2H), 7.5 (m, 2H), 7.3 (m, 1H); ESMS clcd for $C_{20}H_{12}F_4N_4O$: 400.1; Found: 401.1 (M+H)$^+$.

Compound 34
$^1$H-NMR ($CD_3OD$) δ 8.9 (d, 1H), 8.3 (s, 1H), 7.85-7.95 (m, 2H), 7.71 (d, 2H, J=8), 7.45 (d, 2H, J=8), 7.36-7.45 (m, 2H), 7.15-7.25 (m, 1H), 7.04-7.15 (m, 1H), 6.85-6.95 (m, 1H) ppm; ESMS clcd for $C_{20}H_{12}F_6N_6S$: 449.1; Found: 450.1 (M+H)$^+$.

Compound 45
$^1$H-NMR (CDCl3) δ (ppm), 9.14 (d, J=2.4 Hz 1H), 8.82 (m, 1H), 8.28-8.25 (m, 2H), 7.95-7.91 (m, 3H), 7.51-7.41 (m, 5H), 7.20-7.17 (m, 1H); ESMS clcd for $C_{20}H_{13}F_3N_4O$: 382.10; Found: 383.1 (M+H)$^+$.

Compound 47
$^1$H-NMR ($CDCl_3$) δ (ppm) 8.1 (m, 2H), 8.0 (m, 1H), 7.72 (s, 1H), 7.6 (d, 2H, J=8), 7.4 (m, 3H), 7.2 (m, 3H); ESMS clcd for $C_{13}H_{12}F_6N_3$: 425.1; Found: 426.1 (M+H)$^+$.

Compound 69
$^1$H-NMR ($CD_3OD$) δ 8.6 (s, 1H), 8.15 (m, 1H), 7.86 (d, 1H, J=9), 7.42-7.60 (m, 4H), 7.18-7.34 (m, 2H), 6.82 (d, 1H, J=1.5), 5.55-6.64 (m, 1H), 1.40 (s, 9H) ppm; ESMS clod for $C_{26}H_{21}F_3N_4O_3$: 494.2; Found: 495.2 (M+H)$^+$.

Compound 74
$^1$H-NMR ($CDCl_3$) δ (ppm) 8.44 (s, 1H), 8.20 (br, 1H), 8.0 (m, 6H), 7.6 (m, 2H), 7.5 (d, 2H, J=8), 7.4 (d, 1H, J=2), 7.1 (m, 2H), 3.89 (s, 3H); ESMS clcd for $C_{26}H_{18}F_3N_3O_2$: 461.1; Found: 462.1 (M+H)$^+$.

Compound 75
$^1$H-NMR (DMSO-$d_6$) δ (ppm) 10.3 (br, 1H), 8.1 (d, 2H, J=8), 7.6 (m, 1H), 7.55 (s, 1H), 7.4 (d, 2H, J=8), 7.33 (s, 1H), 7.0 (m, 3H), 6.12 (s, 2H), 3.86 (s, 3H); ESMS clcd for $C_{23}H_{16}F_3N_3O_4$: 455.1; Found: 456.1 (M+H)$^+$.

Compound 77
$^1$H-NMR ($CDCl_3$) δ (ppm) 8.0 (m, 3H), 7.8 (m, 4H), 7.5 (d, 2H, J=8), 7.4 (m, 1H), 7.0 (m, 2H), 3.89 (s, 3H); ESMS clcd for $C_{23}H_{16}F_3N_4O_2$: 436.1; Found: 437.1 (M+H)$^+$.

Compound 79
$^1$H-NMR (DMSO-$d_6$) δ (ppm) 10.5 (br, 1H), 8.0 (d, 2H, J=9), 7.9 (d, 2H, J=8), 7.6 (d, 2H, J=9), 7.4 (m, 3H), 7.1 (m, 2H), 3.84 (s, 3H), 2.7 (q, 2H, J=8), 1.2 (t, 3H, J=8); ESMS clcd for $C_{24}H_{20}F_3N_3O_2$: 439.1; Found: 440.1 (M+H)$^+$.

Compound 81
$^1$H-NMR (DMSO-$d_6$) δ (ppm) 11.2 (br, 1H), 9.2 (t, 2H, J=2), 9.0 (d, 1H, J=2), 8.1 (d, 2H, J=8), 7.6 (d, 2H, J=8), 7.43 (s, 1H), 7.1 (m, 2H), 3.84 (s, 3H); ESMS clcd for $C_{22}H_{14}F_3N_5O_6$: 501.1; Found: 502.1 (M+H)$^+$.

Compound 82
$^1$H-NMR (DMSO-$d_6$) δ (ppm) 10.2 (br, 1H), 7.8 (d, 2H, J=9), 7.5 (d, 2H, J=9), 7.4 (d, 1H, J=1), 7.1 (m, 2H), 3.83 (s, 3H), 2.3 (t, 2H, J=7), 1.6 (m, 2H), 0.9 (t, 3H, J=7); ESMS clcd for $C_{19}H_{18}F_3N_3O_2$: 377.1; Found: 378.1 (M+H)$^+$.

Compound 83
$^1$H-NMR (DMSO-$d_6$) δ (ppm) 10.9 (br, 1H), 8.2 (m, 1H), 8.1 (m, 4H), 7.8 (d, 1H, J=8), 7.6 (m, 5H), 7.4 (m, 1H), 7.1 (m, 2H), 3.85 (s, 3H); ESMS clod for $C_{26}H_{18}F_3N_3O_2$: 461.1; Found: 462.1 (M+H)$^+$.

Compound 91

$^1$H-NMR (CDCl$_3$) δ (ppm) 7.8 (m, 3H), 7.5 (d, 2H, J=8), 7.4 (m, 1H), TO (m, 2H), 3.89 (s, 3H); ESMS clcd for C$_{22}$H$_{11}$F$_8$N$_3$O$_2$: 501.1; Found: 502.0 (M+H)$^+$.

Compound 99

$^1$H-NMR (CD$_3$OD) δ7.99 (d, J=8.7 Hz, 2H), 7.50 (m, 4H), 7.65 (m, 1H), 7.18 (d, J=2.1 Hz, 1H), 7.03 (m, 2H), 6.89 (t, J=6.9 Hz, 1H)

ESMS clcd for C$_{21}$H$_{12}$F$_5$N$_3$O$_2$: 433.1; Found: 434.1 (M+H)$^+$.

Compound 101

$^1$H-NMR (DMSO-d$_6$) δ (ppm) 10.8 (br, 1H), 8.44 (s, 1H), 8.3 (d, 1H, J=6), 8.1 (d, 1H, J=8), 8.0 (d, 2H, J=9), 7.8 (t, 1H, J=8), 7.6 (d, 2H, J=9), 7.4 (d, 1H, J=2), 7.1 (m, 2H), 3.84 (s, 3H); ESMS clcd for C$_{23}$H$_{15}$F$_3$N$_4$O$_2$: 436.1; Found: 437.1 (M+H)$^+$.

Compound 105

$^1$H-NMR (DMSO-d$_6$) δ (ppm) 10.2 (br, 1H), 7.9 (d, 2H, J=9), 7.5 (d, 2H, J=9), 7.41 (s, 1H), 7.1 (m, 2H), 3.83 (s, 3H), 2.8 (m, 1H), 1.7 (m, 8H); ESMS clcd for C$_{21}$H$_{20}$F$_3$N$_3$O$_2$: 403.1; Found: 404.1 (M+H)$^+$.

Compound 106

$^1$H-NMR (DMSO-d$_6$) δ (ppm) 10.2 (br, 1H), 7.8 (d, 2H, J=8), 7.5 (d, 2H, J=8), 7.4 (m, 1H), 7.1 (m, 2H), 3.83 (s, 3H), 2.4 (m, 1H), 1.8 (m, 4H), 1.3 (m, 6H); ESMS clcd for C$_{22}$H$_{22}$F$_3$N$_3$O$_2$: 417.2; Found: 418.2 (M+H)$^+$.

Compound 111

$^1$H-NMR (DMSO-d$_5$) δ (ppm) 10.6 (br, 1H), 8.0 (m, 4H), 7.6 (m, 5H), 7.4 (d, 1H, J=2), 7.1 (m, 2H), 3.84 (s, 3H); ESMS clcd for C$_n$H$_{16}$F$_3$N$_3$O$_2$: 411.1; Found: 412.1 (M+H)$^+$.

Compound 112

$^1$H-NMR (CD$_3$OD) δ 8.5 (d, J=14.1 Hz, 1H), 7.94 (m, 3H), 7.40 (m, 5H), 7.08 (m, 2H), 4.59 (m, 1H), 1.38 (d, J=6.3 Hz, 6H);

ESMS clcd for C$_{24}$H$_{15}$F$_5$N$_3$O$_2$: 475.1; Found: 476.1 (M+H)$^+$.

Compound 114

$^1$H-NMR (DMSO-d$_6$) δ (ppm) 10.9 (br, 1H), 8.8 (m, 2H), 8.0 (m, 4H), 7.6 (m, 2H), 7.4 (m, 1H), 7.1 (m, 2H), 3.84 (s, 3H); ESMS clcd for C$_{21}$H$_{15}$F$_3$N$_4$O$_2$: 412.1; Found: 413.1 (M+H)$^+$.

Compound 116

$^1$H-NMR (DMSO-d$_6$) δ (ppm) 10.3 (br, 1H), 7.8 (d, 2H, J=9), 7.5 (d, 2H, J=9), 7.4 (m, 1H), U (m, 2H), 3.83 (s, 3H), 2.2 (d, 2H, J=7), 2.1 (m, 1H), 0.9 (d, 6H, J=7); ESMS clcd for C$_{20}$H$_{20}$F$_3$N$_3$O$_2$: 391.2; Found: 392.1 (M+H)$^+$.

Isomeric Mixture 136

$^1$H NMR δ (DMSO-d$_6$) 8.06 (d, J=2.1 Hz, 1H), 7.95-7.98 (m, 2H), 7.48-715 (m, 17H), 7.30-7.37 (m, 4H), 7.09 (d, J=9.3 Hz, 1H), 7.01 (d, J=2.1 Hz, 1H); ESMS Calcd (C$_{28}$H$_{13}$ClF$_7$N$_3$O$_2$): 591.06, found (M+1) 592.1

H. Typical Synthesis of Compounds in which X is a Imidazo[1,2-a]pyridyl (Compound 70)

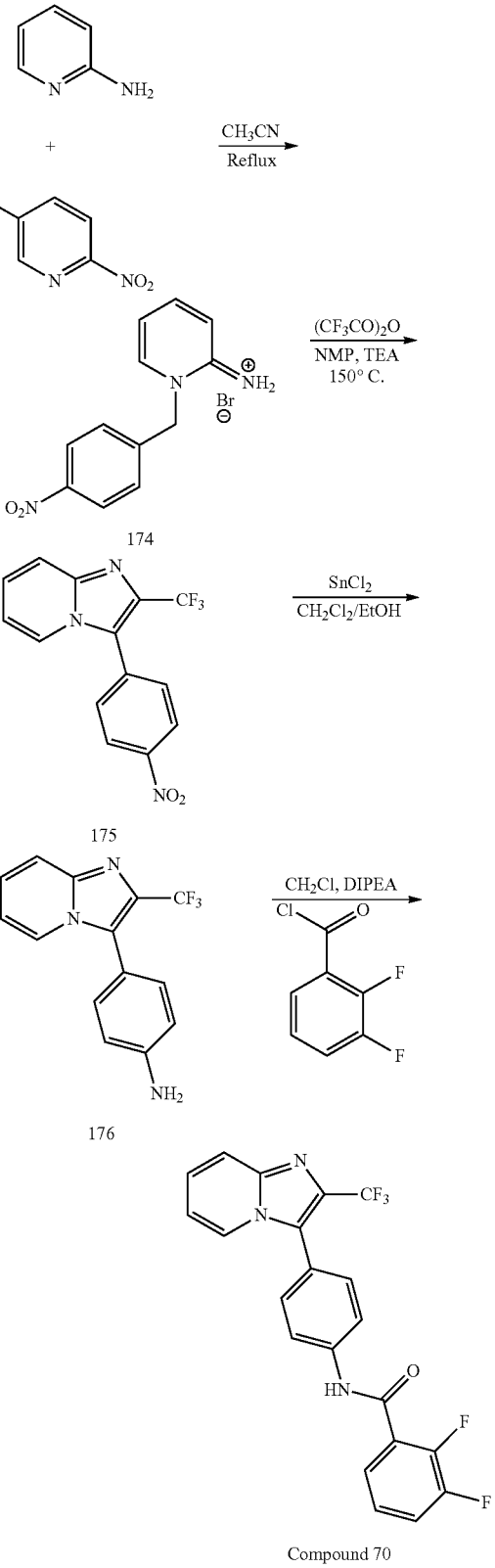

1.04 g (11 mmol) of 2-aminopyridine and 2.39 g (11 mmol) of p-nitrobenzylbromide were dissolved in 20 mL CH$_3$CN.

The solution was warmed to reflux for 1 hr then cooled to room temperature, diluted with Et$_2$O, and the solid filtered, washed 4× with Et$_2$O and collected to yield 3 g (88%) of 1-(4-Nitro-benzyl)-1H-pyridin-2-ylidene-ammonium bromide (174) as an off white solid.

To a solution of 1.01 g (3.27 mmol) of 1-(4-Nitro-benzyl)-1H-pyridin-2-ylidene-ammonium bromide (174) and 4 mL 1-methyl-2-pyrrolidinone (NMP) in a sealed tube was added 0.51 mL (3.6 mmol) of trifluoroacetic anhydride and 0.96 mL (6.9 mmol) of triethyl amine (TEA). The reaction mixture was heated to 155° C. for 3 hr then cooled to room temperature, diluted with 50 mL 2N NaOH and extracted 3 times with 30 mL EtOAc. The combined organics were washed with saturated aqueous NaHCO$_3$, and brine, dried over MgSO$_4$ filtered and concentrated in vacuo. The crude oil was purified by silica gel chromatography 1:2 (EtOAc:Hexanes) to yield 753 mg (74%) of 3-(4-Nitro-phenyl)-2-trifluoromethyl-imidazo[1,2-a]pyridine (175) as a yellow solid.

To a solution of 690 mg (2.3 mmol) of 3-(4-Nitro-phenyl)-2-trifluoromethyl-imidazo[1,2-a]pyridine (175) in 30 mL of a 1:1 mixture of CH$_2$Cl$_2$ and ethanol (EtOH) was added 4.3 g (23 mmol) of SnCl$_2$ and 4 drops of H$_2$O. The reaction was allowed to stir overnight at which time it was concentrated in vacuo, and the resulting oil dissolved in 40 mL of EtOAc and washed 3 times with 50 mL of 2N NaOH. The organic layer was then dried over MgSO$_4$ filtered and concentrated in vacuo. 73 mg (0.26 mmol) of the resulting solid was dissolved in 4 mL of CH$_2$Cl$_2$ to which 0.035 mL (0.27 mmol) of 3,4 difluorobenzoylchloride and 0.09 mL (0.52 mmol) diisopropyl ethyl amine (DIPEA) were added. The reaction was allowed to stir for 4 hrs at which time it was diluted with 20 mL CH$_2$Cl$_2$, quenched with 15 mL saturated aqueous NaHCO$_3$ and washed with 15 mL brine. The organic layer was then dried over MgSO$_4$ filtered and concentrated in vacuo. The crude oil was purified by silica gel chromatography 1:3 (EtOAc:Hexanes) to yield 91 mg (84%) of 2,3-Difluoro-N-[4-(2-trifluoromethyl-imidazo[1,2-a]pyridin-3-yl)-phenyl]-benzamide (Compound 70) as a white solid.

$^1$H-NMR (CDCl$_3$) δ 8.53 (d, J=10.8 Hz, 1H), 7.93 (m, 4H), 7.71 (d, J=9 Hz, 1H), 7.52 (d, J=8.4 Hz, 2H), 7.42 (m, 3H), 6.89 (t, J=6.9 Hz, 1H)

ESMS clcd for C$_{21}$H$_{12}$F$_5$N$_3$O: 417.1; Found: 418.3 (M+H)$^+$.

I. Synthesis of Compound 8

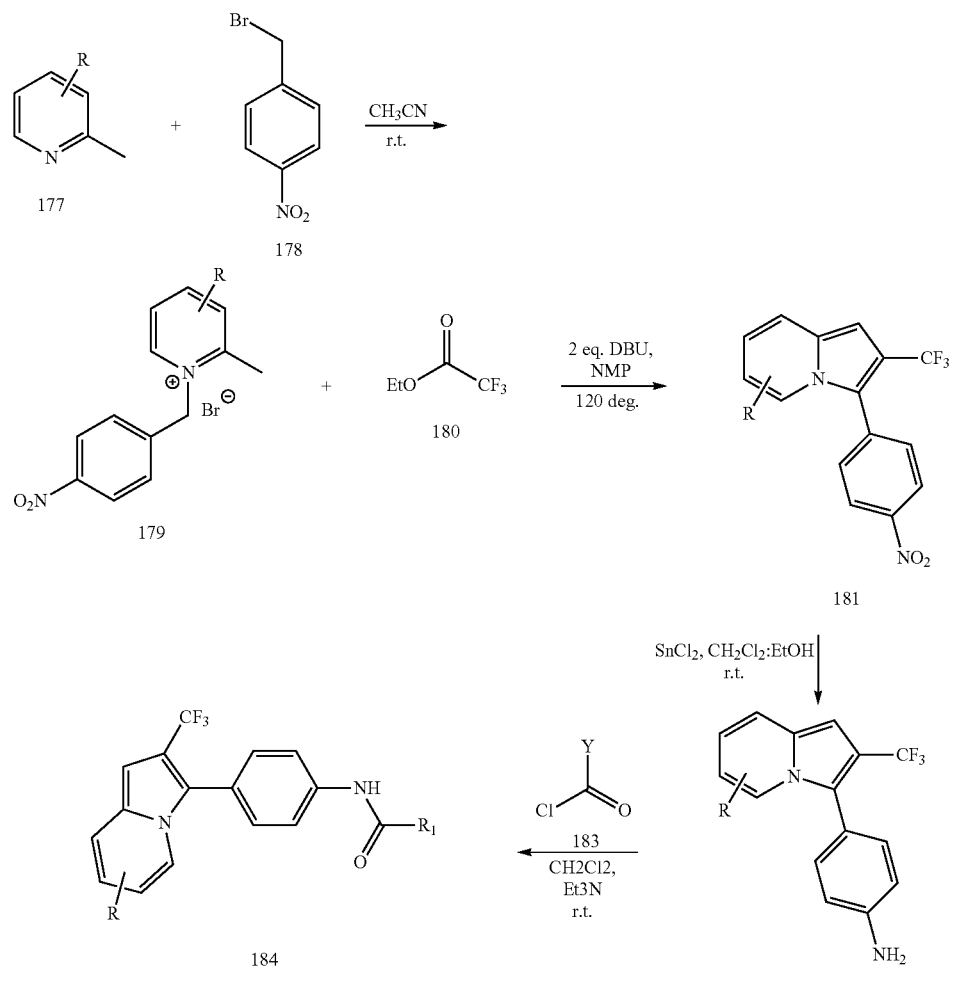

A mixture of (substituted)-2-Picoline (10.73 mmols) (177) and p-nitrobenzylbromide (10.73 mmols) (178) was stirred overnight in 10 mL of acetonitrile at room temperature. The white solid obtained was filtered, washed with acetonitrile and dried to afford 179 in 50%-95% yields.

A mixture of the salt 179 (3.23 mmols), ethyltrifluoroacetate 180 (3.23 mmols) and DBU (6.47 mmols) in 5 mL of anhydrous NMP was heated in a pressure tube at 130-140° C. for 0.5-8 h. The tube was cooled, the contents were poured into 100 mL of water and the product was extracted with ethyl acetate (15 mL×3). The combined extracts were washed with brine and dried over anhydrous $Na_2SO_4$. Concentration followed by column chromatography on silica gel using a mixture of hexane/EtOAc to afford the cyclized product 181 in 10%-80% yields.

To a stirred solution of 181 (1.31 mmols) in 20 mL of 1:1 $CH_2Cl_2$:EtOH, was added of $SnCl_2$ (13.06 mmols) followed by a few drops of water. The mixture was stirred overnight and concentrated. To the residue, was added 20 mL of water and the solution the brought to pH~8-9 using 2N NaOH. The resulting mixture was successively extracted with ethyl acetate (20 mL×4), washed with brine (20 mL) and dried over $Na_2SO_4$. Concentration on Rota vapor afforded 182 in 70-97% yields.

To a solution of 182 (0.30 mmols) in 5 mL of $CH_2Cl_2$, was added the corresponding acyl chloride 183 (0.30 mmols), followed by diisopropyl-ethylamine (0.60 mmols). The resultant mixture was stirred at room temperature for 30 min and eluted through a short pad of silica gel using mixture of hexane:ethyl acetate to afford the product 184 in 80-96% yields.

atmosphere for 24 hrs then filtered through celite and concentrated in vacuo. The resulting oil was purified by silica gel chromatography Hexane:EtOAc (gradient 9:1-1:1) to yield 300 mg (1.1 mmol, 85%) of 4-(2-Trifluoromethyl-5,6,7,8-tetrahydro-indolizin-3-yl)-phenylamine.

Compound 8 was then synthesized from 4-(2-Trifluoromethyl-5,6,7,8-tetrahydro-indolizin-3-yl)-phenylamine and 2,3-difluorobenzoyl chloride in a similar manner as described in Methods 1 or 2.

$^1$H-NMR (CDCl$_3$) δ 8.41 (d, J=10.8 Hz, 1H), 7.93 (m, 1H), 7.70 (d, J=8.4 Hz, 2H), 7.35 (m, 3H), 7.24 (m, 1H), 6.12 (s, 1H), 3.66 (t, J=6.0 Hz, 2H), 2.82 (t, J=6 Hz, 2H), 1.9 (m, 4H).

ESMS clcd for $C_{22}H_{17}F_5N_2O$: 420.13; Found: 421.4 (M+H)$^+$.

Compound 24

Compound 24 was prepared in a similar method as described for Compound 8.

$^1$H-NMR (CDCl$_3$) δ 8.59 (s, 1H), 7.75 (d, J=8.4 Hz, 2H), 7.45 (d, J=8.4 Hz, 2H), 6.25 (s, 1H), 3.76 (t, J=6.0 Hz, 2H), 3.07 (s, 3H), 2.92 (t, J=6 Hz, 2H), 1.9 (m, 4H).

ESMS clcd for $C_{19}H_{17}F_3N_4OS$: 406.1; Found: 407.1 (M+H)$^+$.

J. Synthesis of Compound 44

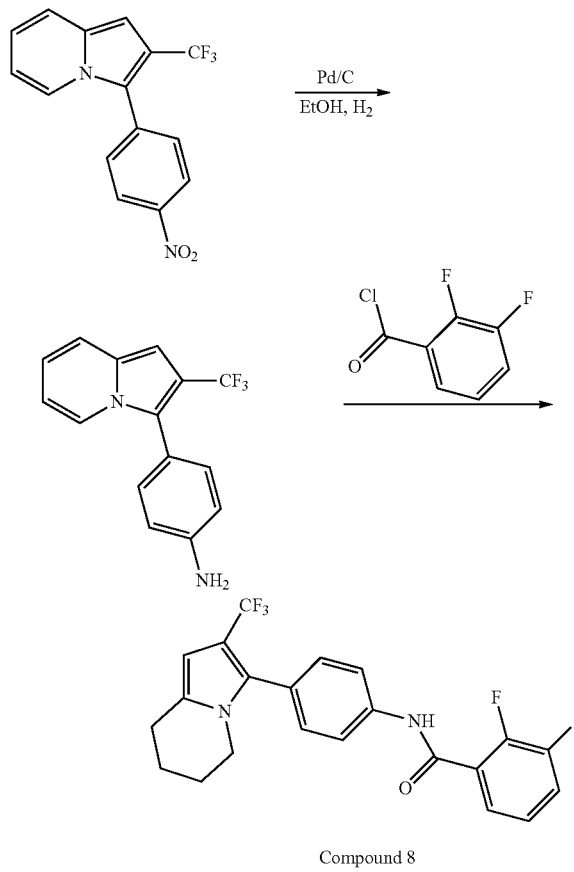

Compound 8

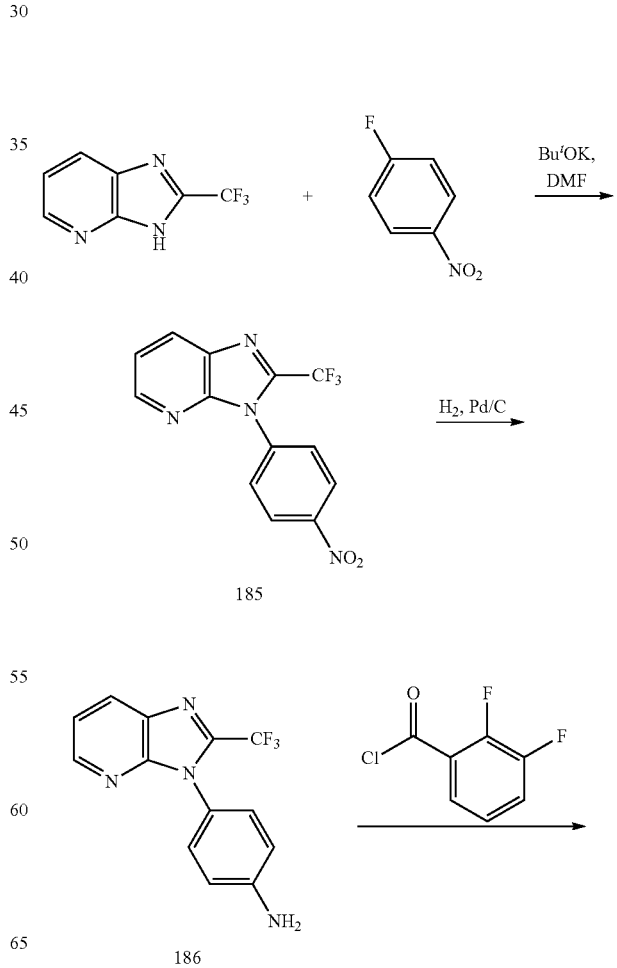

To a solution of 400 mg (1.3 mmol) of 3-(4-Nitro-phenyl)-2-trifluoromethyl-indolizine in 12 mL MeOH was added 200 mg (10%) Pd/C. The solution was allowed to stir under a H$_2$

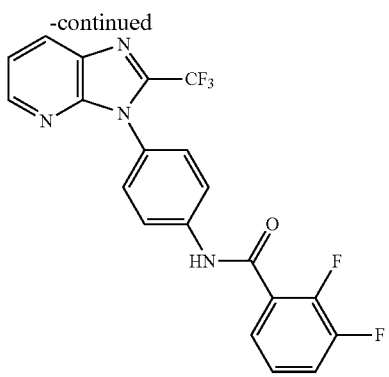

Compound 44

A suspension of a substituted imidazo[4,5-b]pyridyl (27 mmol) and potassium t-butoxide (3.6 g, 30 mmol) in DMF (50 mL) was stirred at room temperature for 30 min. 1-Fluoro-4-nitro-benzene (4.2 g, 30 mmol) was added and the reaction mixture was heated to 150° C. for 4 h. The reaction mixture was diluted with water and extracted with ethyl acetate (EtOAc). The organic extract was washed with water and dried. The oil obtained on concentration was flash chromatographed on silica gel to give 185 in 10-90% yields.

A stirred suspension of compound 185 (12 mmol) in EtOAc (100 mL) and 10% Pd—C (150 mg) was attached to a $H_2$ balloon for 4-12 h. The mixture was filtered through celite and concentrated to give compound 186.

To a mixture of compound 186 (4.0 mmol) and pyridine (1.3 mL) in chloroform (50 mL) at room temperature was added an acid chloride (5.0 mmol). The reaction mixture was stirred for 2-12 h. The reaction mixture was diluted with 1N HCl, extracted with chloroform and dried. The residue obtained on concentration was crystallized from EtOAc/hexane or flash chromatographed to give the product Compound 44 in 30%-95% yield.

$^1$H-NMR (CD$_3$OD) δ 8.45-8.55 (m, 2H), 8.25 (d, 1H, J=8), 7.85-7.95 (m, 3H), 7.35-7.55 (m, 4H), 7.15-7.30 (m, 1H) ppm; ESMS clcd for $C_{20}H_{11}F_5N_5O_4$: 418.0; Found: 419.0 (M+H)$^+$.

K. Synthesis of Compounds 187, 188, and 189

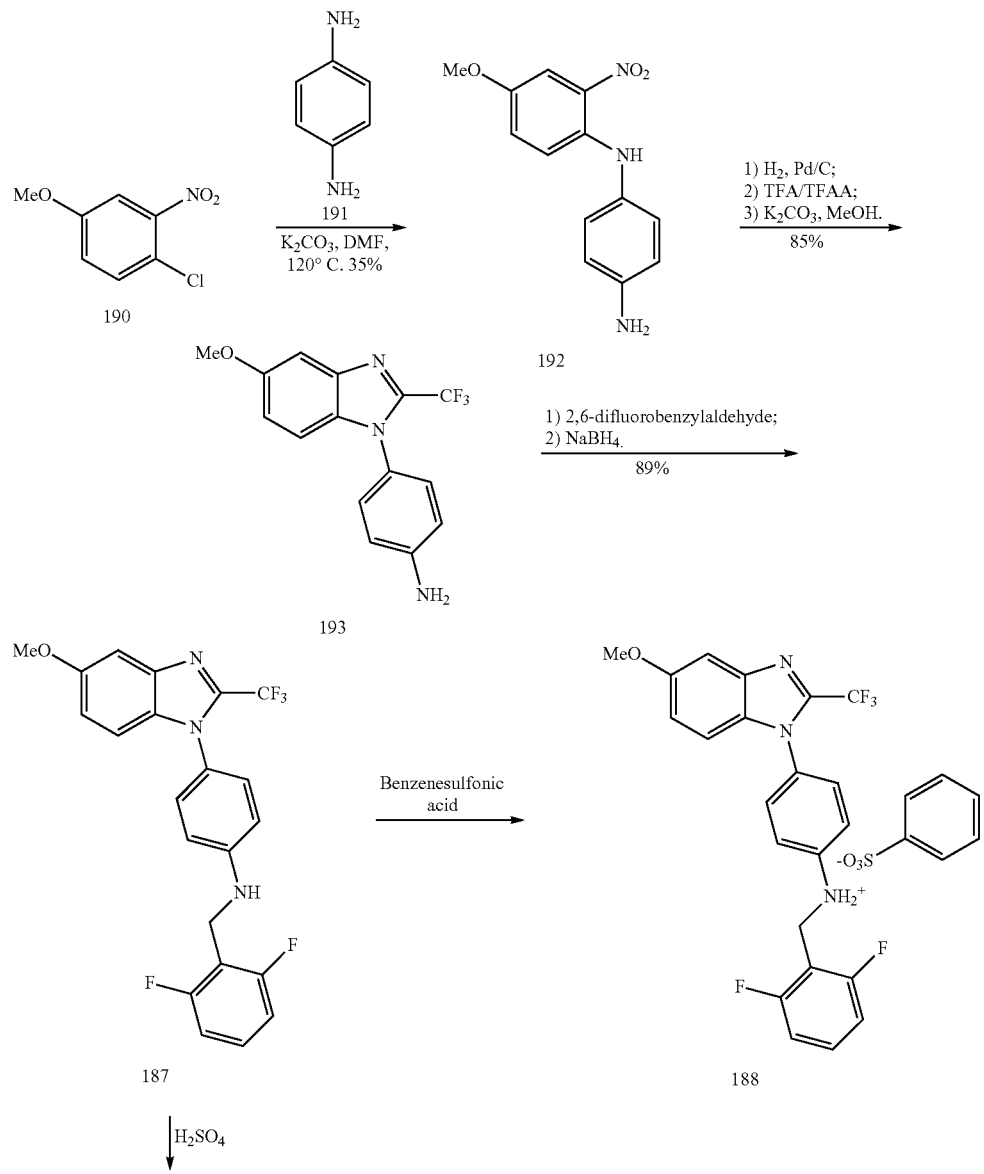

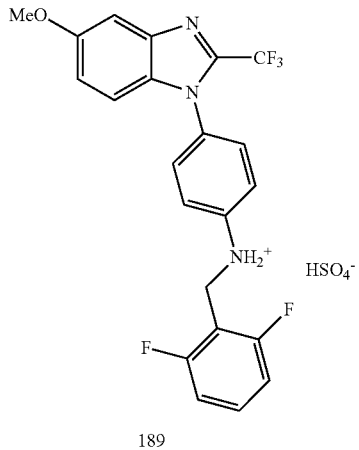

189

To a solution of 4-chloro3-nitroanisole (190, 26.7 mmol) and 1,4-phenylenediamine (191, 134.1 mmol) in DMF (100 mL) was added $K_2CO_3$ (11 g, 79.6 mmol). The reaction mixture was refluxed at 120° C. for 48 h. The solution was allowed to cool to room temperature then ice was added. The solution was washed with $H_2O$ (6×60 mL) and the combined aqueous phase was extracted with ethyl acetate (EtOAc) (2×100 mL). The combined organic phase was washed with $H_2O$ (3×100 mL), dried over $Na_2SO_4$, and concentrated. The concentrate was purified by flash column chromatography (Hexanes:EtOAc=3:1) and afforded 192 as dark brown solid (2.4 g, 35%).

A flask containing a solution of 192 (1.5 g) and Pd/C (200 mg) in 20 mL EtOAc was charged with hydrogen using a hydrogen balloon. The reaction, was stirred overnight then filtered. The filtrate was concentrated and the residue was dissolved in trifluoroacetic acid (TFA) (10 mL, 129.8 mmol) and trifluoroacetic anhydride (TFAA) (2 mL, 14.4 mmol). The resulting solution was refluxed for 2.5 h and then diluted with EtOAc (50 mL) and neutralized with saturated aqueous $NaHCO_3$. The organic phase was dried over $Na_2SO_4$, filtered, and concentrated. The residue was then dissolved in MeOH (40 mL) and to the solution was added $K_2CO_3$ (3.5 g, 25.3 mmol). The solution was refluxed at 80° C. for 20 h before it was filtered and concentrated. The concentrate was purified by column chromatography (Hexanes:EtOAc=3:1) to afford 193 (1.5 g).

To a solution of 193 (1.5 g, 4.88 mmol) in EtOH (50 mL) was added 2,6-difluorobenzylaldehyde (1.1 mL, 10.1 mmol) at room temperature in one shot. After 3 h, $NaBH_4$ (1.1 g, 29.1 mmol) was added to the solution. The reaction solution was stirred overnight and then extracted with $H_2O$/EtOAc. The organic layer was concentrated and the concentrate was purified by column chromatography (Hexanes:EtOAc=5:1) to afford compound 187 (1.9 g).

$^1$H-NMR (CDCl$_3$) δ (ppm) 7.32-7.15 (m, 5H), 7.02-6.91 (m, 4H), 6.82-6.78 (m, 1H), 4.42 (m, 2H), 3.85 (s, 3H); ESMS cacld ($C_{22}H_{16}F_5N_3O$): 433.1; Found: 434.1 (M+H).

To a solution of compound 187 (400 mg, 0.96 mmol) in MeOH (1 mL) was added benzenesulfonic acid (148 mg, 0.94 mmol). The solution was recrystallized by adding ether and the filtration gave compound 188 as white solid (250 mg).

$^1$H-NMR (CDCl$_3$) δ (ppm) 7.92-7.88 (m, 2H), 7.48-7.24 (m, 8H), 7.09-6.79 (m, 6H), 4.71 (s, 2H), 3.86 (s, 3H); ESMS calcd ($C_{22}H_{16}F_5N_3O$): 433.1; Found: 434.0 (M+H).

To a solution of compound 187 (259 mg, 0.60 mmol) in MeOH (2 mL) was added a solution of sulfuric acid (0.04 mL, 0.75 mmol) in 1 mL MeOH. The resulting solution was stirred at room temperature for 1 h before it was concentrated. Recrystallization (MeOH/ether) gave compound 189 as a white solid (220 mg).

$^1$H-NMR ((CD$_3$)$_2$SO) δ (ppm) 7.48-7.35 (m, 2H), 7.22-7.00 (m, 6H), 6.79-6.77 (m, 2H), 6.61 (brs, 2H), 4.29 (s, 2H), 3.79 (s, 3H); ESMS calcd ($C_{22}H_{16}F_5N_3O$): 433.1; Found: 434.1 (M+H).

Representative Analytical Data for Other Exemplary Compounds of this Invention:

Compound 1: Found: 465.4 (M+H)$^+$.
Compound 2: Found: 465.4 (M+H)$^+$.
Compound 4: Found: 447.4 (M+H)$^+$.
Compound 5: Found: 426.4 (M+H)$^+$.
Compound 7: Found: 498.3 (M+H)$^+$.
Compound 10: Found: 456.4 (M+H)$^+$.
Compound 12: Found: 433.4 (M+H)$^+$.
Compound 13: Found: 450.2 (M+H)$^+$.
Compound 14: Found: 447.4 (M+H)$^+$.
Compound 15: Found: 433.8 (M+H)$^+$.
Compound 16: Found: 450.3 (M+H)$^+$.
Compound 17: Found: 431.4 (M+H)$^+$.
Compound 18: Found: 498.4 (M+H)$^+$.
Compound 19: Found: 420.4 (M+H)$^+$.
Compound 20: Found: 442.3 (M+H)$^+$.
Compound 23: Found: 383.8 (M+H)$^+$.
Compound 25: Found: 451.8 (M+H)$^+$.
Compound 26: Found: 417.3 (M+H)$^+$.
Compound 28: Found: 428.2 (M+H)$^+$.
Compound 29: Found: 403.4 (M+H)$^+$.
Compound 30: Found: 485.3 (M+H)$^+$.
Compound 31: Found: 532.5 (M+H)$^+$.
Compound 32: Found: 477.4 (M+H)$^+$.
Compound 33: Found: 475.2 (M+H)$^+$.
Compound 35: Found: 473.4 (M+H)$^+$.
Compound 36: Found: 418.3 (M+H)$^+$.
Compound 37: Found: 442.3 (M+H)$^+$.
Compound 38: Found: 451.8 (M+H)$^+$.
Compound 39: Found: 432.4 (M+H)$^+$.
Compound 40: Found: 411.4 (M+H)$^+$.
Compound 41: Found: 418.3 (M+H)$^+$.
Compound 42: Found: 445.4 (M+H)$^+$.
Compound 43: Found: 432.4 (M+H)$^+$.
Compound 46: Found: 417.3 (M+H)$^+$.

Compound 48: Found: 425.4 (M+H)+.
Compound 49: Found: 391.4 (M+H)+.
Compound 50: Found: 432.4 (M+H)+.
Compound 51: Found: 416.3 (M+H)+.
Compound 52: Found: 453.4 (M+H)+.
Compound 53: Found: 474.4 (M+H)+.
Compound 54: Found: 349.3 (M+H)+.
Compound 55: Found: 431.4 (M+H)+.
Compound 56: Found: 418.3 (M+H)+.
Compound 57: Found: 562.5 (M+H)+.
Compound 58: Found: 357.4 (M+H)+.
Compound 59: Found: 363.4 (M+H)+.
Compound 60: Found: 449.3 (M+H)+.
Compound 61: Found: 418.3 (M+H)+.
Compound 62: Found: 404.4 (M+H)+.
Compound 63: Found: 514.7 (M+H)+.
Compound 64: Found: 485.3 (M+H)+.
Compound 65: Found: 495.4 (M+H)+.
Compound 66: Found: 467.5 (M+H)+.
Compound 67: Found: 540.5 (M+H)+.
Compound 68: Found: 540.5 (M+H)+.
Compound 71: Found: 483.3 (M+H)+.
Compound 72: Found: 487.5 (M+H)+.
Compound 73: Found: 537.3 (M+H)+.
Compound 76 Found: 425.4 (M+H)+.
Compound 78: Found: 456.4 (M+H)+.
Compound 80: Found: 479.4 (M+H)+.
Compound 84: Found: 389.4 (M+H)+.
Compound 85: Found: 453.5 (M+H)+.
Compound 86: Found: 417.4 (M+H)+.
Compound 87: Found: 433.5 (M+H)+.
Compound 88: Found: 419.4 (M+H)+.
Compound 89: Found: 441.4 (M+H)+.
Compound 90: Found: 451.4 (M+H)+.
Compound 92: Found: 455.4 (M+H)+.
Compound 93: Found: 474.4 (M+H)+.
Compound 94: Found: 431.4 (M+H)+.
Compound 95: Found: 425.4 (M+H)+.
Compound 97: Found: 501.3 (M+H)+.
Compound 98: Found: 447.4 (M+H)+.
Compound 100: Found: 447.4 (M+H)+.
Compound 102: Found: 480.3 (M+H)+.
Compound 103: Found: 447.4 (M+H)+.
Compound 104: Found: 490.3 (M+H)+.
Compound 107: Found: 456.4 (M+H)+.
Compound 108: Found: 445.8 (M+H)+.
Compound 109: Found: 445.8 (M+H)+.
Compound 110: Found: 447.4 (M+H)+.
Compound 113: Found: 460.4 (M+H)+.
Compound 115: Found: 537.3 (M+H)+.
Compound 117: Found: 480.3 (M+H)+.
Compound 118: Found: 490.3 (M+H)+.
Compound 119: Found: 490.3 (M+H)+.
Compound 120: Found: 401.3 (M+H)+.
Compound 121: Found: 500.4 (M+H)+.
Compound 122: Found: 361.3 (M+H)+.
Compound 123: Found: 455.4 (M+H)+.
Compound 124: Found: 457.5 (M+H)+.
Compound 125: Found: 435.4 (M+H)+.
Compound 126: Found: 445.8 (M+H)+.
Compound 127: Found: 547.4 (M+H)+.
Compound 128: Found: 441.4 (M+H)+.
Compound 129: Found: 547.4 (M+H)+.
Compound 130: Found: 485.5 (M+H)+.
Compound 131: Found: 485.5 (M+H)+.
Compound 132: Found: 475.4 (M+H)+.
Compound 133: Found: 459.4 (M+H)+.
Compound 135: Found: 469.8 (M+H)+.

Example 2

Inhibition of IL-2 Production

Jurkat cells were placed in a 96 well plate (0.5 million cells per well in 1% FBS medium) then test compounds of this invention were added at different concentrations. After 10 minutes, the cells were activated with PHA (final concentration 2.5 µg/mL) and incubated for 20 hours at 37° C. under $CO_2$. The final volume was 200 µL. Following incubation, the cells were centrifuged and the supernatants collected and stored at −70° C. prior to assaying for IL-2 production. A commercial kit (IL-2 Eli-pair, Diaclone Research, Besancon, France) was used to detect production of IL-2, from which dose response curves were obtained. The $IC_{50}$ value was calculated as the concentration at which 50% of maximum IL-2 production after stimulation was inhibited versus a non-stimulation control.

| $IC_{50}$ | Compounds |
| --- | --- |
| <100 nM | 1, 2, 3, 4, 5, 6, 7, 8, 9, 10, 11, 12, 13, 14, 71, 96, 97, 98, 99, 100, 101, 102, 103, 104, 105, 106, 107, 108, 109, 110, 111, 112, 113, 114, 115, 116, 117, 118, 119, 132, 135, 187 |
| 100-500 nM | 15, 16, 17, 18, 19, 20, 21, 22, 23, 24, 25, 26, 27, 28, 29, 30, 31, 32, 33, 34, 35, 36, 37, 38, 39, 40, 63, 64, 65, 66, 69, 70, 72, 73, 74, 75, 76, 77, 78, 79, 80, 81, 82, 83, 84, 85, 86, 87, 88, 89, 90, 133, 134, 136 |
| 500 nM-1 µM | 41, 42, 43, 44, 45, 46, 47, 48, 56, 91, 92, 93, 94, 95 |
| >1 µM | 49, 50, 51, 52, 53, 54, 55, 57, 58, 59, 60, 61, 62, 67, 68, 120, 121, 122, 123, 124, 125, 126, 127, 128, 129, 130, 131 |

Example 3

Activation of TRPM4 Channel

TRPM4 currents were measured in Jurkat cells and HEK-293 cells overexpressing TRPM4. The external solution contained the following (mM): NaCl 140, KCl 2.8, $MgCl_2$ 2, $CaCl_2$ 1, glucose 10, and HEPES-NaOH 10 (ph 72). The internal solution contained the following (mM): K-glutamate 120, NaCl 8, $MgCl_2$ 1, K-BAPTA 10, HEPES-CsOH 10 (ph 7.2). Ramps were given every 2 s (−100 to +100 mV in 50 ms) and cells were held at −80 mV between ramps. Free intracellular calcium was adjusted to 300 nM.

Representative compounds of this invention, including Compounds 9, were found to activate TRPM4 channels using this method.

Example 4

Patch Clamp Studies of Inhibition of $I_{crac}$ Current in RBL Cells, Jurkat Cells, and Primary T Cells In general, a whole cell patch clamp method was used to examine the effects of a compound of the invention on a channel that mediates $I_{crac}$. In such experiments, a baseline measurement was established for a patched cell. Then a compound to be tested was perfused (or puffed) to cells in the external solution and the effect of the compound on $I_{crac}$ was measured. A compound that modulates $I_{crac}$ (e.g., inhibits) is a compound that is useful in the invention for modulating CRAC ion channel activity.

1) RBL Cells

Cells

Rat basophilic leukemia cells (RBL-2H3) were grown in DMEM media supplemented with 10% fetal bovine serum in an atmosphere of 95% air/5% $CO_2$. Cells were seeded on glass coverslips 1-3 days before use.

Recording Conditions

Membrane currents of individual cells were recorded using the whole-cell configuration of the patch clamp technique with an EPC10 (HEKA Electronik, Lambrecht, Germany). Electrodes (2-5 MO in resistance) were fashioned from borosilicate glass capillary tubes (Sutter Instruments, Novato, Ca.). The recordings were done at room temperature.

Intracellular Pipette Solution

Cs-Glutamate 120 mM; CsCl 20 mM; CsBAPTA 10 mM; CsHEPES 10 mM; NaCl 8 mM; $MgCl_2$ 1 mM; IP3 0.02 mM; pH=7.4 adjusted with CsOH. (Shielded from light and kept on ice before experiment)

Extracellular Solution

NaCl 138 mM; NaHEPES, 10 mM; CsCl 10 mM; $CaCl_2$ 10 mM; Glucose 5.5 mM; KCl 5.4 mM; $KH_2PO_4$ 0.4 mM; $Na_2HPO_4.H_2$ 0.3 mM at pH=7.4 adjusted with NaOH.

Compound Treatment

Each compound was diluted from a 10 mM stock in series using DMSO (1 µM, 3.2 µM, 1 µM, 31.6 nM, 100 nM 32 nM). The final DMSO concentration was always kept at 0.1%.

Experimental Procedure $I_{CRAC}$ currents were monitored every 2 seconds using a 50 msec protocol, where the voltage was ramped from −100 mV to +100 mV. The membrane potential was held at 0 mV between the test ramps. In a typical experiment the peak inward currents would develop within 50-100 seconds. Once the $I_{CRAC}$ currents were stabilized, the cells were perfused with compounds in the extracellular solution. At the end of an experiment the remaining $I_{CRAC}$ currents were then challenged with a control compound (SKF96365, 10 µM) to ensure that the current could still be inhibited.

Data Analysis

The $I_{CRAC}$ current level was determined by measuring the inward current amplitude at −80 mV of the voltage ramp in an off-line analysis using MATLAB. The $I_{CRAC}$ current inhibition, for each concentration was calculated using peak amplitude in the beginning of the experiment from the same cell. The $IC_{50}$ value and Hill coefficient for each compound was estimated by fitting all the individual data points to a single Hill equation.

2) Jurkat Cells

Cells

Jurkat T cells were grown on glass coverslips, transferred to the recording chamber and kept in a standard modified Ringers solution of the following composition: NaCl 145 mM, KCl 2.8 mM, CsCl 10 mM, $CaCl_2$ 10 mM, $MgCl_2$ 2 mM, glucose 10 mM, HEPES.NaOH 10 mM, pH 7.2.

Extracellular Solution

The external solution contained 10 mM CaNaR, 11.5 mM glucose and the test compound at the concentrations described below.

Intracellular Pipette Solution

The standard intracellular pipette solution contained: Cs-glutamate 145 mM, NaCl 8 mM, $MgCl_2$ 1 mM, ATP 0.5 mM, GTP 0.3 mM, pH 7.2 adjusted with CsOH. The solution was supplemented with a mixture of 10 mM Cs-BAPTA and 4.3-5.3 mM $CaCl_2$ to buffer $[Ca^{2+}]i$ to resting levels of 100-150 nM.

Patch-Clamp Recordings

Patch-clamp experiments were performed in the tight-seal whole-cell configuration at 21-25° C. High-resolution current recordings were acquired by a computer-based patch-clamp amplifier system (EPC-9, HEKA, Lambrecht, Germany). Sylgard®-coated patch pipettes had resistances between 2-4 MO after filling with the standard intracellular solution. Immediately following establishment of the whole-cell configuration, voltage ramps of 50 ms duration spanning the voltage range of −100 to +100 mV were delivered from a holding potential of 0 mV at a rate of 0.5 Hz over a period of 300 to 400 seconds. All voltages were corrected for a liquid junction potential of 10 mV between external and internal solutions. Currents were filtered at 2.3 kHz and digitized at 100 µs intervals. Capacitive currents and series resistance were determined and corrected before each voltage ramp using the automatic capacitance compensation of the EPC-9.

Data Analysis

The very first ramps before activation of $I_{CRAC}$ (usually 1 to 3) were digitally filtered at 2 kHz, pooled and used for leak-subtraction of all subsequent current records. The low-resolution temporal development of inward currents was extracted from the leak-corrected individual ramp current records by measuring the current amplitude at −80 mV or a voltage of choice.

3) Primary T Cells

Preparation of Primary T Cells

Primary T cells were obtained from human whole blood samples by adding 100 µL of RosetteSep® human T cell enrichment cocktail to 2 mL of whole blood. The mixture was incubated for 20 minutes at room temperature, then diluted, with an equal volume of PBS containing 2% FBS. The mixture was layered on top of RosetteSep® DM-L density medium and then centrifuged for 20 minutes at 1200 g at room temperature. The enriched T cells were recovered from the plasma/density medium interface, then washed with PBS containing 2% FBS twice, and used in patch clamp experiments following the procedure described for RBL cells.

Results:

Certain compounds of the invention were found to decrease $I_{CRAC}$ current.

Example 5

Patch clamp studies of inhibition of Kv1.3 in Jurkat T Cells

Cells

Jurkat T cells were grown on glass coverslips, transferred to the recording chamber and kept in a standard modified Ringer's solution of the following composition: NaCl 145 mM, KCl 2.8 mM, CsCl 10 mM, $CaCl_2$ 10 mM, $MgCl_2$ 2 mM, glucose 10 mM, HEPES NaOH 10 mM, pH 7.2.

Extracellular Solution

The external solution contained 1 mM $CaCl_2$, 140 mM NaCl, 2.8 mM KCl, 2 mM $MgCl_2$ and the test compound at the concentrations described below.

Intracellular Pipette Solution

The standard intracellular pipette solution contained: 140 mM potassium glutamate, 8 mM NaCl, 1 mM MgCl2, 10 mM potassium bapta, 10 mM Hepes-KOH.

Patch-Clamp Recordings

Patch-clamp experiments were performed in the tight-seat whole-cell configuration at 21-25° C. High-resolution current recordings were acquired by a computer-based patch-clamp amplifier system (EPC-9, HEKA, Lambrecht, Germany). Sylgard®-coated patch pipettes had resistances between 24 MΩ after filling with the standard intracellular solution. Immediately following establishment of the whole-cell configuration, voltage ramps of 50 ms duration spanning the voltage range of −80 to +80 mV were delivered from a holding potential of 0 mV at a rate of 0.5 Hz over a period of 300 to 400 seconds.

Results

Certain compounds of the invention, including Compound 1, were found to inhibit Kv1.3 in Jurkat T cells.

Example 6

Inhibition of Multiple Cytokines in Primary Human PBMCs

Peripheral blood mononuclear cells (PBMCs) were stimulated with phytohemagglutinin (PHA) in the presence of varying concentrations of compounds of the invention or cyclosporine A (CsA), a known inhibitor of cytokine production. Cytokine production was measured using commercially available human ELISA assay kits (from Cell Science, Inc.) following the manufacturers instructions.

Table 2 shows the concentration of CsA and compounds 1 and 135 which inhibit 50% of a cytokine production. As can be seen from the data, compounds 31, 66, and 75 are potent inhibitors of IL-2, IL-4, IL-5, IL-13, GM-CSF, INF-γ and TNF-α. In addition, compounds of the invention do not inhibit the anti-inflammatory cytokine, IL-10.

TABLE 2

IC$_{50}$ values for cytokine inhibition.

| Cpd # | IL-2 | IL-4 | IL-5 | IL-10 | IL-13 | GM-CSF | INF-γ | TNF-α |
|---|---|---|---|---|---|---|---|---|
| CsA | 3 | 25 | 7 | 948 | 67 | 109 | 18 | 26 |
| 1 | 29 | 651 | 26 | >1000 | 73 | 788 | 95 | 424 |
| 135 | 3 | 101 | 13 | 439 | 25 | 99 | 29 | 47 |

All publications, patent applications, patents, and other documents cited herein are incorporated by reference in their entirety. In case of conflict, the present specification, including definitions, will control. In addition, the materials, methods, and examples are illustrative only and not intended to be limiting in any way.

We claim:

1. A method of inhibiting immune cell activation comprising administering to the cell a compound represented by formula (I):

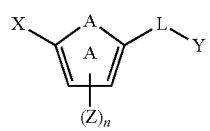

(I)

or a pharmaceutically acceptable salt thereof wherein:

X is an optionally substituted benzoimidazolyl, an optionally substituted 5,6,7,8-tetrahydroindolizinyl, an optionally substituted imidazo[4,5-a]pyridyl, an optionally substituted imidazo[1,2-a]pyridyl, an optionally substituted imidazo[4,5-b]pyridyl, or an optionally substituted imidazo[4,5-c]pyridyl;

Y is an unsubstituted alkyl, an optionally substituted alkenyl, an optionally substituted cycloalkyl, an optionally substituted cycloalkenyl, an optionally substituted aryl, an optionally substituted heteroaryl, or an optionally substituted heteroaralkyl;

A is —O—, —S(O)$_p$—, —NH—, —NZ—, —CH═CH—, —CZ═CH—, —CH═CZ—, —CZ═CZ—, —N═CH—, —N═CZ—, —CH═N—, —CZ═N—, or an N-oxide of —N═CH—, —N═CZ—, —CH═N—, or —CZ═N—; wherein when X is an optionally substituted benzoimidazolyl, A is not —CH═CH—, —CZ═CH—, —CH═CZ—, or —CZ═CZ—;

Z, for each occurrence, is independently selected from the group consisting of an optionally substituted alkyl, an optionally substituted alkenyl, an optionally substituted alkynyl, an optionally substituted cycloalkyl, an optionally substituted cycloalkenyl, an optionally substituted heterocyclyl, an optionally substituted aryl, an optionally substituted heteroaryl, an optionally substituted aralkyl, an optionally substituted heteraralkyl, a haloalkyl, —C(O)NR$_1$R$_2$, —NR$_4$C(O)R$_5$, halo, —OR$_4$, cyano, nitro, haloalkoxy, —C(O)R$_4$, —NR$_1$R$_2$, —C(O)OR$_4$, —OC(O)R$_4$, —NR$_4$C(O)NR$_1$R$_2$, —OC(O)NR$_1$R$_2$, —NR$_4$C(O)OR$_5$, —S(O)$_p$R$_4$, or —S(O)$_h$NR$_1$R$_2$;

L is a linker selected from the group consisting of an optionally substituted lower alkyl, and optionally substituted lower alkenyl, —NRCR$_4$R$_5$—, —C(O)—, —OC(O)—, —C(O)O—, —NR—C(O)—, —C(O)—NR—, —NR—C(O)—NR—, —C(S)—, —NR—S(O)$_h$—, —S(O)$_h$—NR—, —NR—C(═NR)—, —NR—C(═NR)—NR—, —NR—C(═N—CN)—NR—, —NR—C(═N—NO$_2$)—NR—, —NR—C(S)—, —C(S)—NR—, or —NR—C(S)—NR—;

R, for each occurrence, is independently selected from —H, an alkyl, acetyl, alkoxycarbonyl, or aralkoxycarbonyl;

R$_1$ and R$_2$, for each occurrence are, independently, H, an optionally substituted alkyl, an optionally substituted alkenyl, an optionally substituted alkynyl, an optionally substituted cycloalkyl, an optionally substituted cycloalkenyl, an optionally substituted heterocyclyl, an optionally substituted aryl, an optionally substituted heteroaryl, an optionally substituted aralkyl, or an optionally substituted heteraralkyl; or R$_1$ and R$_2$ taken together with the nitrogen to which they are attached is optionally substituted heterocyclyl or optionally substituted heteroaryl;

R$_4$ and R$_5$ for each occurrence are, independently, H, an optionally substituted alkyl, an optionally substituted alkenyl, an optionally substituted alkynyl, an optionally substituted cycloalkyl, an optionally substituted cycloalkenyl, an optionally substituted heterocyclyl, an optionally substituted aryl, an optionally substituted heteroaryl, an optionally substituted aralkyl, or an optionally substituted heteraralkyl;

h is 1 or 2;

n is 0 or an integer from 1 to 4; and p, for each occurrence, is, independently, 0, 1, or 2.

2. The method of claim 1, wherein immune cell activation is inhibited in a subject by administering the compound to the subject.

3. The method of claim 2, wherein the subject is human.

4. A method of inhibiting cytokine production in a cell, comprising administering to the cell a compound represented by formula (I):

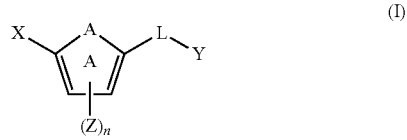

or a pharmaceutically acceptable salt wherein:

X is an optionally substituted benzoimidazolyl, an optionally substituted 5,6,7,8-tetrahydroindolizinyl, an optionally substituted imidazo[4,5-a]pyridyl, an optionally substituted imidazo[1,2-a]pyridyl, an optionally substituted imidazo[4,5-b]pyridyl, or an optionally substituted imidazo[4,5-c]pyridyl;

Y is an unsubstituted alkyl, an optionally substituted alkenyl, an optionally substituted cycloalkyl, an optionally substituted cycloalkenyl, an optionally substituted aryl, an optionally substituted heteroaryl, or an optionally substituted heteroaralkyl;

A is —O—, —S(O)$_p$—, —NH—, —NZ—, —CH=CH—, —CZ=CH—, —CH=CZ—, —CZ=CZ—, —N=CH—, —N=CZ—, —CH=N—, —CZ=N—, or an N-oxide of —N=CH—, —N=CZ—, —CH=N—, or —CZ=N—; wherein when X is an optionally substituted benzoimidazolyl, A is not —CH=CH—, —CZ=CH—, —CH=CZ—, or —CZ=CZ—;

Z, for each occurrence, is independently selected from the group consisting of an optionally substituted alkyl, an optionally substituted alkenyl, an optionally substituted alkynyl, an optionally substituted cycloalkyl, an optionally substituted cycloalkenyl, an optionally substituted heterocyclyl, an optionally substituted aryl, an optionally substituted heteroaryl, an optionally substituted aralkyl, an optionally substituted heteraralkyl, a haloalkyl, —C(O)NR$_1$R$_2$, —NR$_4$C(O)R$_5$, halo, —OR$_4$, cyano, nitro, haloalkoxy, —C(O)R$_4$, —NR$_1$R$_2$, —C(O)OR$_4$, —OC(O)R$_4$, —NR$_4$C(O)NR$_1$R$_2$, —OC(O)NR$_1$R$_2$, —NR$_4$C(O)OR$_5$, —S(O)$_p$R$_4$, or —S(O)$_h$NR$_1$R$_2$;

L is a linker selected from the group consisting of an optionally substituted lower alkyl, and optionally substituted lower alkenyl, —NRCR$_4$R$_5$—, —C(O)—, —OC(O)—, —C(O)O—, —NR—C(O)—, —C(O)—NR—, —NR—C(O)—NR—, —C(S)—, —NR—S(O)$_h$—, —S(O)$_h$—NR—, —NR—C(=NR)—, —NR—C(=NR)—NR—, —NR—C(=N—CN)—NR—, —NR—C(=N—NO$_2$)—NR—, —NR—C(S)—, —C(S)—NR—, or —NR—C(S)—NR—;

R, for each occurrence, is independently selected from —H, an alkyl, acetyl, alkoxycarbonyl, or aralkoxycarbonyl;

R$_1$ and R$_2$, for each occurrence are, independently, H, an optionally substituted alkyl, an optionally substituted alkenyl, an optionally substituted alkynyl, an optionally substituted cycloalkyl, an optionally substituted cycloalkenyl, an optionally substituted heterocyclyl, an optionally substituted aryl, an optionally substituted heteroaryl, an optionally substituted aralkyl, or an optionally substituted heteraralkyl; or R$_1$ and R$_2$ taken together with the nitrogen to which they are attached is optionally substituted heterocyclyl or optionally substituted heteroaryl;

R$_4$ and R$_5$ for each occurrence are, independently, H, an optionally substituted alkyl, an optionally substituted alkenyl, an optionally substituted alkynyl, an optionally substituted cycloalkyl, an optionally substituted cycloalkenyl, an optionally substituted heterocyclyl, an optionally substituted aryl, an optionally substituted heteroaryl, an optionally substituted aralkyl, or an optionally substituted heteraralkyl;

h is 1 or 2;

n is 0 or an integer from 1 to 4; and p, for each occurrence, is, independently, 0, 1, or 2.

5. The method of claim 4, wherein cytokine production is inhibited in a subject by administering the compound to the subject.

6. The method of claim 5, wherein the subject is human.

7. The method of claim 4, wherein the cytokine which is inhibited is selected from the group consisting of IL-2, IL-4, IL-5, IL-13, GM-CSF, IFN-γ, TNF-α, and combinations thereof.

8. A method of modulating an ion channel by activating a TRPM4 ion channel, inhibiting a Kv1.3 ion channel, or inhibiting a CRAC ion channel in a cell, comprising administering to the cell a compound represented by formula (I):

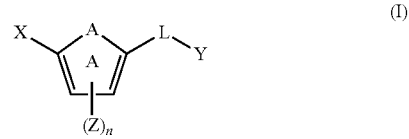

or a pharmaceutically acceptable salt thereof wherein:

X is an optionally substituted benzoimidazolyl, an optionally substituted 5,6,7,8-tetrahydroindolizinyl, an optionally substituted imidazo[4,5-a]pyridyl, an optionally substituted imidazo[1,2-a]pyridyl, an optionally substituted imidazo[4,5-b]pyridyl, or an optionally substituted imidazo[4,5-c]pyridyl;

Y is an unsubstituted alkyl, an optionally substituted alkenyl, an optionally substituted cycloalkyl, an optionally substituted cycloalkenyl, an optionally substituted aryl, an optionally substituted heteroaryl, or an optionally substituted heteroaralkyl;

A is —O—, —S(O)$_p$—, —NH—, —NZ—, —CH=CH—, —CZ=CH—, —CH=CZ—, —CZ=CZ—, —N=CH—, —N=CZ—, —CH=N—, —CZ=N—, or an N-oxide of —N=CH—, —N=CZ—, —CH=N—, or —CZ=N—; wherein when X is an optionally substituted benzoimidazolyl, A is not —CH=CH—, —CZ=CH—, —CH=CZ—, or —CZ=CZ—;

Z, for each occurrence, is independently selected from the group consisting of an optionally substituted alkyl, an optionally substituted alkenyl, an optionally substituted alkynyl, an optionally substituted cycloalkyl, an optionally substituted cycloalkenyl, an optionally substituted heterocyclyl, an optionally substituted aryl, an optionally substituted heteroaryl, an optionally substituted aralkyl, an optionally substituted heteraralkyl, a haloalkyl, —C(O)NR$_1$R$_2$, —NR$_4$C(O)R$_5$, halo, —OR$_4$, cyano, nitro, haloalkoxy, —C(O)R$_4$, —NR$_1$R$_2$, —C(O)

$OR_4$, —$OC(O)R_4$, —$NR_4C(O)NR_1R_2$, —$OC(O)NR_1R_2$, —$NR_4C(O)OR_5$, —$S(O)_pR_4$, or —$S(O)_hNR_1R_2$;

L is a linker selected from the group consisting of an optionally substituted lower alkyl, and optionally substituted lower alkenyl, —$NRCR_4R_5$—, —C(O)—, —OC(O)—, —C(O)O—, —NR—C(O)—, —C(O)—NR—, —NR—C(O)—NR—, —C(S)—, —NR—$S(O)_h$—, —$S(O)_h$—NR—, —NR—C(=NR)—, —NR—C(=NR)—NR—, —NR—C(=N—CN)—NR—, —NR—C(=N—NO$_2$)—NR—, —NR—C(S)—, —C(S)—NR—, or —NR—C(S)—NR—;

R, for each occurrence, is independently selected from —H, an alkyl, acetyl, alkoxycarbonyl, or aralkoxycarbonyl;

$R_1$ and $R_2$, for each occurrence are, independently, H, an optionally substituted alkyl, an optionally substituted alkenyl, an optionally substituted alkynyl, an optionally substituted cycloalkyl, an optionally substituted cycloalkenyl, an optionally substituted heterocyclyl, an optionally substituted aryl, an optionally substituted heteroaryl, an optionally substituted aralkyl, or an optionally substituted heteraralkyl; or $R_1$ and $R_2$ taken together with the nitrogen to which they are attached is optionally substituted heterocyclyl or optionally substituted heteroaryl;

$R_4$ and $R_5$ for each occurrence are, independently, H, an optionally substituted alkyl, an optionally substituted alkenyl, an optionally substituted alkynyl, an optionally substituted cycloalkyl, an optionally substituted cycloalkenyl, an optionally substituted heterocyclyl, an optionally substituted aryl, an optionally substituted heteroaryl, an optionally substituted aralkyl, or an optionally substituted heteraralkyl;

h is 1 or 2;

n is 0 or an integer from 1 to 4; and p, for each occurrence, is, independently, 0, 1, or 2.

9. The method of claim 8, wherein the ion channel is in a subject and it is modulated by administering the compound to the subject.

10. The method of claim 9, wherein the subject is human.

11. The method of claim 8, wherein the ion channel is a CRAC ion channel.

12. The method of claim 8, wherein the ion channel is a TRPM4 or Kv1.3 ion channel.

13. A method of inhibiting immune cell proliferation in response to an antigen, comprising administering to the cell a compound represented by formula (I):

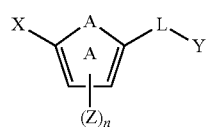

(I)

or a pharmaceutically acceptable salt thereof wherein:

X is an optionally substituted benzoimidazolyl, an optionally substituted 5,6,7,8-tetrahydroindolizinyl, an optionally substituted imidazo[4,5-a]pyridyl, an optionally substituted imidazo[1,2-a]pyridyl, an optionally substituted imidazo[4,5-b]pyridyl, or an optionally substituted imidazo[4,5-c]pyridyl;

Y is an unsubstituted alkyl, an optionally substituted alkenyl, an optionally substituted cycloalkyl, an optionally substituted cycloalkenyl, an optionally substituted aryl, an optionally substituted heteroaryl, or an optionally substituted heteroaralkyl;

A is —O—, —$S(O)_p$—, —NH—, —NZ—, —CH=CH—, —CZ=CH—, —CH=CZ—, —CZ=CZ—, —N=CH—, —N=CZ—, —CH=N—, —CZ=N—, or an N-oxide of —N=CH—, —N=CZ—, —CH=N—, or —CZ=N—; wherein when X is an optionally substituted benzoimidazolyl, A is not —CH=CH—, —CZ=CH—, —CH=CZ—, or —CZ=CZ—;

Z, for each occurrence, is independently selected from the group consisting of an optionally substituted alkyl, an optionally substituted alkenyl, an optionally substituted alkynyl, an optionally substituted cycloalkyl, an optionally substituted cycloalkenyl, an optionally substituted heterocyclyl, an optionally substituted aryl, an optionally substituted heteroaryl, an optionally substituted aralkyl, an optionally substituted heteraralkyl, a haloalkyl, —$C(O)NR_1R_2$, —$NR_4C(O)R_5$, halo, —$OR_4$, cyano, nitro, haloalkoxy, —$C(O)R_4$, —$NR_1R_2$, —$C(O)OR_4$, —$OC(O)R_4$, —$NR_4C(O)NR_1R_2$, —$OC(O)NR_1R_2$, —$NR_4C(O)OR_5$, —$S(O)_pR_4$, or —$S(O)_hNR_1R_2$;

L is a linker selected from the group consisting of an optionally substituted lower alkyl, and optionally substituted lower alkenyl, —$NRCR_4R_5$—, —C(O)—, —OC(O)—, —C(O)O—, —NR—C(O)—, —C(O)—NR—, —NR—C(O)—NR—, —C(S)—, —NR—$S(O)_h$—, —$S(O)_h$—NR—, —NR—C(=NR)—, —NR—C(=NR)—NR—, —NR—C(=N—CN)—NR—, —NR—C(=N—NO$_2$)—NR—, —NR—C(S)—, —C(S)—NR—, or —NR—C(S)—NR—;

R, for each occurrence, is independently selected from —H, an alkyl, acetyl, alkoxycarbonyl, or aralkoxycarbonyl;

$R_1$ and $R_2$, for each occurrence are, independently, H, an optionally substituted alkyl, an optionally substituted alkenyl, an optionally substituted alkynyl, an optionally substituted cycloalkyl, an optionally substituted cycloalkenyl, an optionally substituted heterocyclyl, an optionally substituted aryl, an optionally substituted heteroaryl, an optionally substituted aralkyl, or an optionally substituted heteraralkyl; or $R_1$ and $R_2$ taken together with the nitrogen to which they are attached is optionally substituted heterocyclyl or optionally substituted heteroaryl;

$R_4$ and $R_5$ for each occurrence are, independently, H, an optionally substituted alkyl, an optionally substituted alkenyl, an optionally substituted alkynyl, an optionally substituted cycloalkyl, an optionally substituted cycloalkenyl, an optionally substituted heterocyclyl, an optionally substituted aryl, an optionally substituted heteroaryl, an optionally substituted aralkyl, or an optionally substituted heteraralkyl;

h is 1 or 2;

n is 0 or an integer from 1 to 4; and p, for each occurrence, is, independently, 0, 1, or 2.

14. The method of claim 13, wherein immune cell proliferation is inhibited in a subject by administering the compound to the subject.

15. The method of claim 14, wherein the immune cell is a T-cell, B-cell, and/or mast cell.

16. The method of claim 14, wherein the subject is human.

17. A method for treating an inflammatory condition in a subject in need thereof, comprising administering to the subject an effective amount of a compound represented by formula (I):

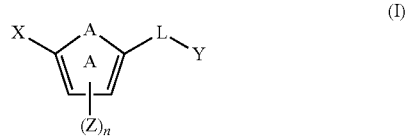

or a pharmaceutically acceptable salt thereof wherein:

X is an optionally substituted benzoimidazolyl, an optionally substituted 5,6,7,8-tetrahydroindolizinyl, an optionally substituted imidazo[4,5-a]pyridyl, an optionally substituted imidazo[1,2-a]pyridyl, an optionally substituted imidazo[4,5-b]pyridyl, or an optionally substituted imidazo[4,5-c]pyridyl;

Y is an unsubstituted alkyl, an optionally substituted alkenyl, an optionally substituted cycloalkyl, an optionally substituted cycloalkenyl, an optionally substituted aryl, an optionally substituted heteroaryl, or an optionally substituted heteroaralkyl;

A is —O—, —S(O)$_p$—, —NH—, —NZ—, —CH=CH—, —CZ=CH—, —CH=CZ—, —CZ=CZ—, —N=CH—, —N=CZ—, —CH=N—, —CZ=N—, or an N-oxide of —N=CH—, —N=CZ—, —CH=N—, or —CZ=N—; wherein when X is an optionally substituted benzoimidazolyl, A is not —CH=CH—, —CZ=CH—, —CH=CZ—, or —CZ=CZ—;

Z, for each occurrence, is independently selected from the group consisting of an optionally substituted alkyl, an optionally substituted alkenyl, an optionally substituted alkynyl, an optionally substituted cycloalkyl, an optionally substituted cycloalkenyl, an optionally substituted heterocyclyl, an optionally substituted aryl, an optionally substituted heteroaryl, an optionally substituted aralkyl, an optionally substituted heteraralkyl, a haloalkyl, —C(O)NR$_1$R$_2$, —NR$_4$C(O)R$_5$, halo, —OR$_4$, cyano, nitro, haloalkoxy, —C(O)R$_4$, —NR$_1$R$_2$, —C(O)OR$_4$, —OC(O)R$_4$, —NR$_4$C(O)NR$_1$R$_2$, —OC(O)NR$_1$R$_2$, —NR$_4$C(O)OR$_5$, —S(O)$_p$R$_4$, or —S(O)$_h$NR$_1$R$_2$;

L is a linker selected from the group consisting of an optionally substituted lower alkyl, and optionally substituted lower alkenyl, —NRCR$_4$R$_5$—, —C(O)—, —OC(O)—, —C(O)O—, —NR—C(O)—, —C(O)—NR—, —NR—C(O)—NR—, —C(S)—, —NR—S(O)$_h$—, —S(O)$_h$—NR—, —NR—C(=NR)—, —NR—C(=NR)—NR—, —NR—C(=N—CN)—NR—, —NR—C(=N—NO$_2$)—NR—, —NR—C(S)—, —C(S)—NR—, or —NR—C(S)—NR—;

R, for each occurrence, is independently selected from —H, an alkyl, acetyl, alkoxycarbonyl, or aralkoxycarbonyl;

R$_1$ and R$_2$, for each occurrence are, independently, H, an optionally substituted alkyl, an optionally substituted alkenyl, an optionally substituted alkynyl, an optionally substituted cycloalkyl, an optionally substituted cycloalkenyl, an optionally substituted heterocyclyl, an optionally substituted aryl, an optionally substituted heteroaryl, an optionally substituted aralkyl, or an optionally substituted heteraralkyl; or R$_1$ and R$_2$ taken together with the nitrogen to which they are attached is optionally substituted heterocyclyl or optionally substituted heteroaryl;

R$_4$ and R$_5$ for each occurrence are, independently, H, an optionally substituted alkyl, an optionally substituted alkenyl, an optionally substituted alkynyl, an optionally substituted cycloalkyl, an optionally substituted cycloalkenyl, an optionally substituted heterocyclyl, an optionally substituted aryl, an optionally substituted heteroaryl, an optionally substituted aralkyl, or an optionally substituted heteraralkyl;

h is 1 or 2;

n is 0 or an integer from 1 to 4; and p, for each occurrence, is, independently, 0, 1, or 2.

18. The method of claim 17, wherein the subject is human.

19. The method according to claim 18, wherein the disorder is selected from transplant rejection; arthritis, rheumatoid arthritis, osteoarthritis and bone diseases associated with increased bone resorption; inflammatory bowel disease, ileitis, ulcerative colitis, Barrett's syndrome, Crohn's disease; asthma, adult respiratory distress syndrome, chronic obstructive airway disease; corneal dystrophy, trachoma, onchocerciasis, uveitis, sympathetic ophthalmitis, endophthalmitis; gingivitis, periodontitis; tuberculosis; leprosy; uremic complications, glomerulonephritis, nephrosis; sclerodermatitis, psoriasis, eczema; chronic demyelinating diseases of the nervous system, multiple sclerosis, AIDS-related neurodegeneration, Alzheimer's disease, infectious meningitis, encephalomyelitis, Parkinson's disease, Huntington's disease, amyotrophic lateral sclerosis viral or autoimmune encephalitis; autoimmune disorders, immune-complex vasculitis, systemic lupus and erythematodes; systemic lupus erythematosus (SLE); cardiomyopathy, ischemic heart disease hypercholesterolemia, atherosclerosis, preeclampsia; chronic liver failure, brain and spinal cord trauma, and cancer.

20. The method of claim 2, 5, 9, 14, or 17, wherein the compound is represented by the following formula:

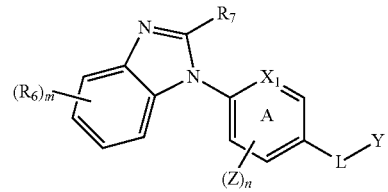

or a pharmaceutically acceptable salt thereof, wherein:

X$_1$ is N;

R$_6$, for each occurrence, and R$_7$ are, independently, selected from the group consisting of an optionally substituted alkyl, an optionally substituted alkenyl, an optionally substituted alkynyl, an optionally substituted cycloalkyl, an optionally substituted cycloalkenyl, an optionally substituted heterocyclyl, an optionally substituted aryl, an optionally substituted heteroaryl, an optionally substituted aralkyl, an optionally substituted heteraralkyl, a haloalkyl, —C(O)NR$_1$R$_2$, —NR$_4$C(O)R$_5$, halo, —OR$_4$, cyano, nitro, haloalkoxy, —C(O)R$_4$, —NR$_1$R$_2$, —C(O)OR$_4$, —OC(O)R$_4$, —NR$_4$C(O)NR$_1$R$_2$, —OC(O)NR$_1$R$_2$, —NR$_4$C(O)OR$_5$, —S(O)$_p$R$_4$, or —S(O)$_h$NR$_1$R$_2$; and m is 0 or an integer from 1 to 4.

21. The method of claim 20, wherein Y is selected from the group consisting of an alkyl, an optionally substituted alkenyl, an optionally substituted phenyl, an optionally substituted pyridyl, an optionally substituted furanyl, an optionally substituted thienyl, an optionally substituted cyclopentyl, an optionally substituted cyclohexyl, an optionally substituted naphthyl, an optionally substituted benzo[1,3]dioxolyl, and an optionally substituted [1,2,3]thiadiazolyl.

22. The method of claim 21, wherein:
$R_6$, for each occurrence, is, independently, selected from the group consisting of —O-(lower alkyl), cyano, —NH$_2$, lower alkyl, —OH, lower haloalkyl, —S(O)$_2$-(lower alkyl), —NHC(O)-(lower alkyl), —C(O)O-(lower alkyl), —C(O)NH$_2$, and —C(O)-(lower alkyl); and
$R_7$ is selected from the group consisting of halo, lower haloalkyl, lower haloalkoxy, —S-(lower alkyl), and —S(O)-(lower alkyl).

23. The method of claim 20, wherein the compound is represented by the following formula:

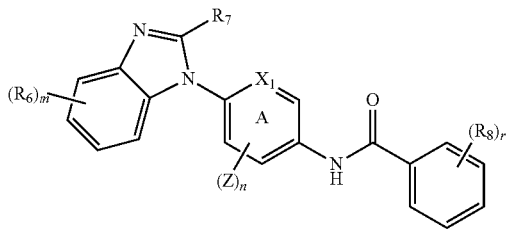

or a pharmaceutically acceptable salt thereof,
wherein:
$R_8$, for each occurrence, is, independently, selected from the group consisting of an optionally substituted alkyl, an optionally substituted alkenyl, an optionally substituted alkynyl, an optionally substituted cycloalkyl, an optionally substituted cycloalkenyl, an optionally substituted heterocyclyl, an optionally substituted aryl, an optionally substituted heteroaryl, an optionally substituted aralkyl, an optionally substituted heteraralkyl, a haloalkyl, —C(O)NR$_1$R$_2$, —NR$_4$C(O)R$_5$, halo, —OR$_4$, cyano, nitro, haloalkoxy, —C(O)R$_4$, —NR$_1$R$_2$, —C(O)OR$_4$, —OC(O)R$_4$, —NR$_4$C(O)NR$_1$R$_2$, —OC(O)NR$_1$R$_2$, —NR$_4$C(O)OR$_5$, —S(O)$_p$R$_4$, or —S(O)$_h$NR$_1$R$_2$; and
r is 0 or an integer from 1 to 5.

24. The method of claim 20, wherein the compound is represented by the following formula:

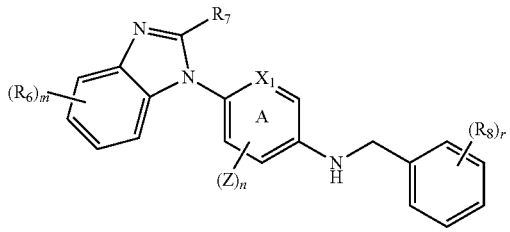

or a pharmaceutically acceptable salt thereof,
wherein:
$R_8$, for each occurrence, is, independently, selected from the group consisting of an optionally substituted alkyl, an optionally substituted alkenyl, an optionally substituted alkynyl, an optionally substituted cycloalkyl, an optionally substituted cycloalkenyl, an optionally substituted heterocyclyl, an optionally substituted aryl, an optionally substituted heteroaryl, an optionally substituted aralkyl, an optionally substituted heteraralkyl, a haloalkyl, —C(O)NR$_1$R$_2$, —NR$_4$C(O)R$_5$, halo, —OR$_4$, cyano, nitro, haloalkoxy, —C(O)R$_4$, —NR$_1$R$_2$, —C(O)OR$_4$, —OC(O)R$_4$, —NR$_4$C(O)NR$_1$R$_2$, —OC(O)NR$_1$R$_2$, —NR$_4$C(O)OR$_5$, —S(O)$_p$R$_4$, or —S(O)$_h$NR$_1$R$_2$; and
r is 0 or an integer from 1 to 5.

25. The method of claim 2, 5, 9, 14, or 17, wherein the subject is administered one or more compounds selected from the group consisting of:
2,3-Difluoro-N-[4-(2-trifluoromethyl-5,6,7,8-tetrahydroindolizin-3-yl)-phenyl]-benzamide;
2-Methyl-N-[4-(2-trifluoromethyl-5,6,7,8-tetrahydroindolizin-3-yl)-phenyl]-benzamide;
2,3-Difluoro-N-[4-(2-trifluoromethyl-5,6,7,8-tetrahydroindolizin-3-yl)-phenyl]-benzamide;
4-Methyl-[1,2,3]thiadiazole-5-carboxylic acid {N-[4-(2-chloro-5,6,7,8-tetrahydroindolizin-3-yl)-phenyl]}amide;
N'-[2-(2-trifluoromethyl-benzoimidazol-1-yl)-pyrid-5-yl]-N-(2,5-difluoro-phenyl)-thiourea;
2,3-Difluoro-N-[2-(2-trifluoromethyl-benzoimidazol-1-yl)-pyrid-3-yl]-benzamide;
2,5-Difluoro-N-[2-(2-trifluoromethyl-benzoimidazol-1-yl)-pyrid-5-yl]-benzamide;
2,3-Difluoro-N-[4-(2-trifluoromethyl-imidazo[4,5-b]pyrid-3-yl)-phenyl]-benzamide;
2,5-Difluoro-N-[4-(2-trifluoromethyl-imidazo[4,5-b]pyrid-3-yl)-phenyl]-benzamide;
4-Methyl-[1,2,3]thiadiazole-5-carboxylic acid {N-[4-(2-trifluoromethyl-imidazo[4,5-b]pyrid-3-yl)-phenyl]}amide;
2,3-Difluoro-N-[4-(2-trifluoromethyl-imidazo[4,5-c]pyrid-1-yl)-phenyl]-benzamide;
4-Methyl-[1,2,3]thiadiazole-5-carboxylic acid {N-[2-(2-trifluoromethyl-benzoimidazol-1-yl)-pyrid-5-yl]}amide;
2,3-Difluoro-N-[4-(2-trifluoromethyl-imidazo[1,2-a]pyrid-3-yl)-phenyl]-benzamide;
2-Methyl-N-[4-(7-methoxy-5,6,7,8-tetrahydroindolizin-3-yl)-phenyl]-benzamide;
3-Methyl-N-[4-(7-methoxy-5,6,7,8-tetrahydroindolizin-3-yl)-phenyl]-isonicotinamide;
2-Methyl-3-fluoro-N-[4-(7-methoxy-5,6,7,8-tetrahydroindolizin-3-yl)-phenyl]-benzamide;
3-Cyano-N-[4-(7-methoxy-5,6,7,8-tetrahydroindolizin-3-yl)-phenyl]-benzamide;
2-Nitro-N-[4-(7-methoxy-5,6,7,8-tetrahydroindolizin-3-yl)-phenyl]-benzamide;
2,6-Difluoro-3-iodo-N-[4-(7-methoxy-5,6,7,8-tetrahydroindolizin-3-yl)-phenyl]-benzamide;
2-Chloro-N-[4-(7-methoxy-5,6,7,8-tetrahydroindolizin-3-yl)-phenyl]-benzamide;
N-[4-(7-methoxy-5,6,7,8-tetrahydroindolizin-3-yl)-phenyl]-cyclohexanecarboxylic acid amide;
2-Methyl-N-[4-(7-methoxy-imidazo[1,2-a]pyrid-3-yl)-phenyl]-benzamide;
3-Fluoro-N-[4-(7-methoxy-imidazo[1,2-a]pyrid-3-yl)-phenyl]-isonicotinamide;
2-Methyl-3-fluoro-N-[4-(7-methoxy-imidazo[1,2-a]pyrid-3-yl)-phenyl]-benzamide;
3-Cyano-N-[4-(7-methoxy-imidazo[1,2-a]pyrid-3-yl)-phenyl]-benzamide;
3-Nitro-N-[4-(7-methoxy-imidazo[1,2-a]pyrid-3-yl)-phenyl]-benzamide;

2,6-Difluoro-3-iodo-N-[4-(7-methoxy-imidazo[1,2-a]pyrid-3-yl)-phenyl]-benzamide;
2-Chloro-N-[4-(7-methoxy-imidazo[1,2-a]pyrid-3-yl)-phenyl]-benzamide;
N-[4-(7-methoxy-imidazo[1,2-a]pyrid-3-yl)-phenyl]-cyclohexanecarboxylic acid amide; and
pharmaceutically acceptable salts thereof.

\* \* \* \* \*